US008845637B2

(12) United States Patent
Schmitz et al.

(10) Patent No.: US 8,845,637 B2
(45) Date of Patent: Sep. 30, 2014

(54) TISSUE ACCESS GUIDEWIRE SYSTEM AND METHOD

(71) Applicant: Baxano Surgical, Inc., Raleigh, NC (US)

(72) Inventors: Gregory P. Schmitz, Los Gatos, CA (US); Jefferey Bleam, Boulder Creek, CA (US); Roy Leguidleguid, Union City, CA (US); Jeffery L. Bleich, Palo Alto, CA (US)

(73) Assignee: Baxano Surgical, Inc., Raleigh, NC (US)

( * ) Notice: Subject to any disclaimer, the term of this patent is extended or adjusted under 35 U.S.C. 154(b) by 0 days.

(21) Appl. No.: 14/023,893

(22) Filed: Sep. 11, 2013

(65) Prior Publication Data
US 2014/0012239 A1    Jan. 9, 2014

Related U.S. Application Data

(60) Division of application No. 12/917,253, filed on Nov. 1, 2010, now Pat. No. 8,551,097, which is a continuation of application No. 11/468,247, filed on Aug. 29, 2006, now Pat. No. 7,857,813.

(51) Int. Cl.
A61B 10/00 (2006.01)
A61M 25/00 (2006.01)
(Continued)

(52) U.S. Cl.
CPC ............ A61B 17/00 (2013.01); A61B 17/8897 (2013.01); A61B 17/00234 (2013.01); A61B 17/1659 (2013.01); A61B 17/1757 (2013.01); A61B 17/1604 (2013.01); A61B 17/0482 (2013.01); A61B 2017/00477 (2013.01); A61B 17/0483 (2013.01); A61B 17/1671 (2013.01); A61B 1/3135 (2013.01); A61B 17/1611 (2013.01); A61M 25/09 (2013.01)
USPC .......................................................... 606/79

(58) Field of Classification Search
CPC ................ A61B 17/1671; A61B 2017/32006; A61B 2017/320004; A61M 25/09041; A61M 25/09
USPC ............ 606/79, 106; 600/564, 569, 570, 585
See application file for complete search history.

(56) References Cited

U.S. PATENT DOCUMENTS 184,804 A    11/1876  Stohlmann
289,104 A    11/1883  How
(Continued)

FOREIGN PATENT DOCUMENTS

CN    1338911 A    3/2002
CN    101291633 A  10/2008
(Continued)

OTHER PUBLICATIONS

Leguidleguid et al.; U.S. Appl. No. 14/061,641 entitled "Tissue Modification Devices," filed Oct. 23, 2013.
(Continued)

Primary Examiner — Sean Dougherty
(74) Attorney, Agent, or Firm — Shay Glenn LLP

(57) ABSTRACT

A method and system for guiding at least a portion of a surgical device to a desired position between two tissues in a patient's body involves coupling a guidewire to the device and pulling the distal end of the guidewire to guide at least a portion of the surgical device to a desired position between the two tissues. The surgical device generally includes one or more guidewire coupling members and may comprise a tissue access device. A system may include a guidewire and a surgical device. In some embodiments, a guidewire, a tissue access device, and one or more additional devices to use with the access device may be provided. Methods, devices and systems may be used in open, less-invasive or percutaneous surgical procedures, in various embodiments.

16 Claims, 34 Drawing Sheets

(51) Int. Cl.
*A61B 17/00* (2006.01)
*A61F 11/00* (2006.01)
*A61B 17/17* (2006.01)
*A61M 25/09* (2006.01)
*A61B 17/88* (2006.01)
*A61B 17/16* (2006.01)
*A61B 17/04* (2006.01)
*A61B 1/313* (2006.01)

(56) References Cited

U.S. PATENT DOCUMENTS

| | | |
|---|---|---|
| 863,389 A | 8/1907 | Harkin |
| 1,039,487 A | 9/1912 | Casebolt |
| 1,201,467 A | 10/1916 | Hoglund |
| 1,374,638 A | 4/1921 | De Cew et al. |
| 1,543,195 A | 6/1925 | Thygesen |
| 1,690,812 A | 11/1928 | Bertels |
| 1,938,200 A | 12/1933 | Wells |
| 2,243,757 A | 5/1941 | Kohls et al. |
| 2,269,749 A | 1/1942 | Wilkie |
| 2,372,553 A | 3/1945 | Coddington |
| 2,437,697 A | 3/1948 | Kalom |
| 2,516,882 A | 8/1950 | Kalom |
| 2,704,064 A | 5/1955 | Fizzell |
| 2,820,281 A | 1/1958 | Amsen |
| 2,843,128 A | 7/1958 | Storz |
| 2,982,005 A | 5/1961 | Booth |
| 3,124,824 A | 3/1964 | Lutz |
| RE25,582 E | 5/1964 | Davies |
| 3,150,470 A | 9/1964 | Barron |
| 3,200,814 A | 8/1965 | Taylor et al. |
| 3,214,824 A | 11/1965 | Brown |
| 3,389,447 A | 6/1968 | Theobald et al. |
| 3,491,776 A | 1/1970 | Fleming |
| 3,495,590 A | 2/1970 | Zeiller |
| 3,528,152 A | 9/1970 | Funakubo et al. |
| 3,624,484 A | 11/1971 | Colyer |
| 3,640,280 A | 2/1972 | Slanker et al. |
| 3,651,844 A | 3/1972 | Barnes |
| 3,664,329 A | 5/1972 | Naylor |
| 3,682,162 A | 8/1972 | Colyer |
| 3,699,729 A | 10/1972 | Garvey et al. |
| 3,752,166 A | 8/1973 | Lyon et al. |
| 3,774,355 A | 11/1973 | Dawson et al. |
| 3,830,226 A | 8/1974 | Staub et al. |
| 3,835,859 A | 9/1974 | Roberts et al. |
| 3,956,858 A | 5/1976 | Catlin et al. |
| 3,957,036 A | 5/1976 | Normann |
| 3,978,862 A | 9/1976 | Morrison |
| 3,999,294 A | 12/1976 | Shoben |
| 4,015,931 A | 4/1977 | Thakur |
| 4,099,519 A | 7/1978 | Warren |
| 4,108,182 A | 8/1978 | Hartman et al. |
| 4,160,320 A | 7/1979 | Wikoff |
| 4,172,440 A | 10/1979 | Schneider et al. |
| 4,203,444 A | 5/1980 | Bonnell et al. |
| 4,207,897 A | 6/1980 | Lloyd et al. |
| 4,259,276 A | 3/1981 | Rawlings |
| 4,405,061 A | 9/1983 | Bergandy |
| D273,806 S | 5/1984 | Bolesky et al. |
| 4,464,836 A | 8/1984 | Hissa |
| 4,502,184 A | 3/1985 | Karubian |
| 4,515,168 A | 5/1985 | Chester et al. |
| 4,518,022 A | 5/1985 | Valdes et al. |
| 4,545,374 A | 10/1985 | Jacobson |
| 4,573,448 A | 3/1986 | Kambin |
| 4,580,545 A | 4/1986 | Dorsten |
| 4,590,949 A | 5/1986 | Pohndorf |
| 4,616,660 A | 10/1986 | Johns |
| 4,621,636 A | 11/1986 | Fogarty |
| 4,625,725 A | 12/1986 | Davison et al. |
| 4,660,571 A | 4/1987 | Hess et al. |
| 4,678,459 A | 7/1987 | Onik et al. |
| 4,690,642 A | 9/1987 | Kyotani |
| 4,700,702 A | 10/1987 | Nilsson |
| 4,709,699 A | 12/1987 | Michael et al. |
| 4,741,343 A | 5/1988 | Bowman |
| 4,750,249 A | 6/1988 | Richardson |
| 4,794,931 A | 1/1989 | Yock |
| 4,808,157 A | 2/1989 | Coombs |
| 4,817,628 A | 4/1989 | Zealear et al. |
| 4,856,193 A | 8/1989 | Grachan |
| 4,867,155 A | 9/1989 | Isaacson |
| 4,872,452 A | 10/1989 | Alexson |
| 4,873,978 A | 10/1989 | Ginsburg |
| 4,883,460 A | 11/1989 | Zanetti |
| 4,894,063 A | 1/1990 | Nashe |
| 4,912,799 A | 4/1990 | Coleman, Jr. |
| RE33,258 E | 7/1990 | Onik et al. |
| 4,943,295 A | 7/1990 | Hartlaub et al. |
| 4,946,462 A | 8/1990 | Watanabe |
| 4,957,117 A | 9/1990 | Wysham |
| 4,962,766 A | 10/1990 | Herzon |
| 4,973,329 A | 11/1990 | Park et al. |
| 4,990,148 A | 2/1991 | Worrick, III et al. |
| 4,994,036 A | 2/1991 | Biscoping et al. |
| 4,994,072 A | 2/1991 | Bhate et al. |
| 4,995,200 A | 2/1991 | Eberhart |
| 5,019,082 A | 5/1991 | Frey et al. |
| 5,025,787 A | 6/1991 | Sutherland et al. |
| 5,026,379 A | 6/1991 | Yoon |
| 5,026,386 A | 6/1991 | Michelson |
| 5,078,137 A | 1/1992 | Edell et al. |
| 5,089,003 A | 2/1992 | Fallin et al. |
| 5,100,424 A | 3/1992 | Jang et al. |
| 5,108,403 A | 4/1992 | Stern |
| 5,123,400 A | 6/1992 | Edgerton |
| 5,125,928 A | 6/1992 | Parins et al. |
| 5,147,364 A | 9/1992 | Comparetto |
| 5,152,749 A | 10/1992 | Giesy et al. |
| 5,161,534 A | 11/1992 | Berthiaume |
| 5,163,939 A | 11/1992 | Winston |
| 5,176,649 A | 1/1993 | Wakabayashi |
| 5,178,145 A | 1/1993 | Rea |
| 5,178,161 A | 1/1993 | Kovacs |
| 5,191,888 A | 3/1993 | Palmer et al. |
| 5,195,507 A | 3/1993 | Bilweis |
| 5,201,704 A | 4/1993 | Ray |
| 5,215,105 A | 6/1993 | Kizelshteyn et al. |
| 5,219,358 A | 6/1993 | Bendel et al. |
| 5,234,435 A | 8/1993 | Seagrave, Jr. |
| 5,242,418 A | 9/1993 | Weinstein |
| 5,250,035 A | 10/1993 | Smith et al. |
| 5,255,691 A | 10/1993 | Otten |
| 5,271,415 A | 12/1993 | Foerster et al. |
| 5,281,218 A | 1/1994 | Imran |
| 5,284,153 A | 2/1994 | Raymond et al. |
| 5,284,154 A | 2/1994 | Raymond et al. |
| 5,300,077 A | 4/1994 | Howell |
| 5,325,868 A | 7/1994 | Kimmelstiel |
| 5,341,807 A | 8/1994 | Nardella |
| 5,351,679 A | 10/1994 | Mayzels et al. |
| 5,353,784 A | 10/1994 | Nady-Mohamed |
| 5,353,789 A | 10/1994 | Schlobohm |
| 5,353,802 A | 10/1994 | Ollmar |
| 5,360,441 A | 11/1994 | Otten |
| 5,365,928 A | 11/1994 | Rhinehart et al. |
| 5,374,261 A | 12/1994 | Yoon |
| 5,383,879 A | 1/1995 | Phillips |
| 5,385,146 A | 1/1995 | Goldreyer |
| 5,387,218 A | 2/1995 | Meswania |
| 5,396,880 A | 3/1995 | Kagan et al. |
| 5,421,348 A | 6/1995 | Larnard |
| 5,423,331 A | 6/1995 | Wysham |
| 5,437,661 A | 8/1995 | Rieser |
| 5,439,464 A | 8/1995 | Shapiro |
| 5,441,044 A | 8/1995 | Tovey et al. |
| 5,441,510 A | 8/1995 | Simpson et al. |
| 5,454,815 A | 10/1995 | Geisser et al. |
| 5,456,254 A | 10/1995 | Pietroski et al. |
| 5,496,325 A | 3/1996 | McLees |
| 5,512,037 A | 4/1996 | Russell et al. |
| 5,515,848 A | 5/1996 | Corbett, III et al. |

(56) References Cited

U.S. PATENT DOCUMENTS

| | | |
|---|---|---|
| 5,531,749 A | 7/1996 | Michelson |
| 5,534,009 A | 7/1996 | Lander |
| 5,546,958 A | 8/1996 | Thorud et al. |
| 5,554,110 A | 9/1996 | Edwards et al. |
| 5,555,892 A | 9/1996 | Tipton |
| 5,560,372 A | 10/1996 | Cory |
| 5,562,695 A | 10/1996 | Obenchain |
| 5,571,181 A | 11/1996 | Li |
| 5,582,618 A | 12/1996 | Chin et al. |
| 5,591,170 A | 1/1997 | Spievack et al. |
| 5,598,848 A | 2/1997 | Swanson et al. |
| 5,620,447 A | 4/1997 | Smith et al. |
| 5,630,426 A | 5/1997 | Eggers et al. |
| 5,634,475 A | 6/1997 | Wolvek |
| 5,643,304 A | 7/1997 | Schechter et al. |
| 5,651,373 A | 7/1997 | Mah |
| 5,656,012 A | 8/1997 | Sienkiewicz |
| 5,680,860 A | 10/1997 | Imran |
| 5,681,324 A | 10/1997 | Kammerer et al. |
| 5,697,889 A | 12/1997 | Slotman et al. |
| 5,709,697 A | 1/1998 | Ratcliff et al. |
| 5,725,530 A | 3/1998 | Popken |
| 5,735,792 A | 4/1998 | Vanden Hoek et al. |
| 5,755,732 A | 5/1998 | Green et al. |
| 5,759,159 A | 6/1998 | Masreliez |
| 5,762,629 A | 6/1998 | Kambin |
| 5,766,168 A | 6/1998 | Mantell |
| 5,769,865 A | 6/1998 | Kermode et al. |
| 5,775,331 A | 7/1998 | Raymond et al. |
| 5,779,642 A | 7/1998 | Nightengale |
| 5,788,653 A | 8/1998 | Lorenzo |
| 5,792,044 A | 8/1998 | Foley et al. |
| 5,795,308 A | 8/1998 | Russin |
| 5,800,350 A | 9/1998 | Coppleson et al. |
| 5,803,902 A | 9/1998 | Sienkiewicz et al. |
| 5,803,904 A | 9/1998 | Mehdizadeh |
| 5,807,263 A | 9/1998 | Chance |
| 5,810,744 A | 9/1998 | Chu et al. |
| 5,813,405 A | 9/1998 | Montano, Jr. et al. |
| 5,824,040 A | 10/1998 | Cox et al. |
| 5,830,151 A | 11/1998 | Hadzic et al. |
| 5,830,157 A | 11/1998 | Foote |
| 5,830,188 A | 11/1998 | Abouleish |
| 5,833,692 A | 11/1998 | Cesarini et al. |
| 5,836,810 A | 11/1998 | Åsum |
| 5,836,948 A | 11/1998 | Zucherman et al. |
| 5,843,110 A | 12/1998 | Dross et al. |
| 5,846,196 A | 12/1998 | Siekmeyer et al. |
| 5,846,244 A | 12/1998 | Cripe |
| 5,851,191 A | 12/1998 | Gozani |
| 5,851,209 A | 12/1998 | Kummer et al. |
| 5,851,214 A | 12/1998 | Larsen et al. |
| 5,853,373 A | 12/1998 | Griffith et al. |
| 5,865,844 A | 2/1999 | Plaia et al. |
| 5,868,767 A | 2/1999 | Farley et al. |
| 5,879,353 A | 3/1999 | Terry |
| 5,885,219 A | 3/1999 | Nightengale |
| 5,895,417 A | 4/1999 | Pomeranz et al. |
| 5,897,583 A | 4/1999 | Meyer et al. |
| 5,899,909 A | 5/1999 | Claren et al. |
| 5,904,657 A | 5/1999 | Unsworth et al. |
| 5,916,173 A | 6/1999 | Kirsner |
| 5,918,604 A | 7/1999 | Whelan |
| 5,919,190 A | 7/1999 | VanDusseldorp |
| 5,928,158 A | 7/1999 | Aristides |
| 5,941,822 A | 8/1999 | Skladnev et al. |
| 5,961,522 A | 10/1999 | Mehdizadeh |
| 5,972,013 A | 10/1999 | Schmidt |
| 5,976,110 A | 11/1999 | Greengrass et al. |
| 5,976,146 A | 11/1999 | Ogawa et al. |
| 6,002,964 A | 12/1999 | Feler et al. |
| 6,004,326 A | 12/1999 | Castro et al. |
| 6,004,330 A | 12/1999 | Middleman et al. |
| 6,010,493 A | 1/2000 | Snoke |
| 6,015,406 A | 1/2000 | Goble et al. |
| 6,022,362 A | 2/2000 | Lee et al. |
| 6,030,383 A | 2/2000 | Benderev |
| 6,030,401 A | 2/2000 | Marino |
| 6,038,480 A | 3/2000 | Hrdlicka et al. |
| 6,048,345 A | 4/2000 | Berke et al. |
| 6,068,642 A | 5/2000 | Johnson et al. |
| 6,073,051 A | 6/2000 | Sharkey et al. |
| 6,099,514 A | 8/2000 | Sharkey et al. |
| 6,102,930 A | 8/2000 | Simmons, Jr. |
| 6,106,558 A | 8/2000 | Picha |
| 6,113,534 A | 9/2000 | Koros et al. |
| D432,384 S | 10/2000 | Simons |
| 6,132,387 A | 10/2000 | Gozani et al. |
| 6,136,014 A | 10/2000 | Sirimanne et al. |
| 6,142,993 A | 11/2000 | Whayne et al. |
| 6,142,994 A | 11/2000 | Swanson et al. |
| 6,146,380 A | 11/2000 | Racz et al. |
| 6,152,894 A | 11/2000 | Kubler |
| 6,169,916 B1 | 1/2001 | West |
| 6,205,360 B1 | 3/2001 | Carter et al. |
| 6,214,001 B1 | 4/2001 | Casscells et al. |
| 6,214,016 B1 | 4/2001 | Williams et al. |
| 6,236,892 B1 | 5/2001 | Feler |
| 6,251,115 B1 | 6/2001 | Williams et al. |
| 6,256,540 B1 | 7/2001 | Panescu et al. |
| 6,259,945 B1 | 7/2001 | Epstein et al. |
| 6,261,582 B1 | 7/2001 | Needham et al. |
| 6,266,551 B1 | 7/2001 | Osadchy et al. |
| 6,266,558 B1 | 7/2001 | Gozani et al. |
| 6,267,760 B1 | 7/2001 | Swanson |
| 6,272,367 B1 | 8/2001 | Chance |
| 6,277,094 B1 | 8/2001 | Schendel |
| 6,280,447 B1 | 8/2001 | Marino et al. |
| 6,292,702 B1 | 9/2001 | King et al. |
| 6,298,256 B1 | 10/2001 | Meyer |
| 6,312,392 B1 | 11/2001 | Herzon |
| 6,324,418 B1 | 11/2001 | Crowley et al. |
| 6,324,432 B1 | 11/2001 | Rigaux et al. |
| 6,325,764 B1 | 12/2001 | Griffith et al. |
| 6,334,068 B1 | 12/2001 | Hacker |
| 6,343,226 B1 | 1/2002 | Sunde et al. |
| 6,358,254 B1 | 3/2002 | Anderson |
| 6,360,750 B1 | 3/2002 | Gerber et al. |
| 6,364,886 B1 | 4/2002 | Sklar |
| 6,368,324 B1 | 4/2002 | Dinger et al. |
| 6,370,411 B1 | 4/2002 | Osadchy et al. |
| 6,370,435 B2 | 4/2002 | Panescu et al. |
| 6,383,509 B1 | 5/2002 | Donovan et al. |
| 6,390,906 B1 | 5/2002 | Subramanian |
| 6,391,028 B1 | 5/2002 | Fanton et al. |
| 6,416,505 B1 | 7/2002 | Fleischman et al. |
| 6,423,071 B1 | 7/2002 | Lawson |
| 6,423,080 B1 | 7/2002 | Gellman et al. |
| 6,425,887 B1 | 7/2002 | McGuckin et al. |
| 6,436,101 B1 | 8/2002 | Hamada |
| 6,442,848 B1 | 9/2002 | Dean |
| 6,446,621 B1 | 9/2002 | Svensson |
| 6,451,335 B1 | 9/2002 | Goldenheim et al. |
| 6,454,767 B2 | 9/2002 | Alleyne |
| 6,464,682 B1 | 10/2002 | Snoke |
| 6,466,817 B1 | 10/2002 | Kaula et al. |
| 6,468,289 B1 | 10/2002 | Bonutti |
| 6,470,209 B2 | 10/2002 | Snoke |
| 6,478,805 B1 | 11/2002 | Marino et al. |
| 6,487,439 B1 | 11/2002 | Skladnev et al. |
| 6,488,636 B2 | 12/2002 | Bryan et al. |
| 6,491,646 B1 | 12/2002 | Blackledge |
| 6,500,128 B2 | 12/2002 | Marino |
| 6,500,189 B1 | 12/2002 | Lang et al. |
| 6,512,958 B1 | 1/2003 | Swoyer et al. |
| 6,516,223 B2 | 2/2003 | Hofmann |
| 6,527,786 B1 | 3/2003 | Davis et al. |
| 6,533,749 B1 | 3/2003 | Mitusina et al. |
| 6,535,759 B1 | 3/2003 | Epstein et al. |
| 6,540,742 B1 | 4/2003 | Thomas et al. |
| 6,540,761 B2 | 4/2003 | Houser |
| 6,546,270 B1 | 4/2003 | Goldin et al. |
| 6,558,353 B2 | 5/2003 | Zohmann |
| 6,562,033 B2 | 5/2003 | Shah et al. |

(56) References Cited

U.S. PATENT DOCUMENTS

| | | |
|---|---|---|
| 6,564,078 B1 | 5/2003 | Marino et al. |
| 6,564,079 B1 | 5/2003 | Cory et al. |
| 6,564,088 B1 | 5/2003 | Soller et al. |
| 6,569,160 B1 | 5/2003 | Goldin et al. |
| 6,575,979 B1 | 6/2003 | Cragg |
| 6,579,291 B1 | 6/2003 | Keith et al. |
| 6,584,345 B2 | 6/2003 | Govari |
| 6,592,559 B1 | 7/2003 | Pakter et al. |
| 6,595,932 B2 | 7/2003 | Ferrera |
| 6,597,955 B2 | 7/2003 | Panescu et al. |
| 6,606,523 B1 | 8/2003 | Jenkins |
| 6,607,530 B1 | 8/2003 | Carl et al. |
| 6,609,018 B2 | 8/2003 | Cory et al. |
| 6,610,066 B2 | 8/2003 | Dinger et al. |
| 6,620,129 B2 | 9/2003 | Stecker et al. |
| 6,622,731 B2 | 9/2003 | Daniel et al. |
| 6,624,510 B1 | 9/2003 | Chan et al. |
| 6,626,916 B1 | 9/2003 | Yeung et al. |
| 6,632,184 B1 | 10/2003 | Truwit |
| 6,638,233 B2 | 10/2003 | Corvi et al. |
| RE38,335 E | 11/2003 | Aust et al. |
| 6,648,883 B2 | 11/2003 | Francischelli et al. |
| 6,666,874 B2 | 12/2003 | Heitzmann et al. |
| 6,673,063 B2 | 1/2004 | Brett |
| 6,673,068 B1 | 1/2004 | Berube |
| 6,678,552 B2 | 1/2004 | Pearlman |
| 6,682,535 B2 | 1/2004 | Hoogland |
| 6,682,536 B2 | 1/2004 | Vardi et al. |
| 6,699,246 B2 | 3/2004 | Zucherman et al. |
| 6,723,049 B2 | 4/2004 | Skladnev et al. |
| 6,726,531 B1 | 4/2004 | Harrel |
| 6,726,685 B2 | 4/2004 | To et al. |
| 6,733,496 B2 | 5/2004 | Sharkey et al. |
| 6,736,835 B2 | 5/2004 | Pellegrino et al. |
| 6,746,451 B2 | 6/2004 | Middleton et al. |
| 6,752,814 B2 | 6/2004 | Gellman et al. |
| 6,760,616 B2 | 7/2004 | Hoey et al. |
| 6,772,012 B2 | 8/2004 | Ricart et al. |
| 6,776,765 B2 | 8/2004 | Soukup et al. |
| 6,788,966 B2 | 9/2004 | Kenan et al. |
| 6,790,210 B1 | 9/2004 | Cragg et al. |
| 6,805,695 B2 | 10/2004 | Keith et al. |
| 6,805,697 B1 | 10/2004 | Helm et al. |
| 6,807,444 B2 | 10/2004 | Tu et al. |
| 6,830,561 B2 | 12/2004 | Jansen et al. |
| 6,830,570 B1 | 12/2004 | Frey et al. |
| 6,832,111 B2 | 12/2004 | Tu et al. |
| 6,845,264 B1 | 1/2005 | Skladnev et al. |
| 6,847,849 B2 | 1/2005 | Mamo et al. |
| 6,851,430 B2 | 2/2005 | Tsou |
| 6,865,409 B2 | 3/2005 | Getsla et al. |
| 6,872,204 B2 | 3/2005 | Houser |
| 6,875,221 B2 | 4/2005 | Cull |
| 6,882,879 B2 | 4/2005 | Rock |
| 6,884,220 B2 | 4/2005 | Aviv et al. |
| 6,890,353 B2 | 5/2005 | Cohn et al. |
| 6,899,716 B2 | 5/2005 | Cragg |
| 6,907,884 B2 | 6/2005 | Pellegrino et al. |
| 6,911,003 B2 | 6/2005 | Anderson et al. |
| 6,911,016 B2 | 6/2005 | Balzum et al. |
| 6,916,328 B2 | 7/2005 | Brett |
| 6,923,813 B2 | 8/2005 | Phillips et al. |
| 6,929,647 B2 | 8/2005 | Cohen |
| 6,949,104 B2 | 9/2005 | Griffis et al. |
| 6,953,461 B2 | 10/2005 | McClurken et al. |
| 6,962,587 B2 | 11/2005 | Johnson et al. |
| 6,971,986 B2 | 12/2005 | Staskin et al. |
| 6,972,199 B2 | 12/2005 | Lebouitz et al. |
| 6,973,342 B1 | 12/2005 | Swanson |
| 6,976,986 B2 | 12/2005 | Berube |
| 6,991,643 B2 | 1/2006 | Saadat |
| 6,994,693 B2 | 2/2006 | Tal |
| 6,997,934 B2 | 2/2006 | Snow et al. |
| 6,999,820 B2 | 2/2006 | Jordan |
| 7,001,333 B2 | 2/2006 | Hamel et al. |
| 7,008,431 B2 | 3/2006 | Simonson |
| 7,010,352 B2 | 3/2006 | Hogan |
| 7,011,635 B1 | 3/2006 | Delay |
| 7,011,663 B2 | 3/2006 | Michelson |
| 7,014,616 B2 | 3/2006 | Ferrera |
| 7,033,373 B2 | 4/2006 | de la Torre et al. |
| 7,041,099 B2 | 5/2006 | Thomas et al. |
| 7,047,084 B2 | 5/2006 | Erickson et al. |
| 7,048,682 B2 | 5/2006 | Neisz et al. |
| 7,050,848 B2 | 5/2006 | Hoey et al. |
| 7,063,682 B1 | 6/2006 | Whayne et al. |
| 7,070,556 B2 | 7/2006 | Anderson et al. |
| 7,070,596 B1 | 7/2006 | Woloszko et al. |
| 7,079,883 B2 | 7/2006 | Marino et al. |
| 7,081,122 B1 | 7/2006 | Reiley et al. |
| 7,087,053 B2 | 8/2006 | Vanney |
| 7,087,058 B2 | 8/2006 | Cragg |
| 7,107,104 B2 | 9/2006 | Keravel et al. |
| 7,118,576 B2 | 10/2006 | Gitis et al. |
| 7,141,019 B2 | 11/2006 | Pearlman |
| 7,166,073 B2 | 1/2007 | Ritland |
| 7,166,081 B2 | 1/2007 | McKinley |
| 7,166,107 B2 | 1/2007 | Anderson |
| 7,169,107 B2 | 1/2007 | Jersey-Willuhn et al. |
| 7,169,147 B2 | 1/2007 | Nosel |
| 7,189,240 B1 | 3/2007 | Dekel |
| 7,198,598 B2 | 4/2007 | Smith et al. |
| 7,198,626 B2 | 4/2007 | Lee et al. |
| 7,207,949 B2 | 4/2007 | Miles et al. |
| 7,211,082 B2 | 5/2007 | Hall et al |
| 7,214,186 B2 | 5/2007 | Ritland |
| 7,214,197 B2 | 5/2007 | Prass |
| 7,216,001 B2 | 5/2007 | Hacker et al. |
| 7,223,278 B2 | 5/2007 | Davison et al. |
| 7,236,832 B2 | 6/2007 | Hemmerling et al. |
| 7,239,911 B2 | 7/2007 | Scholz |
| 7,270,658 B2 | 9/2007 | Woloszko et al. |
| 7,282,061 B2 | 10/2007 | Sharkey et al. |
| 7,337,005 B2 | 2/2008 | Kim et al. |
| 7,337,006 B2 | 2/2008 | Kim et al. |
| 7,470,236 B1 | 12/2008 | Kelleher et al. |
| 7,494,473 B2 | 2/2009 | Eggers et al. |
| 7,503,920 B2 | 3/2009 | Siegal |
| 7,507,218 B2 | 3/2009 | Aliski et al. |
| 7,553,307 B2 | 6/2009 | Bleich et al. |
| 7,555,343 B2 | 6/2009 | Bleich |
| 7,578,819 B2 | 8/2009 | Bleich et al. |
| 7,617,006 B2 | 11/2009 | Metzler et al. |
| 7,641,658 B2 | 1/2010 | Shaolian et al. |
| 7,655,026 B2 | 2/2010 | Justis et al. |
| 7,666,186 B2 | 2/2010 | Harp |
| 7,666,209 B2 | 2/2010 | Zucherman et al. |
| 7,738,968 B2 | 6/2010 | Bleich |
| 7,738,969 B2 | 6/2010 | Bleich |
| 7,740,631 B2 | 6/2010 | Bleich et al. |
| 7,857,813 B2 | 12/2010 | Schmitz et al. |
| 7,887,538 B2 | 2/2011 | Bleich et al. |
| 7,918,849 B2 | 4/2011 | Bleich et al. |
| 7,938,830 B2 | 5/2011 | Saadat et al. |
| 7,959,577 B2 | 6/2011 | Schmitz et al. |
| 7,963,915 B2 | 6/2011 | Bleich |
| 8,048,080 B2 | 11/2011 | Bleich et al. |
| 8,062,298 B2 | 11/2011 | Schmitz et al. |
| 8,062,300 B2 | 11/2011 | Schmitz et al. |
| 8,092,456 B2 | 1/2012 | Bleich et al. |
| 8,192,435 B2 | 6/2012 | Bleich et al. |
| 8,192,436 B2 | 6/2012 | Schmitz et al. |
| 8,221,397 B2 | 7/2012 | Bleich et al. |
| 8,257,356 B2 | 9/2012 | Bleich et al. |
| 8,303,516 B2 | 11/2012 | Schmitz et al. |
| 8,366,712 B2 | 2/2013 | Bleich et al. |
| 8,394,102 B2 | 3/2013 | Garabedian et al. |
| 8,398,641 B2 | 3/2013 | Wallace et al. |
| 8,409,206 B2 | 4/2013 | Wallace et al. |
| 8,419,653 B2 | 4/2013 | Bleich et al. |
| 8,430,881 B2 | 4/2013 | Bleich et al. |
| 8,551,097 B2 | 10/2013 | Schmitz et al. |
| 8,568,416 B2 | 10/2013 | Schmitz et al. |
| 8,579,902 B2 | 11/2013 | Bleich et al. |

(56) References Cited

U.S. PATENT DOCUMENTS

| | | |
|---|---|---|
| 8,585,704 B2 | 11/2013 | Schmitz et al. |
| 2001/0014806 A1 | 8/2001 | Ellman et al. |
| 2001/0025192 A1 | 9/2001 | Gerber et al. |
| 2001/0039419 A1 | 11/2001 | Francischelli et al. |
| 2001/0049527 A1 | 12/2001 | Cragg |
| 2001/0053885 A1 | 12/2001 | Gielen et al. |
| 2002/0016555 A1 | 2/2002 | Ritchart et al. |
| 2002/0019637 A1 | 2/2002 | Frey et al. |
| 2002/0022788 A1 | 2/2002 | Corvi et al. |
| 2002/0022873 A1 | 2/2002 | Erickson et al. |
| 2002/0029060 A1 | 3/2002 | Hogendijk |
| 2002/0106681 A1 | 8/2002 | Wexler et al. |
| 2002/0128700 A1 | 9/2002 | Cross |
| 2002/0138091 A1 | 9/2002 | Pflueger |
| 2002/0165590 A1 | 11/2002 | Crowe et al. |
| 2002/0183647 A1 | 12/2002 | Gozani et al. |
| 2003/0015203 A1 | 1/2003 | Makower et al. |
| 2003/0023190 A1 | 1/2003 | Cox |
| 2003/0045808 A1 | 3/2003 | Kaula et al. |
| 2003/0045937 A1 | 3/2003 | Ginn |
| 2003/0074037 A1 | 4/2003 | Moore et al. |
| 2003/0105503 A1 | 6/2003 | Marino |
| 2003/0109871 A1 | 6/2003 | Johnson et al. |
| 2003/0113906 A1 | 6/2003 | Sangha et al. |
| 2003/0130655 A1 | 7/2003 | Woloszko et al. |
| 2003/0130738 A1 | 7/2003 | Hovda et al. |
| 2003/0167021 A1 | 9/2003 | Shimm |
| 2003/0187368 A1 | 10/2003 | Sata et al. |
| 2003/0188749 A1 | 10/2003 | Nichols et al. |
| 2003/0208206 A1 | 11/2003 | Gitis et al. |
| 2003/0212400 A1 | 11/2003 | Bloemer et al. |
| 2003/0225412 A1 | 12/2003 | Shiraishi |
| 2003/0225415 A1 | 12/2003 | Richard |
| 2004/0006379 A1 | 1/2004 | Brett |
| 2004/0006391 A1 | 1/2004 | Reiley |
| 2004/0019359 A1 | 1/2004 | Worley et al. |
| 2004/0024399 A1 | 2/2004 | Sharps et al. |
| 2004/0030330 A1 | 2/2004 | Brassell et al. |
| 2004/0049179 A1 | 3/2004 | Francischelli et al. |
| 2004/0049208 A1 | 3/2004 | Hill et al. |
| 2004/0054368 A1 | 3/2004 | Truckai et al. |
| 2004/0059247 A1 | 3/2004 | Urmey |
| 2004/0064058 A1 | 4/2004 | McKay |
| 2004/0067000 A1 | 4/2004 | Bates et al. |
| 2004/0097927 A1 | 5/2004 | Yeung et al. |
| 2004/0102721 A1 | 5/2004 | McKinley |
| 2004/0106940 A1 | 6/2004 | Shaolian et al. |
| 2004/0111084 A1 | 6/2004 | Brett |
| 2004/0116977 A1 | 6/2004 | Finch et al. |
| 2004/0122433 A1 | 6/2004 | Loubens et al. |
| 2004/0122459 A1 | 6/2004 | Harp |
| 2004/0122482 A1 | 6/2004 | Tung et al. |
| 2004/0127893 A1 | 7/2004 | Hovda |
| 2004/0127963 A1 | 7/2004 | Uchida et al. |
| 2004/0133208 A1 | 7/2004 | Weikel et al. |
| 2004/0143165 A1 | 7/2004 | Alleyne |
| 2004/0143280 A1 | 7/2004 | Suddaby |
| 2004/0162609 A1 | 8/2004 | Hossainy et al. |
| 2004/0167444 A1 | 8/2004 | Laroya et al. |
| 2004/0167553 A1 | 8/2004 | Simpson et al. |
| 2004/0181150 A1 | 9/2004 | Evans et al. |
| 2004/0199159 A1 | 10/2004 | Lee et al. |
| 2004/0199166 A1 | 10/2004 | Schmieding et al. |
| 2004/0225233 A1 | 11/2004 | Frankowski |
| 2004/0260358 A1 | 12/2004 | Vaughan et al. |
| 2005/0027199 A1 | 2/2005 | Clarke |
| 2005/0033393 A1 | 2/2005 | Daglow |
| 2005/0049592 A1 | 3/2005 | Keith et al. |
| 2005/0060006 A1 | 3/2005 | Pflueger et al. |
| 2005/0075578 A1 | 4/2005 | Gharib et al. |
| 2005/0149034 A1 | 7/2005 | Assell et al. |
| 2005/0149035 A1 | 7/2005 | Pimenta et al. |
| 2005/0149154 A1 | 7/2005 | Cohen et al. |
| 2005/0171587 A1 | 8/2005 | Daglow et al. |
| 2005/0182454 A1 | 8/2005 | Gharib et al. |
| 2005/0187537 A1 | 8/2005 | Loeb et al. |
| 2005/0197661 A1 | 9/2005 | Carrison et al. |
| 2005/0203599 A1 | 9/2005 | Garabedian et al. |
| 2005/0209610 A1 | 9/2005 | Carrison |
| 2005/0209617 A1 | 9/2005 | Koven et al. |
| 2005/0209622 A1 | 9/2005 | Carrison |
| 2005/0216023 A1 | 9/2005 | Aram et al. |
| 2005/0222598 A1 | 10/2005 | Ho et al. |
| 2005/0222647 A1 | 10/2005 | Wahlstrand et al. |
| 2005/0234425 A1 | 10/2005 | Miller et al. |
| 2005/0256423 A1 | 11/2005 | Kirsner |
| 2005/0261692 A1 | 11/2005 | Carrison et al. |
| 2005/0267529 A1 | 12/2005 | Crockett et al. |
| 2005/0277942 A1 | 12/2005 | Kullas et al. |
| 2005/0283148 A1 | 12/2005 | Janssen et al. |
| 2005/0283204 A1 | 12/2005 | Buhlmann et al. |
| 2006/0004369 A1 | 1/2006 | Patel et al. |
| 2006/0015035 A1 | 1/2006 | Rock |
| 2006/0025702 A1 | 2/2006 | Sterrantino et al. |
| 2006/0025703 A1 | 2/2006 | Miles et al. |
| 2006/0025797 A1 | 2/2006 | Lock et al. |
| 2006/0030854 A1 | 2/2006 | Haines |
| 2006/0036211 A1 | 2/2006 | Solsberg et al. |
| 2006/0036271 A1 | 2/2006 | Schomer et al. |
| 2006/0036272 A1 | 2/2006 | Solsberg et al. |
| 2006/0058732 A1 | 3/2006 | Harp |
| 2006/0064101 A1 | 3/2006 | Arramon |
| 2006/0079919 A1 | 4/2006 | Harp |
| 2006/0085048 A1 | 4/2006 | Cory et al. |
| 2006/0085049 A1 | 4/2006 | Cory et al. |
| 2006/0089650 A1 | 4/2006 | Nolde |
| 2006/0089688 A1 | 4/2006 | Panescu |
| 2006/0095026 A1 | 5/2006 | Ricart et al. |
| 2006/0095028 A1 | 5/2006 | Bleich |
| 2006/0122458 A1 | 6/2006 | Bleich |
| 2006/0122620 A1 | 6/2006 | Kim |
| 2006/0122653 A1 | 6/2006 | Bradley et al. |
| 2006/0122654 A1 | 6/2006 | Bradley et al. |
| 2006/0129201 A1 | 6/2006 | Lee et al. |
| 2006/0142753 A1 | 6/2006 | Francischelli et al. |
| 2006/0149278 A1 | 7/2006 | Abdou |
| 2006/0161189 A1 | 7/2006 | Harp |
| 2006/0173374 A1 | 8/2006 | Neubardt et al. |
| 2006/0184175 A1 | 8/2006 | Schomer et al. |
| 2006/0195107 A1 | 8/2006 | Jones et al. |
| 2006/0200153 A1 | 9/2006 | Harp |
| 2006/0200154 A1 | 9/2006 | Harp |
| 2006/0200155 A1 | 9/2006 | Harp |
| 2006/0200219 A1 | 9/2006 | Thrope et al. |
| 2006/0206115 A1 | 9/2006 | Schomer et al. |
| 2006/0206117 A1 | 9/2006 | Harp |
| 2006/0206118 A1 | 9/2006 | Kim et al. |
| 2006/0206178 A1 | 9/2006 | Kim |
| 2006/0224060 A1 | 10/2006 | Garell et al. |
| 2006/0224078 A1 | 10/2006 | Hoey et al. |
| 2006/0235451 A1 | 10/2006 | Schomer et al. |
| 2006/0235452 A1 | 10/2006 | Schomer et al. |
| 2006/0264952 A1 | 11/2006 | Nelson et al. |
| 2006/0264994 A1 | 11/2006 | Schomer et al. |
| 2006/0276720 A1 | 12/2006 | McGinnis et al. |
| 2006/0276802 A1 | 12/2006 | Vresilovic et al. |
| 2006/0276836 A1 | 12/2006 | Bergin et al. |
| 2007/0010717 A1 | 1/2007 | Cragin |
| 2007/0016097 A1 | 1/2007 | Farquhar et al. |
| 2007/0016185 A1 | 1/2007 | Tullis et al. |
| 2007/0027464 A1 | 2/2007 | Way et al. |
| 2007/0027514 A1 | 2/2007 | Gerber |
| 2007/0049962 A1 | 3/2007 | Marino et al. |
| 2007/0055215 A1 | 3/2007 | Tran et al. |
| 2007/0055262 A1 | 3/2007 | Tomita et al. |
| 2007/0055263 A1 | 3/2007 | Way et al. |
| 2007/0073356 A1 | 3/2007 | Rooney et al. |
| 2007/0106219 A1 | 5/2007 | Grabinsky |
| 2007/0123890 A1 | 5/2007 | Way et al. |
| 2007/0162044 A1 | 7/2007 | Marino |
| 2007/0162061 A1 | 7/2007 | Way et al. |
| 2007/0162062 A1 | 7/2007 | Norton et al. |
| 2007/0166345 A1 | 7/2007 | Pavcnik et al. |
| 2007/0168007 A1 | 7/2007 | Kuzma et al. |

(56) References Cited

U.S. PATENT DOCUMENTS

| | | | |
|---|---|---|---|
| 2007/0198019 A1 | 8/2007 | Schomer et al. |
| 2007/0213583 A1 | 9/2007 | Kim et al. |
| 2007/0213584 A1 | 9/2007 | Kim et al. |
| 2007/0213734 A1 | 9/2007 | Bleich et al. |
| 2007/0213795 A1 | 9/2007 | Bradley et al. |
| 2007/0255162 A1 | 11/2007 | Abboud et al. |
| 2007/0255369 A1 | 11/2007 | Bonde et al. |
| 2007/0270795 A1 | 11/2007 | Francischelli et al. |
| 2007/0270865 A1 | 11/2007 | Arnin et al. |
| 2007/0276286 A1 | 11/2007 | Miller |
| 2007/0276390 A1 | 11/2007 | Solsberg et al. |
| 2007/0282217 A1 | 12/2007 | McGinnis et al. |
| 2007/0299403 A1 | 12/2007 | Crowe et al. |
| 2007/0299459 A1 | 12/2007 | Way et al. |
| 2008/0015582 A1 | 1/2008 | DiPoto et al. |
| 2008/0033465 A1 | 2/2008 | Schmitz et al. |
| 2008/0051812 A1 | 2/2008 | Schmitz et al. |
| 2008/0086034 A1 | 4/2008 | Schmitz et al. |
| 2008/0091227 A1 | 4/2008 | Schmitz et al. |
| 2008/0103504 A1 | 5/2008 | Schmitz et al. |
| 2008/0125621 A1 | 5/2008 | Gellman et al. |
| 2008/0125709 A1 | 5/2008 | Chang et al. |
| 2008/0146867 A1 | 6/2008 | Gellman et al. |
| 2008/0147084 A1 | 6/2008 | Bleich et al. |
| 2008/0161809 A1 | 7/2008 | Schmitz et al. |
| 2008/0197024 A1 | 8/2008 | Simpson et al. |
| 2008/0288005 A1 | 11/2008 | Jackson |
| 2008/0312660 A1 | 12/2008 | Bleich et al. |
| 2008/0319459 A1 | 12/2008 | Al-najjar |
| 2009/0018507 A1 | 1/2009 | Schmitz et al. |
| 2009/0018610 A1 | 1/2009 | Gharib et al. |
| 2009/0082763 A1 | 3/2009 | Quick et al. |
| 2009/0105604 A1 | 4/2009 | Bertagnoli et al. |
| 2009/0138056 A1 | 5/2009 | Anderson et al. |
| 2009/0143829 A1 | 6/2009 | Shluzas |
| 2009/0171381 A1 | 7/2009 | Schmitz et al. |
| 2009/0177112 A1 | 7/2009 | Gharib et al. |
| 2009/0182382 A1 | 7/2009 | Justis et al. |
| 2009/0209879 A1 | 8/2009 | Kaula et al. |
| 2010/0004654 A1 | 1/2010 | Schmitz et al. |
| 2010/0057087 A1 | 3/2010 | Cha |
| 2010/0094231 A1 | 4/2010 | Bleich et al. |
| 2010/0331883 A1 | 12/2010 | Schmitz et al. |
| 2011/0004207 A1 | 1/2011 | Wallace et al. |
| 2011/0060314 A1 | 3/2011 | Wallace et al. |
| 2011/0112539 A1 | 5/2011 | Wallace et al. |
| 2011/0160731 A1 | 6/2011 | Bleich et al. |
| 2011/0160772 A1 | 6/2011 | Arcenio et al. |
| 2011/0190772 A1 | 8/2011 | Saadat et al. |
| 2011/0224709 A1 | 9/2011 | Bleich |
| 2011/0224710 A1 | 9/2011 | Bleich |
| 2012/0016368 A1 | 1/2012 | Bleich et al. |
| 2012/0065639 A1 | 3/2012 | Schmitz et al. |
| 2012/0123294 A1 | 5/2012 | Sun et al. |
| 2012/0143206 A1 | 6/2012 | Wallace et al. |
| 2012/0191003 A1 | 7/2012 | Garabedian et al. |
| 2012/0239041 A1 | 9/2012 | Bleich et al. |
| 2013/0012831 A1 | 1/2013 | Schmitz et al. |
| 2013/0053853 A1 | 2/2013 | Schmitz et al. |
| 2013/0150855 A1 | 6/2013 | Bleich et al. |
| 2013/0150856 A1 | 6/2013 | Mimran et al. |
| 2013/0172895 A1 | 7/2013 | Wallace et al. |

FOREIGN PATENT DOCUMENTS

| | | |
|---|---|---|
| DE | 3209403 A1 | 9/1983 |
| DE | 4036804 A1 | 5/1992 |
| EP | 359883 A1 | 3/1990 |
| EP | 1304080 A2 | 4/2003 |
| EP | 1340467 A2 | 9/2003 |
| EP | 1207794 B1 | 5/2004 |
| EP | 1315463 B1 | 5/2005 |
| EP | 1611851 A1 | 1/2006 |
| EP | 1006885 B1 | 9/2006 |
| FR | 2706309 | 12/1994 |
| GB | 1460837 A | 1/1977 |
| JP | 2960140 B2 | 10/1999 |
| JP | 23116868 | 4/2003 |
| JP | 24065380 A2 | 3/2004 |
| RU | 2107459 | 3/1998 |
| WO | WO92/22259 A2 | 12/1992 |
| WO | WO96/22057 A1 | 7/1996 |
| WO | WO97/14362 A1 | 4/1997 |
| WO | WO97/34536 A2 | 9/1997 |
| WO | WO99/18866 A1 | 4/1999 |
| WO | WO99/21500 A1 | 5/1999 |
| WO | WO00/67651 A1 | 11/2000 |
| WO | WO01/08571 A1 | 2/2001 |
| WO | WO01/62168 A2 | 8/2001 |
| WO | WO02/07901 A1 | 1/2002 |
| WO | WO02/34120 A2 | 5/2002 |
| WO | WO02/076311 A2 | 10/2002 |
| WO | WO03/026482 A2 | 4/2003 |
| WO | WO03/066147 A1 | 8/2003 |
| WO | WO2004/002331 A1 | 1/2004 |
| WO | WO2004/028351 A2 | 4/2004 |
| WO | WO2004/043272 A1 | 5/2004 |
| WO | WO2004/056267 A1 | 7/2004 |
| WO | WO2004/078066 A2 | 9/2004 |
| WO | WO2004/080316 A1 | 9/2004 |
| WO | WO2004/096080 A2 | 11/2004 |
| WO | WO2005/009300 A1 | 2/2005 |
| WO | WO2005/057467 A2 | 6/2005 |
| WO | WO2005/077282 A1 | 8/2005 |
| WO | WO2005/089433 A2 | 9/2005 |
| WO | WO2006/009705 A2 | 1/2006 |
| WO | WO2006/015302 A1 | 2/2006 |
| WO | WO2006/017507 A2 | 2/2006 |
| WO | WO2006/039279 A2 | 4/2006 |
| WO | WO2006/042206 A2 | 4/2006 |
| WO | WO2006/044727 A2 | 4/2006 |
| WO | WO2006/047598 A1 | 5/2006 |
| WO | WO2006/058079 A2 | 6/2006 |
| WO | WO2006/058195 A2 | 6/2006 |
| WO | WO2006/062555 A2 | 6/2006 |
| WO | WO2006/086241 A2 | 8/2006 |
| WO | WO2006/099285 A2 | 9/2006 |
| WO | WO2006/102085 A2 | 9/2006 |
| WO | WO2007/008709 A2 | 1/2007 |
| WO | WO2007/021588 A1 | 2/2007 |
| WO | WO2007/022194 A2 | 2/2007 |
| WO | WO2007/059343 A2 | 2/2007 |
| WO | WO2007/067632 A2 | 6/2007 |
| WO | WO2008/008898 A2 | 1/2008 |

OTHER PUBLICATIONS

Schmitz et al.; U.S. Appl. No. 14/064,085 entitled "Access and Tissue Modification Systems and Methods," filed Oct. 25, 2013.

Schmitz et al.; U.S. Appl. No. 14/082,052 entitled "Flexible Tissue Removal Devices and Methods," filed Nov. 15, 2013.

Bleich et al.; U.S. Appl. No. 14/180,221 entitled "Flexible tissue rasp," filed Feb. 13, 2014.

Abdel-Wanis et al., "Tumor growth potential after tumoral and instrumental contamination: an in-vivo comparative study of T-saw, Gigli saw, and scalpel," Journal of orthopaedic science, Sep. 2001, vol. 6, 424-429.

Barer Malvin, "Instrument to Enhance Passage of the Gigli Saw," Journal of Pediatric Orthopedics, Raven Press, New York, Nov. 1984, 4:762-763.

Baumgart et al., "Indikation and Technik der Knochendurchtrennung," Der Chirurg, Nov. 1998, vol. 69:1188-1196. (in German with Eng Summary).

Bohinski et al., "Novel use of a threadwire saw for high sacral amputation," Journal of neurosurgery: Spine, Jul. 2005, vol. 3(1): 71R78.

Brunori et al., "Celebrating the centennial (1894-1994): Leonardo Gigli and his wire saw," J. Neurosurg, Jun. 1995, 82(6):1086-1090.

Burrows, Harold, "Surgical instruments and appliances used in operations," Faber and Faber, London, Jan. 1937, total pp. 4.

Codman Laminectomy Shaver (a Johnson & Johnson company www.codman.com) catalogue, pp. 416-431, [online] Retrieved from the

(56) References Cited

OTHER PUBLICATIONS internet: <URL: http:llwww.codman.com/PDFs/Catalog_04_R.pdf>; date of publication unknown; available to applicants at least as of Nov. 22, 2006.
Dammann, Gordon, Pictorial Encyclopedia of Civil War Medical Instruments and Equipment, Pictorial Histories Publishing Company, Missoula, Montana, Apr. 1, 1983, Total pp. 2.
Edwards et al; "T-Saw Laminoplasty for the Management of Cervical Spondylotic Myelopathy," Spine, Lippincott Williams & Wilkins, Inc., Jul. 15, 2000, vol. 25(14): 1788R1794.
Ellman Int. Disc-FX System Accessories K052241 [online] Retrieved from the Internet: <URL: http://www.ellman.com/medical/>; 1 page; date of publication unknown; available to applicants at least as of Nov. 22, 2006.
Eralp et al., "A comparison of two osteotomy techniques for tibial lengthening," Archives of orthopaedic and trauma surgery, Jun. 2004, vol. 124: pp. 298-300.
Fessler Richard G, "Minimally Invasive Microendoscopic Decompressive Laminotomy for Lumbar Stenosis," American Association of Neurological Surgeons, 2006, Online CME course, 26 pages total, [Retrieved on Jun. 29, 2006 from the Internet http://www.aans.emedtrain.com/lumbar_stenosis/lumbarStenosis.swf.
Fujita et al., "Chordoma in the Cervical Spine Managed with En Bloc Excision," Spine, Lippincott Williams & Wilkins, Inc., Sep. 1, 1999, 24 (17):1848-1851.
Goel, Atul, "Neurosurgical forum, Supraorbital Craniotomy," Journal of Neurosurgery, Oct. 1994, vol. 81, 642-643.
Gore Smoother User Manual, W. L. Gore & Associates, Inc. Flagstaff, AZ, Dec. 1999,Total pp. 3.
Hara et al., "En Bloc Laminoplasty Performed with Threadwire Saw: Technical Note," Neurosurgery, Jan. 2001, vol. 48, No. 1, pp. 235-239.
Hata et al; "A less invasive surgery for rotator cuff tear: Mini-open repair," Journal of Shoulder and Elbow Surgery, Jan. 2001, vol. 10 No. 1, 11-16.
Herkowitz, "The Cervical Spine Surgery Atlas", 2004, Lippincott Williams & Wilkins; 2nd Edition; pp. 203-206, & 208; Dec. 2003.
Honl et al; "The Use of Water-Jetting Technology in Prostheses Revision Surgery . . . ," J. Biomed Mater Res (Applied Biomaterials), John Wiley & Sons, Inc, 2000, 53(6): 781-790 (year of pub. is sufficiently earlier than effective U.S. filing date & any foreign priority date).
Integra Ruggles TM Kerrison Rongeurs [online]; Retrieved from the internet: <URL: http://www.integra-ls.com/products!? product=22> on Oct. 17, 2006; 2 pages.
Jun, Byung-Yoon, "Posterior Lumbar Interbody Fusion With Restoration of Lamina and Facet Fusion," Spine, Lippincott Williams & Wilkins, Inc., Apr. 15, 2000, vol. 25, No. 8, pp. 917-922.
Kawahara et al., "Recapping T-Saw Laminoplasty for Spinal Cord Tumors," Spine, Jul. 1, 1999, vol. 24 No. 13, pp. 1363-1370.
Martin-Benlloch et al., "Expansive Laminoplasty as a Method for Managing Cervical Multilevel Spondylotic Myelopathy," Spine, Lippincott Williams & Wilkins, Inc., Apr. 1, 2003, vol. 28, No. 7, pp. 680-684.
Miyamoto et al., "Kyphectomy Using a Surgical Threadwire (T-saw) for Kyphotic Deformity in a Child With Myelomeningocele," Spine, Lippincott Williams & Wilkins, Inc., May 15, 2003, vol. 28, No. 10, pp. E187-E190.
Mopec Bone-Cutting tool, Product brochure; Dec. 15, 2005; Total pp. 4.
Nakagiri et al., "Thoracoscopic Rib Resection Using a Gigli Saw," The Annals of Thoracic Surgery, Aug. 2005, vol. 80, pp. 755-756.
Osaka et al., "Clinical significance of a wide excision policy for sacrococcygeal chordoma," J Cancer Res Clin Oncol, Dec. 16, 2005, Total pp. 6.
Paktiss et al., "Afghan Percutaneous Osteotomy," Journal of Pediatric Orthopaedics, Raven Press Ltd, New York, Jul.-Aug. 1993, vol. 13, No. 4, 531-533.
Paley et al., "Percutaneous Osteotomies," Orthopedic Clinics of North America, Oct. 1991, vol. 22, No. 4, pp. 613-624.
Pancoast, Joseph, "A Treatise on Operative Surgery," Carey and Hart, Philadelphia, (year of publication is sufficiently earlier than the effective U.S. filing date and any foreign priority date) 1844, Total pp. 11.
Park et al; "Cases of the Excision of Carious Joints," John Scrymgeour, Glasgow, (year of publication is sufficiently earlier than the effective U.S. filing date and any foreign priority date) 1806, Total pp. 6.
Peavy et al., "Comparison of Cortical Bone Ablations by Using Infrared Laser Wavelengths 2.9 to 9.2 μm, Lasers in Surgery and Medicine," (year of publication is sufficiently earlier than the effective U.S. filing date and any foreign priority date) 1999, vol. 26, pp. 421-434.
Peltier, Leonard Orthopedics: A History and Iconography, Norman Publishing, San Francisco, Feb. 1, 1993, Total pp. 3.
Reckling Frederick, "Modified Stethoscope Earpiece Makes Excellent Gigli Saw Guide," J Bone and Joint Surgery Am, Dec. 1972, 54-A(8), 1787-1788.
Rutkow, Ira, "Surgery: An Illustrated History," Mosby'Year Book, Inc., St. Louis, Oct. 1, 1993, Total pp. 4.
Schwieger et al., "Abrasive Water Jet Cutting as a New Procedure for Cutting Cancellous Bone'In Vitro Testing in Comparison with the Oscillating Saw," Wiley Interscience, www.interscience,wiley.com, Sep. 20, 2004, pp. 223-228.
Sen et al., The reliability of percutaneous osteotomy with the Gigli saw technique in the proximal tibia;36(2); pp. 136-140; (year of publication is sufficiently earlier than the effective U.S. filing date and any foreign priority date) 2002, (Turkish w/ Eng Trans.)
Shiraishi et al., "Results of Skip Laminectomy—Minimum 2-Year Follow-up Study Compared With Open-Door Laminoplasty," Spine, Lippincott Williams & Wilkins, Inc., Dec. 15, 2003, vol. 28, No. 24, pp. 2667-2672.
Shiraishi T., "A new technique for exposure of the cervical spine laminae. Technical note," Journal of neurosurgery. Spine, Jan. 2002, vol. 96(1), 122-126.
Shiraishi T., Skip laminectomy—a new treatment for cervical spondylotic myelopathy, preserving bilateral muscular attachments to the spinous processes: a preliminary report, Spine, Mar.-Apr. 2002, vol. 2(2), pp. 108-115.
Skippen et al., "The Chain Saw R A Scottish Invention," Scottish Medical Journal, May 2004, vol. 49(2), 72-75.
Stevens et al., "Calvarial Bone Graft Harvest Using the Gigli Saw," Journal of Oral and Maxillofacial Surgery, Jun. 1998, vol. 56(6): 798-799.
Takada et al., "Unusual Metastasis to the Cauda Equina From Renal Cell Carcinoma," Spine, Lippincott Williams & Wilkins, Inc; Mar. 15, 2003, vol. 28 No. 6, pp. E114-E117.
Tomita et al., "Expansive Midline T-Saw Laminoplasty (Modified Spinour Process-Splitting) for the Management of Cervical Myelopathy," Spine, Lippincott Williams & Wilkins, Inc; Jan. 1, 1998, 23(1): 32-37.
Tomita et al., "The Threadwire Saw: a New Device for Cutting Bone," The Journal of Bone and Joint Surgery, Dec. 1996, vol. 78(12): 1915-1917.
Tomita et al., "The Use of the T-Saw for Expansive Midline laminoplasty in the Treatment of Cervical Myelopathy," Orthopedics and Traumatology, vol. 10, No. 3, pp. 169-178, Sep. 2002.
Tomita et al., "Total en bloc spondylectomy and circumspinal decompression for solitary spinal metastasis," Paraplegia, Jan. 1994, 32(1):36-46.
Tomita K. et al., "Total en bloc spondylectomy for solitary spinal metastases," International Orthopaedics (SICOT), Oct. 1994, 18(5): 291-298.
Truax, Charles, "The Mechanics of Surgery," Chicago, IL; (year of publication is sufficiently earlier than the effective U.S. filing date and any foreign priority date) 1899, Total pp. 3.
US Surgical Kerrison Spinal Rongeur K943116 [online] Retrieved from the internet: <URL: http://www.ussurg.com/uss/index.html> Nov. 22, 2006; 1 page.
Wilkins, Robert H, "Neurosurgical Classics," Johnson Reprint Corporation, New York, (year of publication is sufficiently earlier than the effective U.S. filing and any foreign priority date) 1965, pp. 377-382.

(56) References Cited

OTHER PUBLICATIONS

Zeppelin Laminectomy Rongeur K901372, [online] Retrieved from the Internet: <URL: http://www.zeppelin-medical.com/download/instruments.pdf>, Oct. 24, 2006; 1 page.

Saadat et al.; U.S. Appl. No. 13/913,801 entitled "Powered Tissue Modification Devices and Methods," filed Jun. 10, 2013.

Schmitz et al.; U.S. Appl. No. 14/195,197 entitled "Tissue modification devices," filed Mar. 3, 2014.

Leguidleguid et al.; U.S. Appl. No. 14/209,418 entitled "Tissue Modification Devices," filed Mar. 13, 2014.

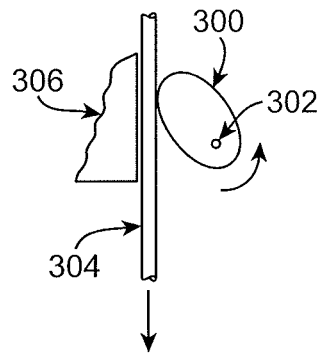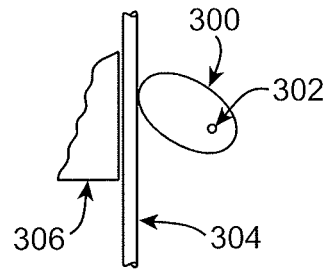
FIG. 18A  FIG. 18B
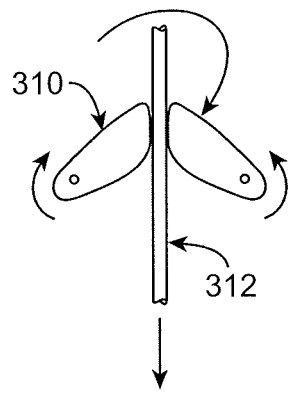
FIG. 19
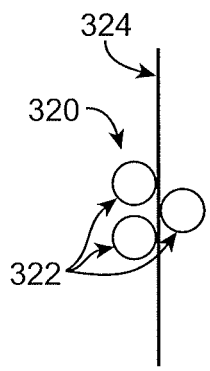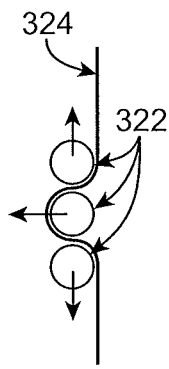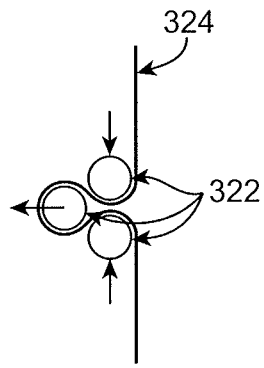
FIG. 20A  FIG. 20B  FIG. 20C

TISSUE ACCESS GUIDEWIRE SYSTEM AND METHOD

CROSS-REFERENCE TO RELATED APPLICATIONS

This application is a divisional of U.S. patent application Ser. No. 12/917,253, filed Nov. 1, 2010, entitled "TISSUE ACCESS GUIDEWIRE SYSTEM AND METHOD," Publication No. US-2011-0046613-A1, which is a continuation of U.S. patent application Ser. No. 11/468,247, filed Aug. 29, 2006, entitled "TISSUE ACCESS GUIDEWIRE SYSTEM AND METHOD," now U.S. Pat. No. 7,857,813, each of which is herein incorporated by reference in its entirety.

The present application is related to U.S. patent application Ser. No. 11/468,252, filed Aug. 29, 2006, entitled "TISSUE ACCESS GUIDEWIRE SYSTEM AND METHOD," Publication No. US-2008-0086034-A1, which is herein incorporated by reference in its entirety.

INCORPORATION BY REFERENCE

All publications and patent applications mentioned in this specification are herein incorporated by reference in their entirety to the same extent as if each individual publication or patent application was specifically and individually indicated to be incorporated by reference.

BACKGROUND OF THE INVENTION

The present invention relates generally to medical/surgical devices and methods. More specifically, the present invention relates to a guidewire system and method for advancing one or more surgical devices between tissues in a patient.

In recent years, less invasive (or "minimally invasive") surgical techniques have become increasingly more popular, as physicians, patients and medical device innovators have sought to achieve similar or improved outcomes, relative to conventional surgery, while reducing the trauma, recovery time and side effects typically associated with conventional surgery. Developing less invasive surgical methods and devices, however, can pose many challenges. For example, some challenges of less invasive techniques include working in a smaller operating field, working with smaller devices, and trying to operate with reduced or even no direct visualization of the structure (or structures) being treated. These challenges are compounded by the fact that target tissues to be modified often reside very close to one or more vital, non-target tissues, which the surgeon hopes not to damage. One of the initial obstacles in any given minimally invasive procedure, therefore, is positioning a minimally invasive surgical device in a desired location within the patient to perform the procedure on one or more target tissues, while avoiding damage to nearby non-target tissues.

Examples of less invasive surgical procedures include laparoscopic procedures, arthroscopic procedures, and minimally invasive approaches to spinal surgery, such as a number of less invasive intervertebral disc removal, repair and replacement techniques. One area of spinal surgery in which a number of less invasive techniques have been developed is the treatment of spinal stenosis. Spinal stenosis occurs when neural and/or neurovascular tissue in the spine becomes impinged by one or more structures pressing against them, causing one or more symptoms. This impingement of tissue may occur in one or more of several different areas in the spine, such as in the central spinal canal, or more commonly in the lateral recesses of the spinal canal and/or one or more intervertebral foramina.

FIGS. 1-3 show various partial views of the lower (lumbar) region of the spine. FIG. 1 shows an approximate top view of a vertebra with the cauda equina (the bundle of nerves that extends from the base of the spinal cord through the central spinal canal) shown in cross section and two nerve roots exiting the central spinal canal and extending through intervertebral foramina on either side of the vertebra. The spinal cord and cauda equina run vertically along the spine through the central spinal canal, while nerve roots branch off of the spinal cord and cauda equina between adjacent vertebrae and extend through the intervertebral foramina. Intervertebral foramina may also be seen in FIGS. 2 and 3, and nerves extending through the foramina may be seen in FIG. 2.

One common cause of spinal stenosis is buckling and thickening of the ligamentum flavum (one of the ligaments attached to and connecting the vertebrae), as shown in FIG. 1. (Normal ligamentum flavum is shown in cross section in FIG. 3) Buckling or thickening of the ligamentum flavum may impinge on one or more neurovascular structures, dorsal root ganglia, nerve roots and/or the spinal cord itself. Another common cause of neural and neurovascular impingement in the spine is hypertrophy of one or more facet joints (or "zygopophaseal joints"), which provide articulation between adjacent vertebrae. (Two vertebral facet superior articular processes are shown in FIG. 1. Each superior articular process articulates with an inferior articular process of an adjacent vertebra to form a zygopophaseal joint. Such a joint is labeled in FIG. 3.) Other causes of spinal stenosis include formation of osteophytes (or "bone spurs") on vertebrae, spondylolisthesis (sliding of one vertebra relative to an adjacent vertebra), facet joint synovial cysts, and collapse, bulging or herniation of an intervertebral disc into the central spinal canal. Disc, bone, ligament or other tissue may impinge on the spinal cord, the cauda equina, branching spinal nerve roots and/or blood vessels in the spine to cause loss of function, ischemia and even permanent damage of neural or neurovascular tissue. In a patient, this may manifest as pain, impaired sensation and/or loss of strength or mobility.

In the United States, spinal stenosis occurs with an incidence of between 4% and 6% of adults aged 50 and older and is the most frequent reason cited for back surgery in patients aged 60 and older. Conservative approaches to the treatment of symptoms of spinal stenosis include systemic medications and physical therapy. Epidural steroid injections may also be utilized, but they do not provide long lasting benefits. When these approaches are inadequate, current treatment for spinal stenosis is generally limited to invasive surgical procedures to remove ligament, cartilage, bone spurs, synovial cysts, cartilage, and bone to provide increased room for neural and neurovascular tissue. The standard surgical procedure for spinal stenosis treatment includes laminectomy (complete removal of the lamina (see FIGS. 1 and 2) of one or more vertebrae) or laminotomy (partial removal of the lamina), followed by removal (or "resection") of the ligamentum flavum. In addition, the surgery often includes partial or occasionally complete facetectomy (removal of all or part of one or more facet joints). In cases where a bulging intervertebral disc contributes to neural impingement, disc material may be removed surgically in a discectomy procedure.

Removal of vertebral bone, as occurs in laminectomy and facetectomy, often leaves the effected area of the spine very unstable, leading to a need for an additional highly invasive fusion procedure that puts extra demands on the patient's vertebrae and limits the patient's ability to move. In a spinal fusion procedure, the vertebrae are attached together with some kind of support mechanism to prevent them from moving relative to one another and to allow adjacent vertebral bones to fuse together. Unfortunately, a surgical spine fusion results in a loss of ability to move the fused section of the back, diminishing the patient's range of motion and causing stress on the discs and facet joints of adjacent vertebral segments. Such stress on adjacent vertebrae often leads to further dysfunction of the spine, back pain, lower leg weakness or pain, and/or other symptoms. Furthermore, using current surgical techniques, gaining sufficient access to the spine to perform a laminectomy, facetectomy and spinal fusion requires dissecting through a wide incision on the back and typically causes extensive muscle damage, leading to significant post-operative pain and lengthy rehabilitation. Discectomy procedures require entering through an incision in the patient's abdomen and navigating through the abdominal anatomy to arrive at the spine. Thus, while laminectomy, facetectomy, discectomy, and spinal fusion frequently improve symptoms of neural and neurovascular impingement in the short term, these procedures are highly invasive, diminish spinal function, drastically disrupt normal anatomy, and increase long-term morbidity above levels seen in untreated patients. Although a number of less invasive techniques and devices for spinal stenosis surgery have been developed, these techniques still typically require removal of significant amounts of vertebral bone and, thus, typically require spinal fusion.

Therefore, it would be desirable to have less invasive surgical methods and systems for treating spinal stenosis. For example, it would be desirable to have devices or systems for positioning a less invasive device in a patient for performing a less invasive procedure. Ideally, such systems and devices would be less invasive than currently available techniques and thus prevent damage to non-target vertebral bone and neural and neurovascular structures. Also ideally, such systems and devices would also be usable (or adaptable for use) in positioning a surgical device in parts of the body other than the spine, such as in joints for performing various arthroscopic surgical procedures, between a cancerous tumor and adjacent tissues for performing a tumor resection, and the like. At least some of these objectives will be met by the present invention.

SUMMARY OF THE INVENTION

In one aspect of the present invention, a method for guiding at least a portion of a surgical device to a desired position between two tissues in a patient's body may involve: advancing a distal end of a guidewire into the patient's body, between two tissues, and out of the body, while maintaining a proximal end of the guidewire outside the body; coupling the proximal end of the guidewire with at least one coupling member on or near a distal end of a surgical device; and pulling the distal end of the guidewire to guide at least a portion of the surgical device to a desired position between the two tissues. In some embodiments, the distal end of the guidewire may be advanced through a guidewire introducer device having at least one lumen. Alternatively, the distal end of the guidewire may be advanced through a guidewire lumen of the surgical device. In some embodiments, the distal end of the guidewire may be sharpened, to facilitate its passage through tissue. For example, in various embodiments, the distal end may be passed through tissue of the patient's body by pushing and turning a guidewire having a drill-shaped or corkscrew-shaped tip. In some embodiments, the guidewire is advanced into an epidural space and through an intervertebral foramen of the patient's spine.

In one embodiment, the guidewire and coupling member may be coupled by fitting a shaped proximal end of the guidewire into the at least one coupling member at or near the distal end of the surgical device. Optionally, coupling may further involve rotating at least one of the guidewire and the surgical device to lock the shaped proximal end into the coupling member(s). In some embodiments the guidewire and surgical device may be removably coupled, while in alternative embodiments, they may be permanently coupled.

In some embodiments, the method may further include performing a surgical procedure on at least one of the two tissues, using the surgical device, removing the surgical device from the body. Such a method may optionally further involve detaching the guidewire from the surgical device, coupling the proximal end of the guidewire with a coupling member on or near a distal end of a second surgical device, pulling the distal end of the guidewire to guide at least a portion of the second surgical device to a desired position between the two tissues, and performing a surgical procedure on at least one of the two tissues, using the second surgical device. These steps may be repeated, in various embodiments, with as many surgical devices as desired. In some embodiments, the surgical procedure may be performed with the guidewire attached to the surgical device. The method may further include pulling the distal end of the guidewire and a proximal end of the surgical device, to urge an active portion of the surgical device against a target tissue. Typically, the surgical procedure may be performed on one or more target tissues while one or more non-target tissues are protected from harm by at least one atraumatic portion of the surgical device.

In another aspect of the present invention, a method for performing a procedure on a target tissue in a patient's body may involve: coupling a proximal end of a guidewire with at least one coupling member on or near a distal end of a surgical device; pulling a distal end of the guidewire to guide at least a portion of the surgical device to a desired position between the two tissues, such that an active portion of the surgical device faces target tissue and an atraumatic portion of the surgical device faces non-target tissue; and performing a procedure on the target tissue, using the surgical device. In some embodiments, the surgical device may comprise a tissue modification device, and performing the procedure may comprise modifying the target tissue with the tissue modification device coupled with the guidewire. Alternatively, the surgical device may comprise a tissue access device, and the method may further involve, before the performing step, advancing a tissue modification device through the tissue access device. Some embodiments of the method may further involve pulling on the distal end of the guidewire and a proximal end of the surgical device to urge the active portion of the surgical device against the target tissue.

In another aspect of the present invention, a system for guiding a surgical device to a desired position between two different tissues in a human body, the two tissues having a natural tissue interface therebetween, may include a guidewire having a first end and a second end with an axis therebetween and a first coupling member and a surgical device having a proximal end and a distal end with a second coupling member disposed at or near the distal end, the first and second coupling members being separable. In one embodiment, one of the coupling members may comprise a receiving coupling member configured for receiving the other coupling member so as to allow the surgical device to be pulled distally along the natural tissue interface by axial tension of the guidewire. In one embodiment, the other coupling member may comprise a small profile portion extending from a shaped element, the shaped element having a profile larger than the small profile portion, the receiving coupling member comprising a channel for receiving the shaped element and a slot for receiving the small profile portion so that the shaped element is captured by the receiving coupling member when the shaped portion is inserted into the channel and the guidewire pulls the surgical device distally along the natural tissue interface. Optionally, the other coupling member may be disposed on the guidewire, and the small profile portion may comprise a portion of the shaft of the guidewire, wherein the channel is angularly offset from the axis of the guidewire when the guidewire pulls the surgical device distally so that the coupling members are releasably affixed together by inserting the shaped element along the channel and rotating the guidewire about a rotation axis extending laterally from the axis of the guidewire.

In some embodiments, the distal end of the surgical device may be configured to effect blunt dissection of the natural tissue interface between the first and second tissues. Also in some embodiments, the first coupling member may comprise a shaped element at the first end for coupling with the at least one guidewire coupling member; and the second end may comprise a sharpened distal tip to facilitate passage through of the guidewire through tissue. For example, the shaped element may have a shape such as but not limited to that of a ball, a cylinder, a teardrop, a cube, a pyramid, a diamond or a hook. The sharpened distal tip, in various embodiments, may have a shape such as but not limited to that of pointed, beveled, double-beveled, drill-tip shaped or corkscrew. In some emboments, the receiving coupling member may comprise at least one movable part configured to move from an open position to a closed position to hold the guidewire. In some embodiments, the surgical device may comprise a tissue access device, and the system may optionally further include at least one additional surgical device configured to pass at least partway through the tissue access device to help perform a procedure on target tissue. Optionally, the system may also include a guidewire handle for coupling with the guidewire outside the body to facilitate pulling the guidewire.

In another aspect of the present invention, a tissue access device for providing access to target tissue in a patient's body while protecting non-target tissue may include: a shaft having a proximal portion, a distal portion, and at least one lumen passing longitudinally through at least the proximal portion to allow passage of at least one additional device therethrough; at least one side-facing aperture in at least one of the proximal and distal shaft portions, through which the at least one additional device may be exposed to the target tissue; and a guidewire coupling member on the distal portion of the shaft for coupling with a guidewire to allow the tissue access device to be pulled behind the guidewire to position its distal portion between the target and non-target tissues with the aperture facing the target tissue.

In various embodiments, part of the shaft may be rigid and part of the shaft may be flexible, or the entire shaft may be either rigid or flexible. For example, in some embodiments the proximal portion may be rigid and the distal portion may be at least partially flexible. Optionally, a flexible distal portion may be steerable from a relatively straight configuration to a curved configuration, and the device may further include at least one steering actuator extending from the proximal portion to the distal portion. In some embodiments, the lumen may pass through both the proximal and distal portions, and the aperture may be located in the distal portion. Alternatively, the lumen may pass through only the proximal portion, and the aperture may be positioned in a distal region of the proximal portion, such that when part of the additional device passes through the aperture, it is located above the distal portion of the shaft.

Optionally, the device may further include at least one electrode coupled with at least one surface of the distal portion of the shaft and configured to stimulate nerve tissue. In some embodiments, the guidewire coupling member may be configured to removably couple with a shaped member at one end of a guidewire. Optionally, the device may further include a handle coupled with a proximal end of the proximal portion.

In another aspect of the present invention, a system for providing access to target tissue in a patient's body while protecting non-target tissue may include a tissue access device and a guidewire configured to couple with a guidewire coupling member on the access device. The access device may include: a shaft having a proximal portion, a distal portion, and at least one lumen passing longitudinally through at least the proximal portion to allow passage of at least one additional device therethrough; at least one side-facing aperture in at least one of the proximal and distal shaft portions, through which the at least one additional device may be exposed to the target tissue; and a guidewire coupling member on the distal portion of the shaft for coupling with a guidewire to allow the tissue access device to be pulled behind the guidewire to position its distal portion between the target and non-target tissues with the aperture facing the target tissue.

In some embodiments, the guidewire may have a sharp distal tip and a shaped member on a proximal tip for coupling with the guidewire coupling member. Optionally, the system may further include at least one additional device configured to pass through the tissue access device to expose at least an active portion of the additional device through the side-facing aperture. Examples of such an additional device include, but are not limited to, tissue cutting devices, tissue ablation devices, tissue abrasion devices, other tissue removal devices, other tissue modification devices, tissue storage devices, tissue transport devices, drug delivery devices, implant delivery devices, material delivery devices, visualization devices and diagnostic devices.

Some embodiments of the system may further include one or more anchoring devices for coupling the shaft of the tissue access device with a structure inside and/or outside the patient to stabilize the tissue access device. In some embodiments, the tissue access device may further include a handle coupled with a proximal end of the proximal shaft portion. The system may also optionally include a guidewire handle for coupling with the guidewire outside the patient to facilitate pulling on the guidewire to apply tensioning force.

In another aspect of the present invention, a method for providing access to target tissue in a patient's body while protecting non-target tissue may involve: passing a guidewire between the target and non-target tissues; coupling the guidewire with a guidewire coupling member on a distal portion of a tissue access device; and pulling the guidewire through the patient's body to pull the distal portion of the tissue access device between the target and non-target tissues such that a side-facing aperture of the tissue access device faces the target tissue. When the distal portion of the access device is positioned between the target and non-target tissues, a proximal portion of the device may extend outside the patient, such that at least one tissue modification device may be passed through at least the proximal portion to expose one or more tissue modifying members through the side-facing aperture.

Optionally, the method may further include identifying at least the non-target tissue before passing the guidewire. Also optionally, the method may further involve: advancing a first tissue modification device through the tissue access device to expose at least one tissue modification member of the device through the side-facing aperture of the access device; pulling the guidewire and at least one of the tissue access device and the tissue modification device to urge the at least one tissue modification member against the target tissue; and activating the tissue modification member(s) to modify the target tissue while protecting the non-target tissue with the distal portion of the access device. In some embodiments, the method may further involve: removing the first tissue modification device from the patient's body, through the access device; advancing a second tissue modification device through the tissue access device to expose at least one tissue modification member of the device through the side-facing aperture of the second access device; pulling the guidewire and at least one of the tissue access device and the second tissue modification device to urge the at least one tissue modification member against the target tissue; and activating the tissue modification member(s) to modify the target tissue. In some embodiments, activating the tissue modification member(s) may involve actuating at least one actuation member on a handle of the tissue access device. In some embodiments, the method may further involve coupling the tissue access device with a structure inside and/or outside the patient, using at least one anchoring device, to stabilize the access device. The method may further involve activating at least one electrode on the distal portion of the tissue access device to confirm placement of the distal portion between the target and non-target tissues.

These and other aspects and embodiments are described more fully below in the Detailed Description, with reference to the attached Drawings.

BRIEF DESCRIPTION OF THE DRAWINGS

FIGS. 18A and 18B are top views of a single-cam guidewire coupling member, according to an alternative embodiment of the present invention;

FIG. 19 is a top view of a double-cam guidewire coupling member, according to an alternative embodiment of the present invention;

FIGS. 20A-20C are top views of a movable-piece guidewire coupling member, according to an alternative embodiment of the present invention;

DETAILED DESCRIPTION OF THE INVENTION

Various embodiments of a guidewire system and method for positioning one or more surgical devices in a patient are provided. Although the following description and accompanying drawing figures generally focus on positioning various surgical devices in a spine, in alternative embodiments, guidewire systems and methods of the present invention may be used to position any of a number of devices in other anatomical locations in a patient's body.

Figure 1:
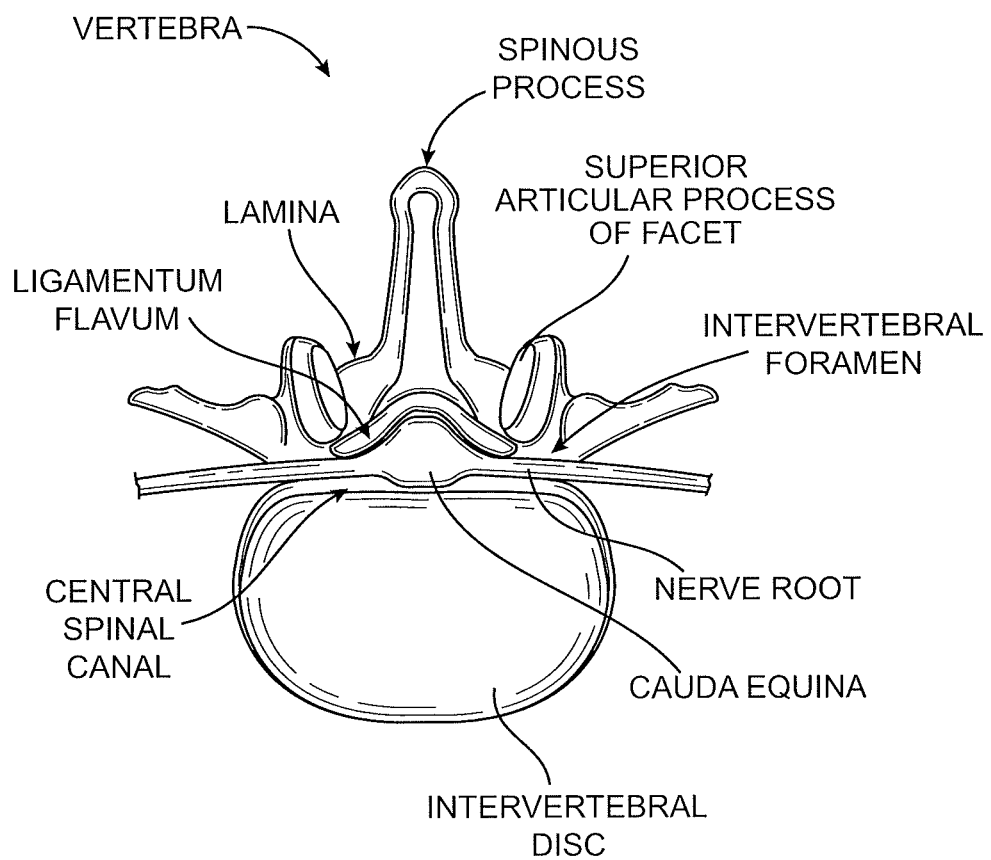
FIG. 1 is cross-sectional view of a spine, showing a top view of a lumbar vertebra, a cross-sectional view of the cauda equina, and two exiting nerve roots.
Figure 2:
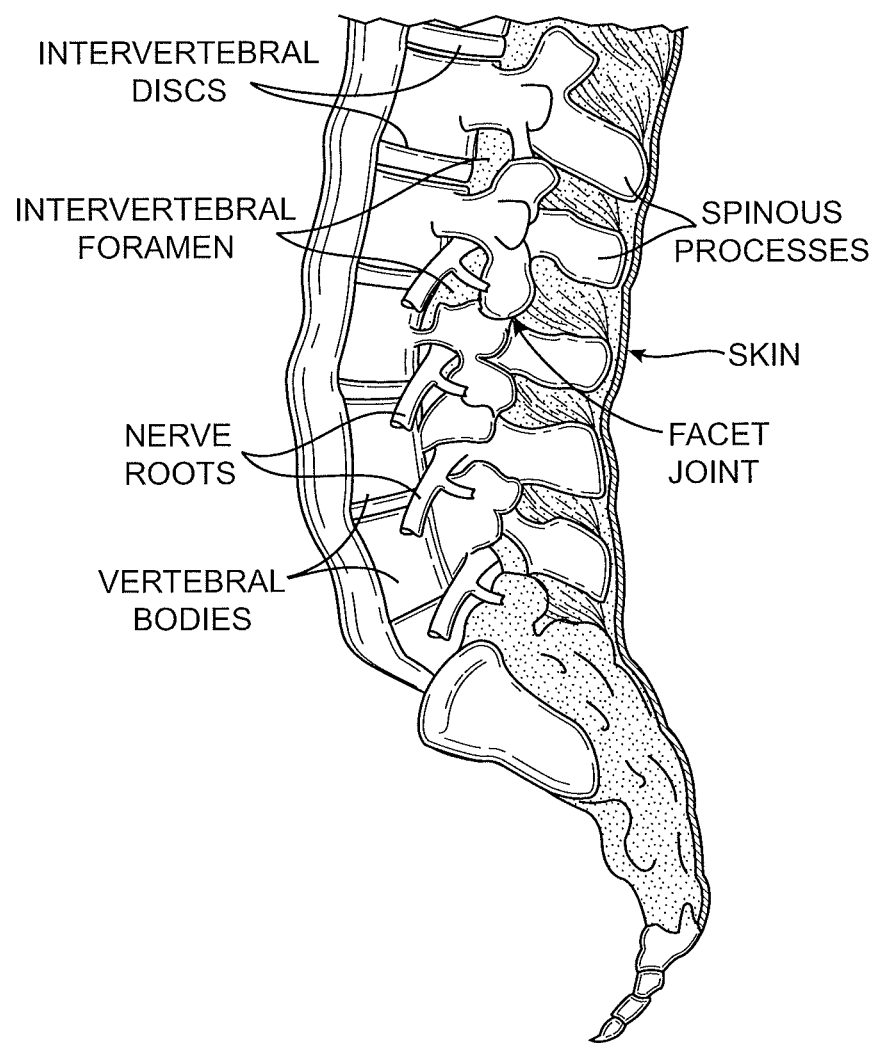
FIG. 2 is a left lateral view of the lumbar portion of a spine with sacrum and coccyx.
Figure 3:
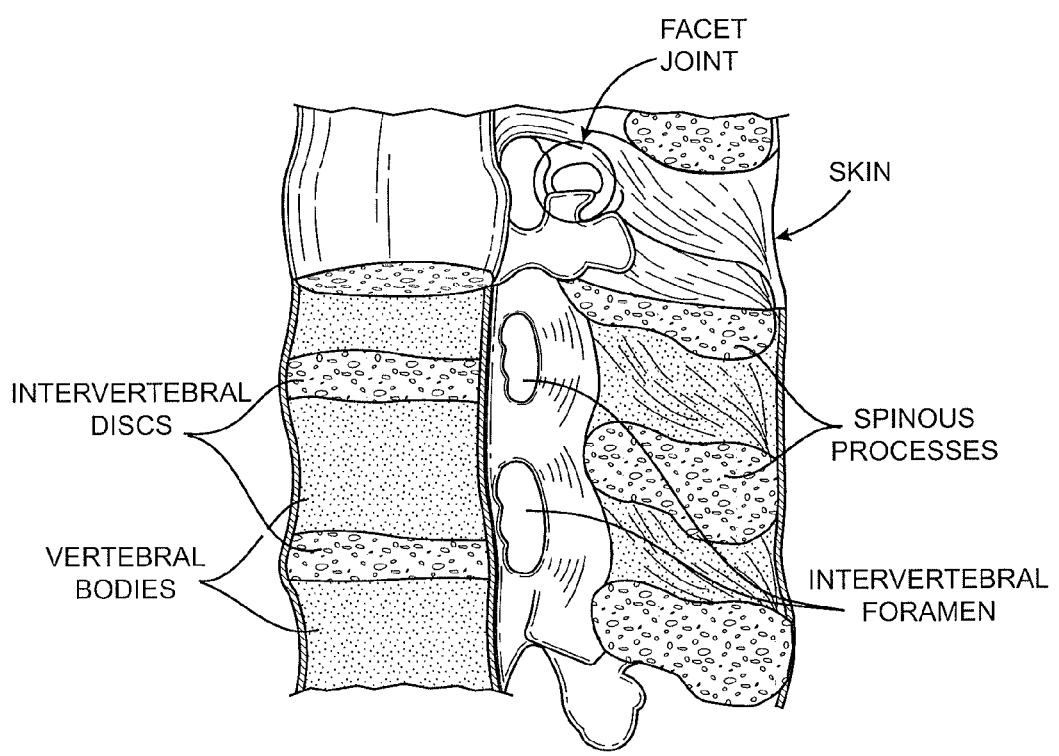
FIG. 3 is a left lateral view of a portion of the lumbar spine, showing only bone and ligament tissue and partially in cross section.
Figure 4:
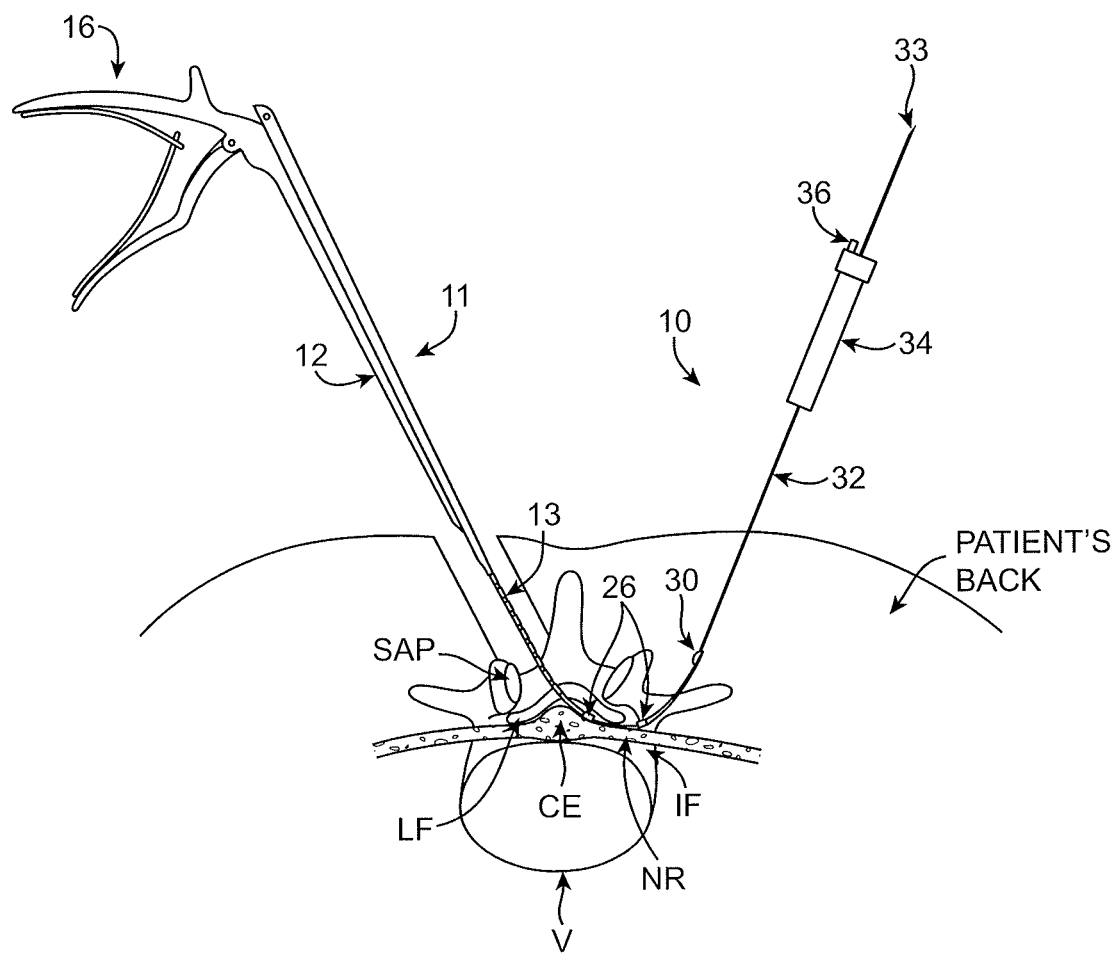
FIG. 4 is a cross-sectional view of a patient's back and spine with a side view of a guidewire and tissue modification system in place for performing a tissue removal procedure, according to one embodiment of the present invention.

Referring to FIG. 4, one embodiment of a guidewire system 10 is shown coupled with a tissue cutting device 11 in position within a patient's spine. Further description of various embodiments of cutting device 11 may be found in U.S. patent application Ser. No. 11/461,740, filed Aug. 1, 2006, entitled "MULTI-WIRE TISSUE CUTTER," Publication No. US-2008-0051812-A1, the full disclosure of which is hereby incorporated by reference. A number of alternative embodiments of cutting devices, many of which may be used (or adapted for use) with guidewire system 10, are further described in U.S. patent application Ser. No. 11/375,265, filed Mar. 13, 2006, entitled "METHODS AND APPARATUS FOR TISSUE MODIFICATION," now U.S. Pat. No. 7,887,538; Ser. No. 11/405,848, filed Apr. 17, 2006, entitled "MECHANICAL TISSUE MODIFICATION DEVICES AND METHODS," now U.S. Pat. No. 8,430,881; and Ser. No. 11/406,486, filed Apr. 17, 2006, entitled "POWERED TISSUE MODIFICATION DEVICES AND METHODS," now U.S. Pat. No. 7,938,830; and Ser. No. 11/429,377, filed May 4, 2006, entitled "FLEXIBLE TISSUE RASP," now U.S. Pat. No. 8,048,080. The full disclosures of all of the foregoing references are hereby incorporated by reference.

As described in further detail in U.S. patent application Ser. No. 11/461,740 (Publication No. US-2008-0051812-A1) tissue cutting device 11 may include a shaft 12, a proximal handle 16, a flexible distal portion 13, two or more cutting blades 26 and a guidewire coupling member 30. Guidewire system 10 may include a guidewire 32 having a sharpened tip 33 (often referred to herein as the "sharpened distal tip") for facilitating advancement of guidewire 32 through tissue. Optionally, guidewire 32 may also include a shaped member (not visible in FIG. 4) at the end opposite sharpened tip 33 (often referred to herein as the guidewire "proximal end") for coupling with coupling member 30. Guidewire system 10 may also include a guidewire handle 34 (or "distal handle") for coupling with guidewire 32, which in some cases may include a tightening member 36 for securing a portion of guidewire 32 within guidewire handle 34.

In some embodiments, cutting device 11 may be advanced into a patient's back through an incision 20, which is shown in FIG. 4 as an open incision but which may be a minimally invasive or less invasive incision in alternative embodiments. In some embodiments, device 11 may be advanced by coupling guidewire connector 30 with guidewire 32 that has been advanced between target and non-target tissues, and then pulling guidewire 32 to pull device 11 between the tissues. Various embodiments of such a method for delivering a device are described in further detail below. Generally, guidewire system 10 may be used to pull flexible distal portion 13 into place between tissues in hard-to-reach or tortuous areas of the body, such as between a nerve root (NR) and facet joint and through an intervertebral foramen (IF). Generally, flexible portion 13 may be advanced to a position such that blades 26 face tissue to be cut in a tissue removal procedure ("target tissue") and a non-cutting surface (or surfaces) of flexible portion 13 faces non-target tissue, such as nerve and/or neurovascular tissue. In the embodiment shown in FIG. 4, blades 26 are positioned to cut ligamentum flavum (LF) and may also cut hypertrophied bone of the facet joint, such as the superior articular process (SAP). (Other anatomical structures depicted in FIG. 4 include the vertebra (V) and cauda equina (CE)). In various alternative embodiments, flexible portion 13 may be replaced with a curved, rigid portion, a steerable portion, a straight portion with a distal extension or the like. The configuration, dimensions, flexibility, steerability, materials and the like of flexible portion 13 may be adjusted, in alternative embodiments, depending on a type of tissue or anatomical structure to be accessed or modified.

Before or after blades 26 are located in a desired position, guidewire 32 may be removably coupled with guidewire handle 34, such as by passing guidewire 32 through a central bore in handle 34 and moving tightening member 36 to secure a portion of guidewire 32 within handle 34. A physician (or two physicians or one physician and an assistant) may then pull on proximal handle 16 and distal handle 34 to apply tensioning force to guidewire 32 and cutting device 11 and to urge the cutting portion of device 11 against ligamentum flavum (LF), superior articular process (SAP), or other tissue to be cut. Proximal handle 16 may then be actuated, such as by squeezing in the embodiment shown, to cause one or both blades 26 to move toward one another to cut tissue. Proximal handle 16 may be released and squeezed as many times as desired to remove a desired amount of tissue. When a desired amount of tissue has been cut, guidewire 32 may be released from distal handle 34, and cutter device 11 and guidewire 32 may be removed from the patient's back.

With reference now to FIGS. 5A-5I, one embodiment of a method for advancing a tissue modifying device into a patient's body using a guidewire delivery system is shown. Although this method is shown in reference to placement of a device in a spine, in various alternative embodiments, such a method may be used to place similar or alternative tissue modification devices in other locations in a human body, such as between tissues in a joint space, in the abdominal cavity, or in the carpal tunnel of the wrist, between bone and soft tissue in other parts of the body, and the like.

Figure 5A:
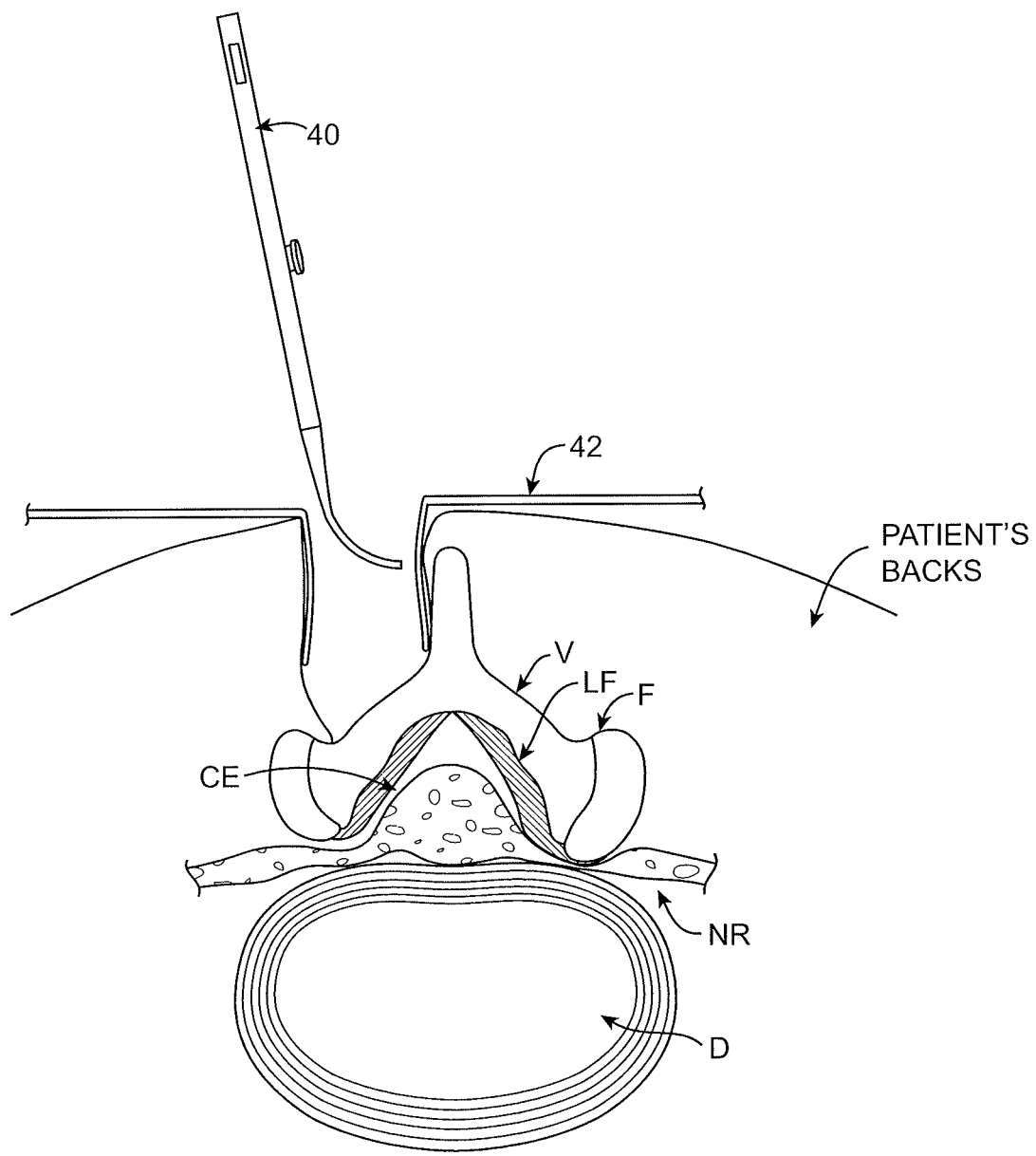
FIGS. 5A-5I illustrate one variation of a method for advancing a tissue modifying device into a patient's body using a guidewire delivery system.
Figure 5B:
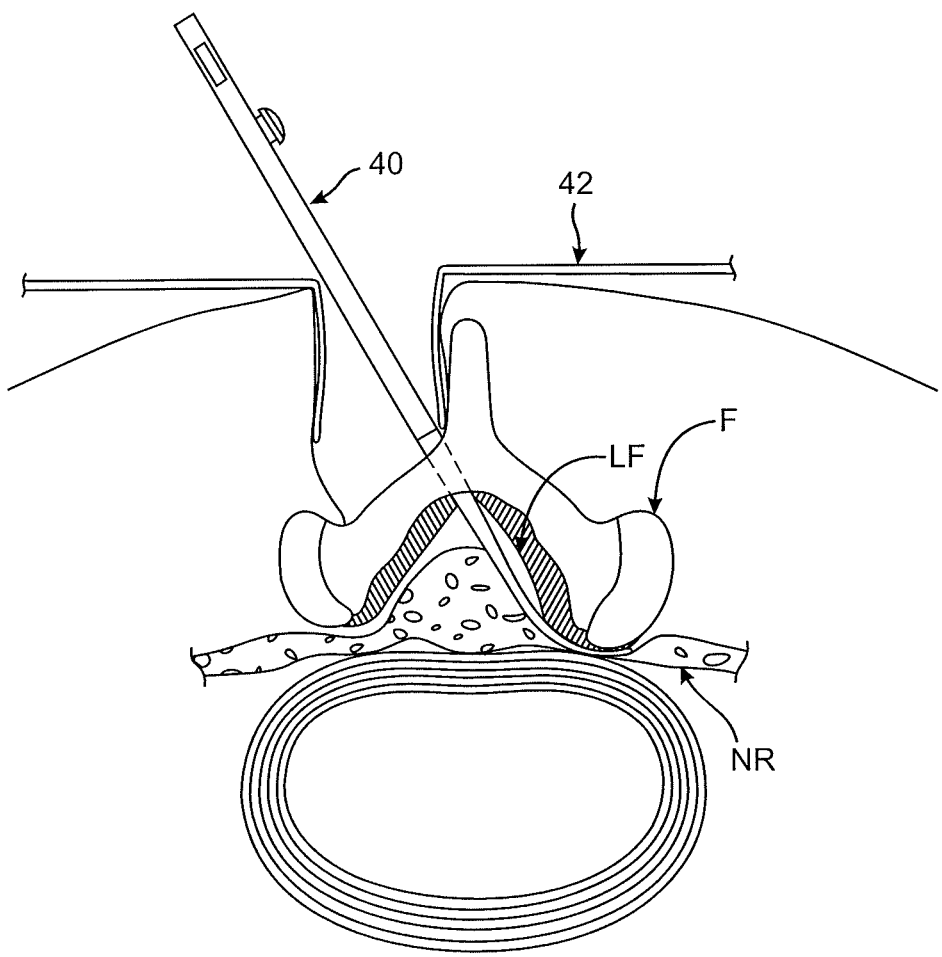
Figure 5C:
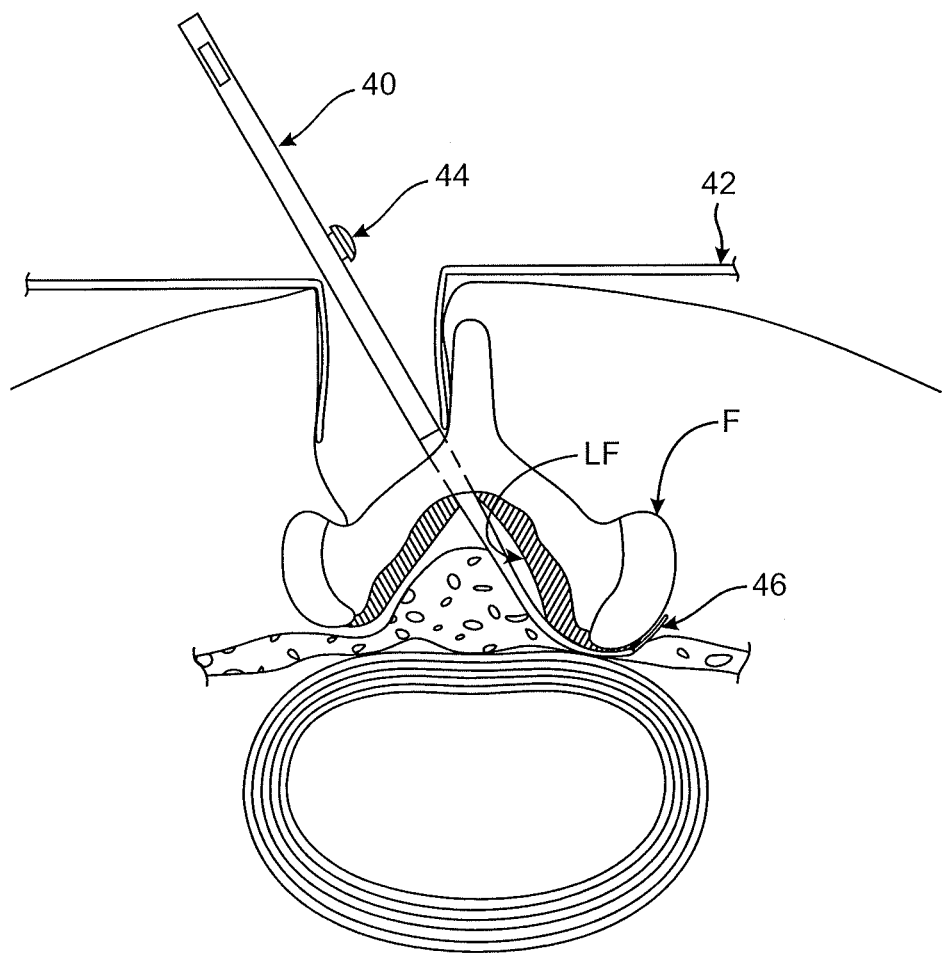
Figure 5D:
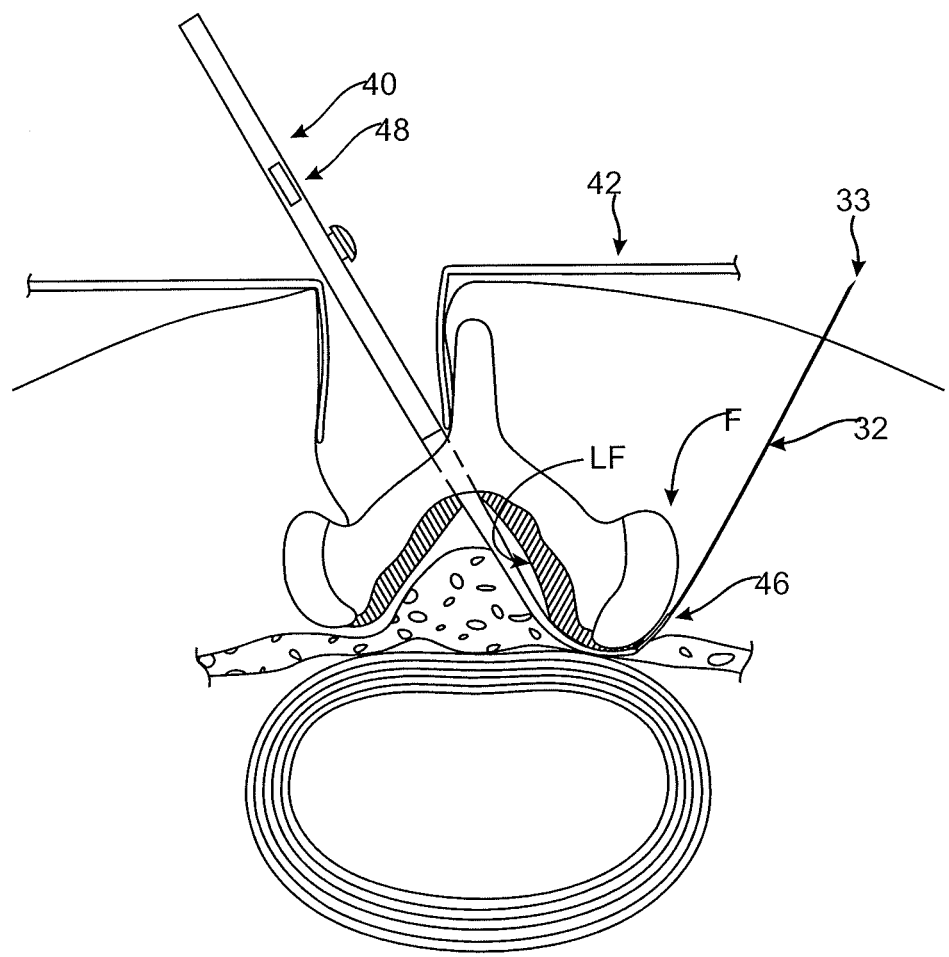
Figure 5E:
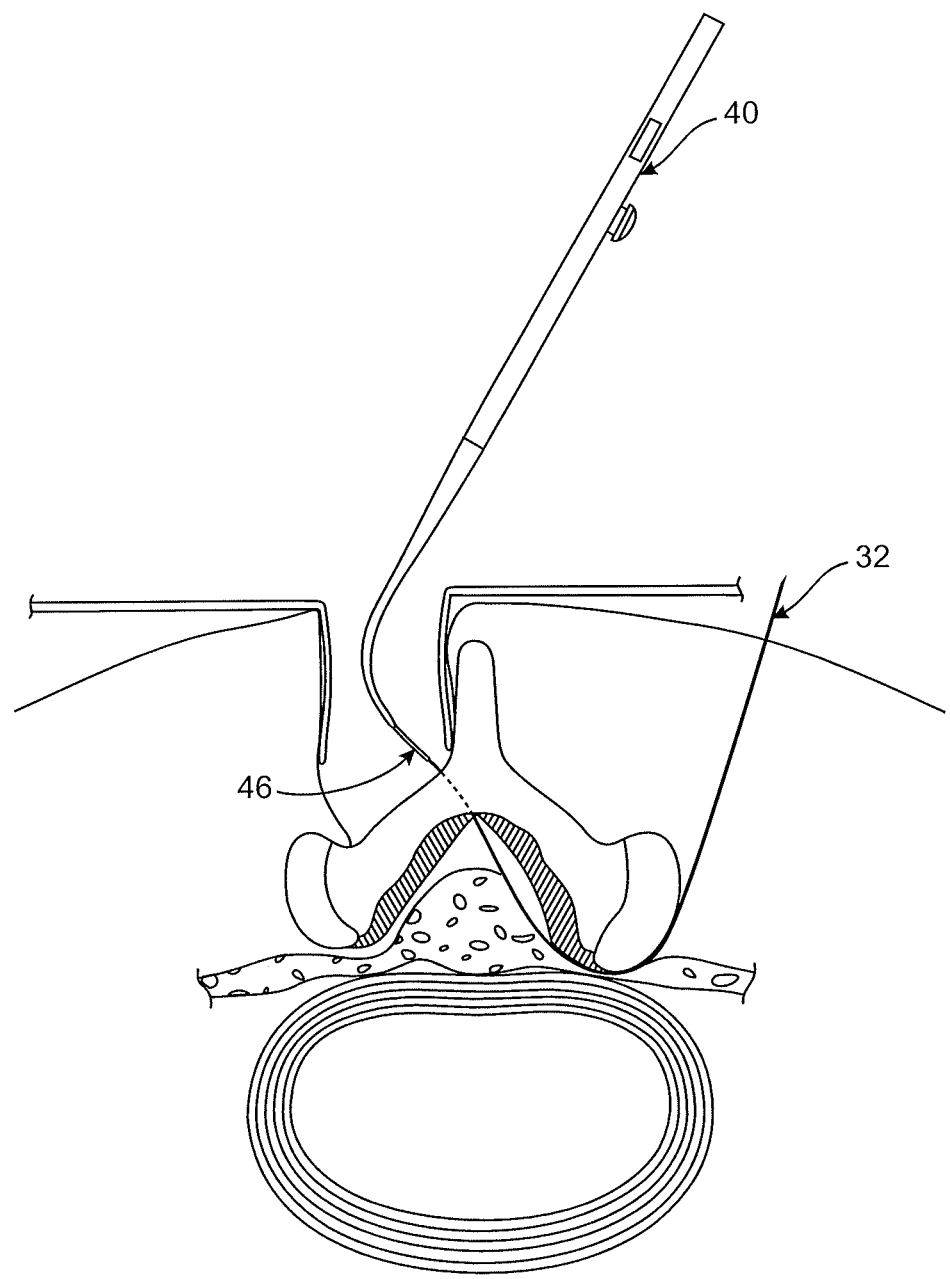
Figure 5F:
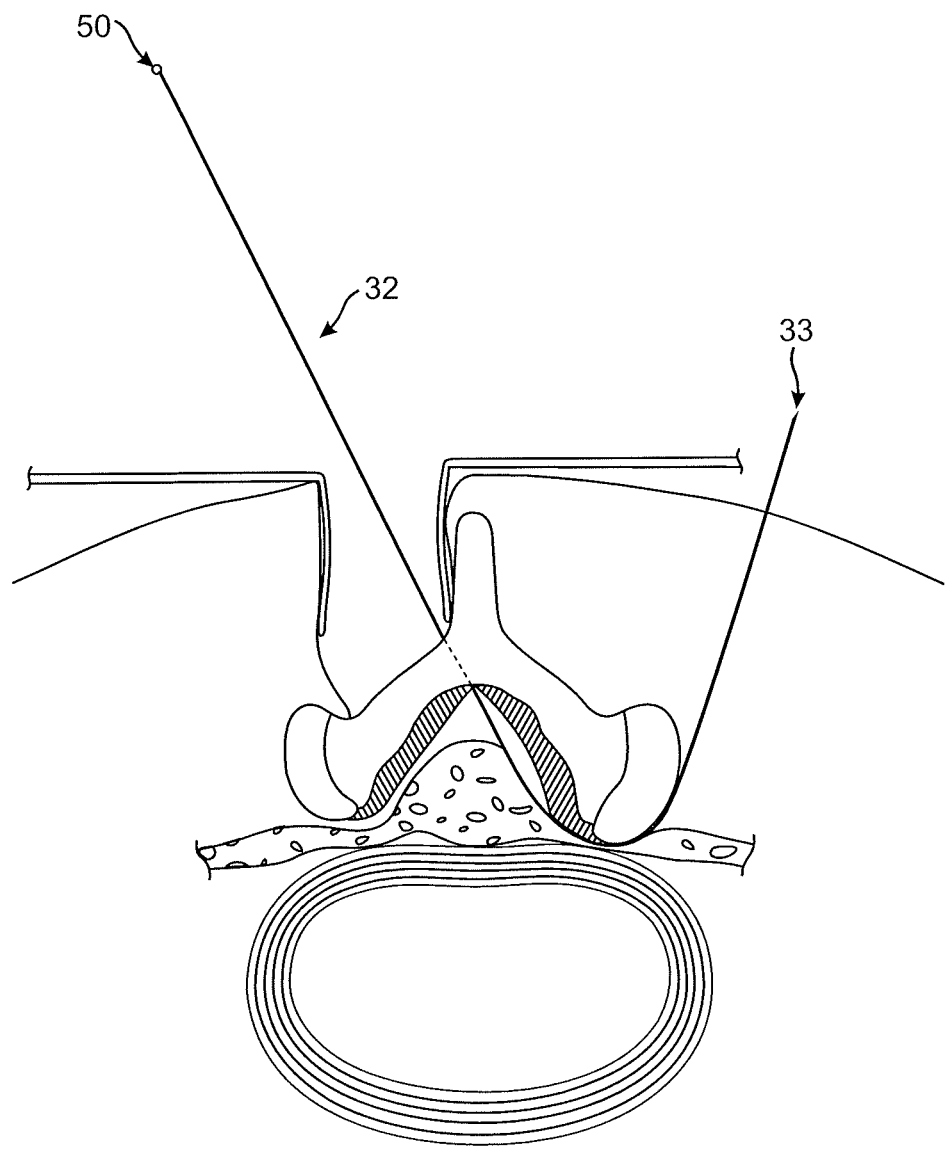

Referring to FIG. 5A, in one embodiment of a method for advancing a tissue modifying device, a probe 40 may be inserted into a patient's back using an open technique facilitated by retractors 42. Target tissues of a procedure, in this embodiment, may include ligamentum flavum (LF) and/or facet joint (F) tissue of a vertebra (V), which may impinge on non-target tissues, such as nerve root (NR) and/or cauda equina (CE), of the lumbar spine. Also depicted in FIG. 5A is an intervertebral disc (D). In FIG. 5B, a curved distal portion of probe 40 has been advanced to a position between target ligamentum flavum (LF) and non-target nerve root (NR) tissues. As depicted in FIG. 5C, in some embodiments, a curved guide member 46 may next be advanced out of an aperture on the curved distal portion of probe 40. In one embodiment, for example, guide member 46 may be housed within probe and advanced out of the distal aperture by advancing a slide member 44 on the shaft of probe 40. Next, as shown in FIG. 5D, guidewire 32 may be advanced through guide member 46 and out of the patient's back, using sharpened tip 33 to facilitate passage through the patient's back tissue. Probe 40 may then be removed, as shown in FIG. 5E, leaving guidewire 32 in place between the target and non-target tissues, as shown in FIG. 5F. Also shown in FIG. 5F is a shaped member 50 (in this embodiment, a ball) on the proximal end of guidewire 32.

Further description of methods, devices and systems for advancing a guidewire between tissues using a probe are provided in U.S. patent application Ser. No. 11/457,416, filed Jul. 13, 2006, entitled "SPINAL ACCESS AND NEURAL LOCALIZATION," now U.S. Pat. No. 7,578,819, the full disclosure of which is hereby incorporated by reference. As described in that reference, in some embodiments, the curved distal portion of probe 40, curved guide member 46, or both may include one, two or more electrodes to help locate nerve tissue before placing guidewire 32. Such neural localization helps ensure that guidewire 32 is positioned between target and non-target tissue, which in turn helps ensure that a tissue modification device (or devices) placed using guidewire 32 are oriented so that a tissue modifying portion (or portions) of the device face and act on target tissue and not on non-target tissue such as neural tissue.

Figure 5G:
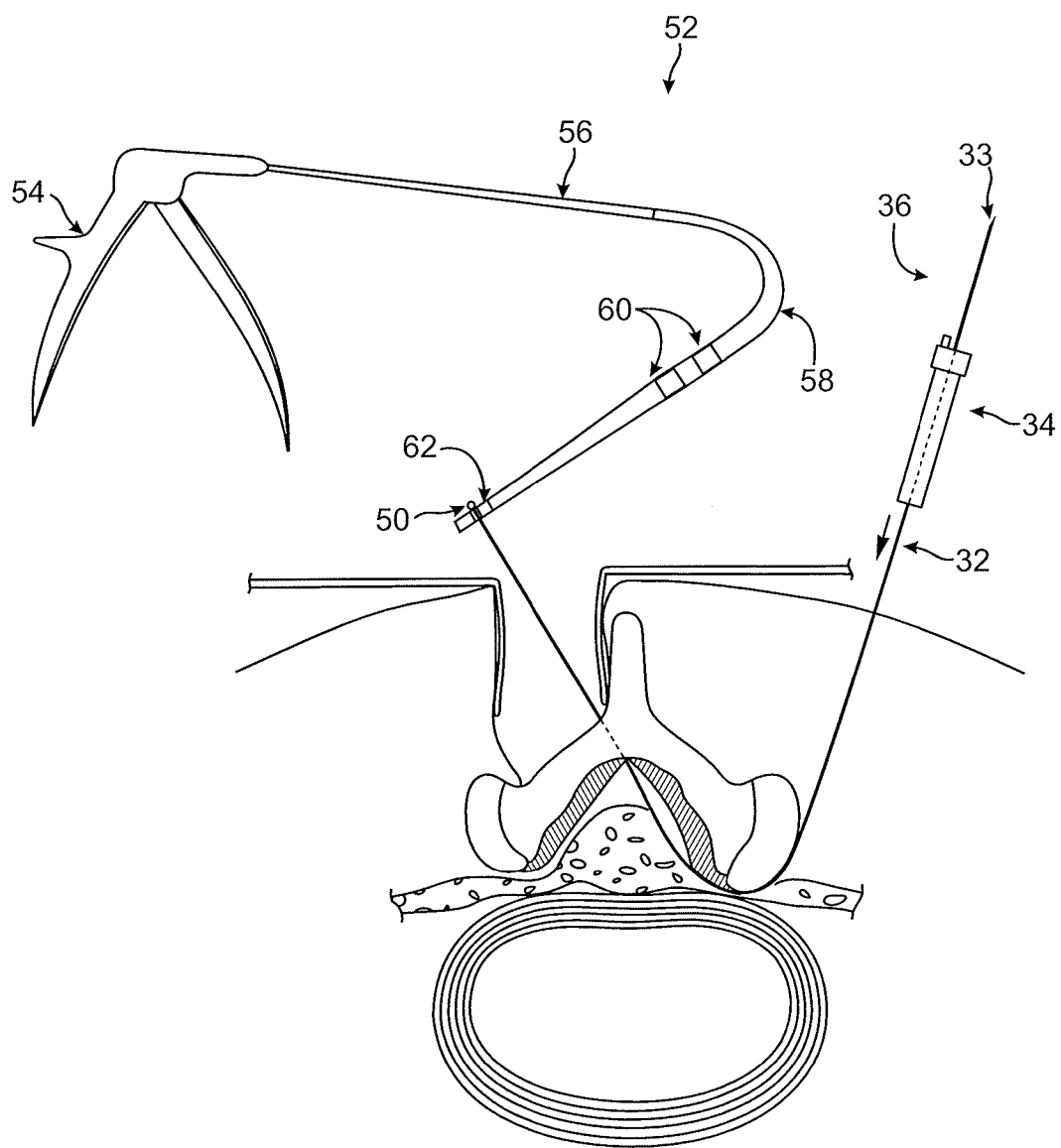

Referring now to FIG. 5G, once guidewire 32 is positioned between tissues, its proximal end with shaped member 50 may be coupled with a coupling member 62 on a distal end of a tissue modification device 52. Tissue modification device 52, in one embodiment, may include a proximal handle 54, a rigid proximal shaft portion 56, a flexible distal shaft portion 58, tissue cutting blades 60, and coupling member 62. Coupling member 62, various embodiments of which are described in greater detail below, may be either attached to or formed in distal shaft portion 58. In some embodiments, such as the one depicted in FIG. 5G, to attach guidewire 32 to coupling member 62, guidewire 32 may be laid into a channel on coupling member 62, and guidewire 32 and/or distal portion 58 may be rotated, relative to one another, to lock shaped member 50 into coupling member. Various alternative embodiments for coupling guidewires 32 with coupling members 62 are described in greater detail below. Before, after or during coupling of guidewire 32 and tissue modification device 52, guidewire 32 may also be coupled with distal guidewire handle 34, such as by advancing distal handle 34 over guidewire 32 (solid-tipped arrow).

Figure 5H:
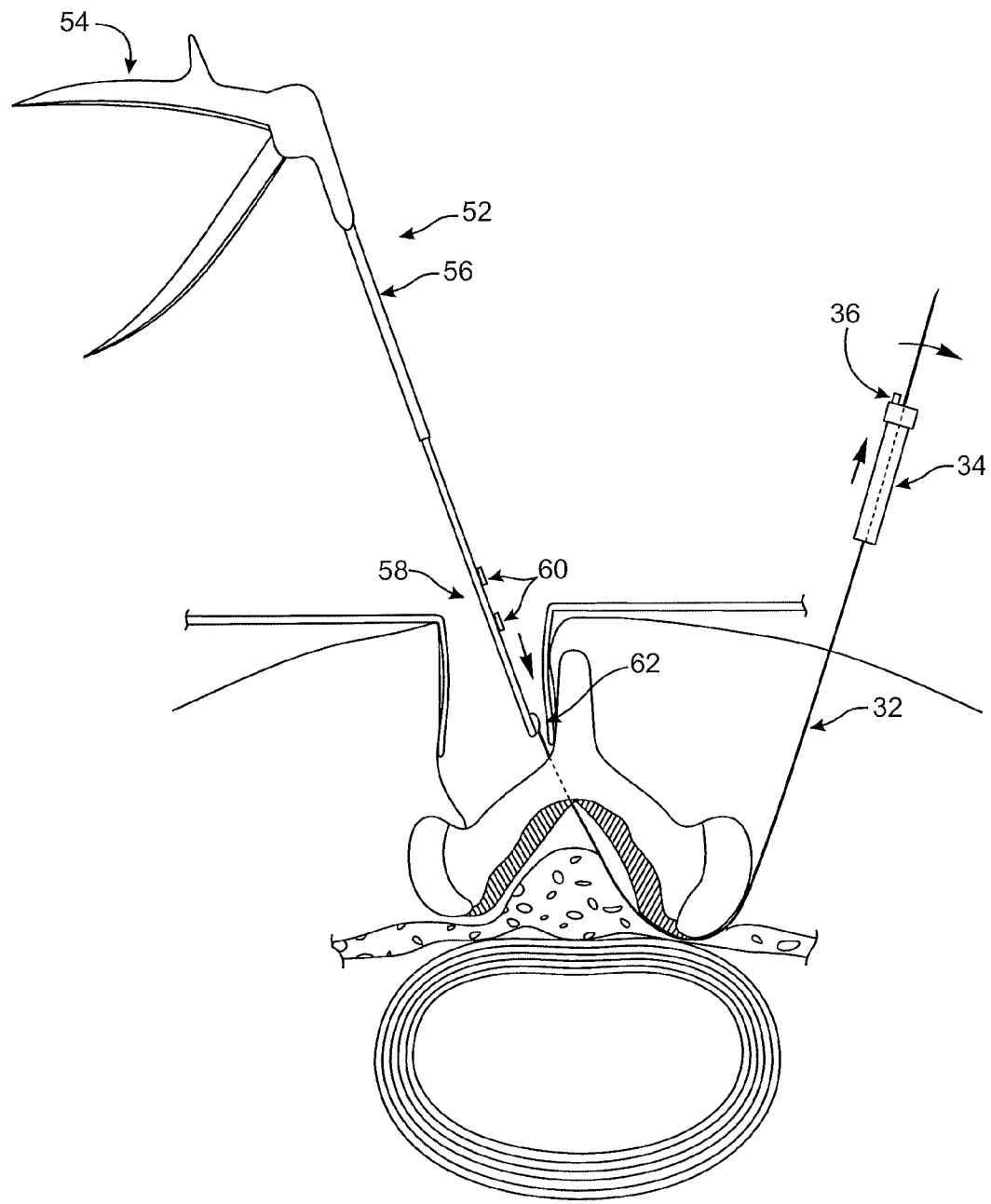
Figure 5I:
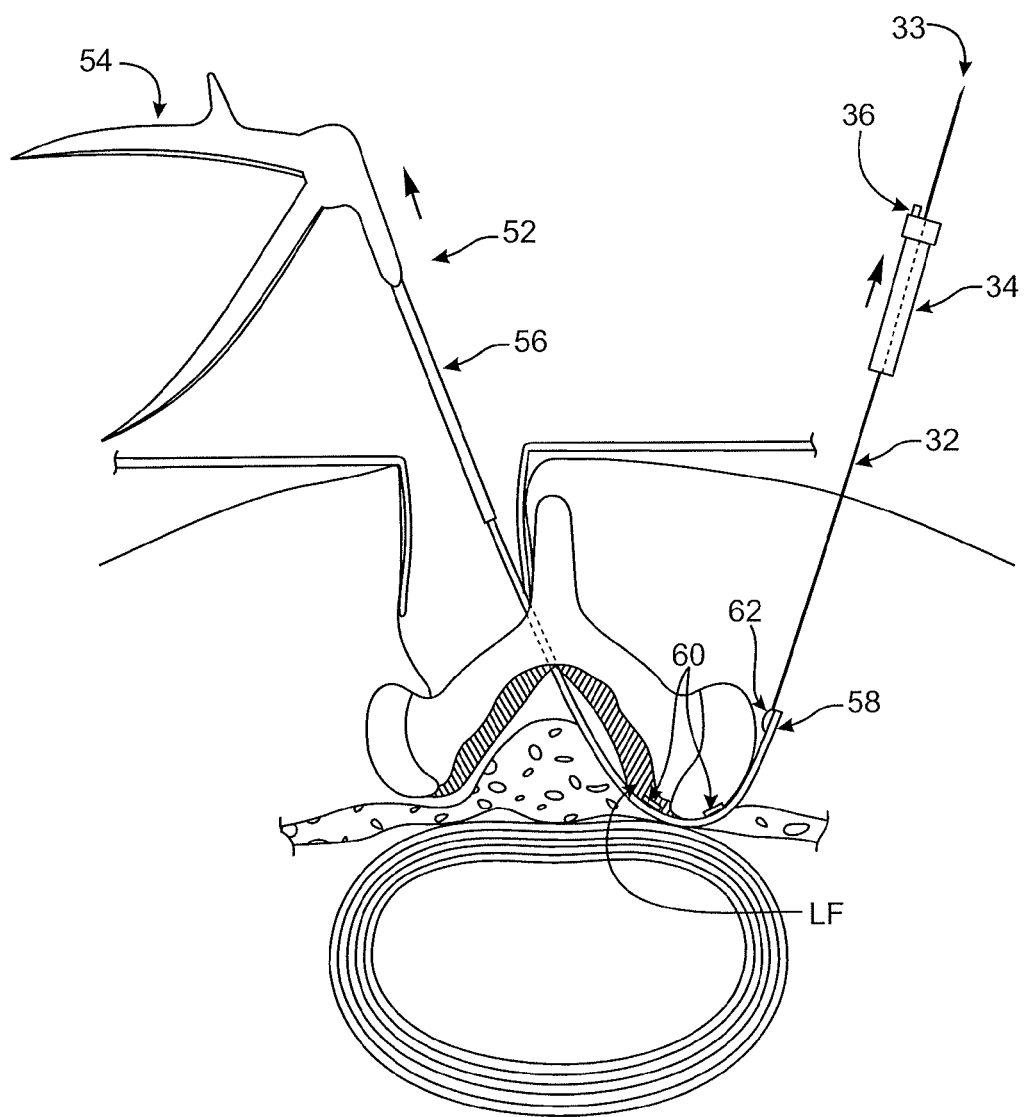

As depicted in FIG. 5H, tightening member 36 may next be moved (curved, solid-tipped arrow) to tighten distal handle 34 around guidewire 32. Distal handle 34 may then be pulled (straight, solid-tipped arrow) to pull guidewire 32 and thus advance distal shaft portion 58 of tissue modification device 52 into place between target and non-target tissues in the spine, as shown in FIG. 5I. Once device 52 is positioned as desired, as depicted in FIG. 5I, proximal handle 54 and distal handle 34 may be pulled (straight, solid-tipped arrows), to apply tensioning force to guidewire 32 and device 52 and thus urge flexible portion 58 and blades 60 against target tissue, such as ligamentum flavum (LF) and/or facet joint (F) tissue. Handle 54 may then be actuated (curved, double-tipped arrow) to cause blades 60 to cut target tissue. When a desired amount of tissue is cut, guidewire 32 may be released from distal handle 34, and tissue modification device 52 and guidewire 32 may be removed from the patient's back. This method for advancing tissue modification device 52 using guidewire 32 is but one exemplary embodiment.

Various aspects of the method embodiment just described, such as the number or order of steps, may be changed without departing from the scope of the invention. Furthermore, a number of alternative embodiments of various devices and device elements are described below, which may be used in various embodiments of such a method. For example, in one alternative embodiment (not shown), probe 40 and tissue modification device 52 may be combined into one device. Such a device may include a guidewire lumen through which guidewire 32 may be passed. The combined device may be partially inserted into a patient, and guidewire 32 advanced between target and non-target tissues through the guidewire lumen. Shaped member 50 of guidewire 32 may then catch on one or more coupling members 62 of the combined device, to allow the device to be pulled into position between the target and non-target tissues. Guidewire 32 may then further be used to help apply tensioning force to the device to urge an active portion against target tissues. In another alternative embodiment, access to the intervertebral foramen may be achieved using a lateral approach, rather than a medial approach. These are but two examples of many alternative embodiments, and a number of other alternatives are contemplated.

Figure 6:
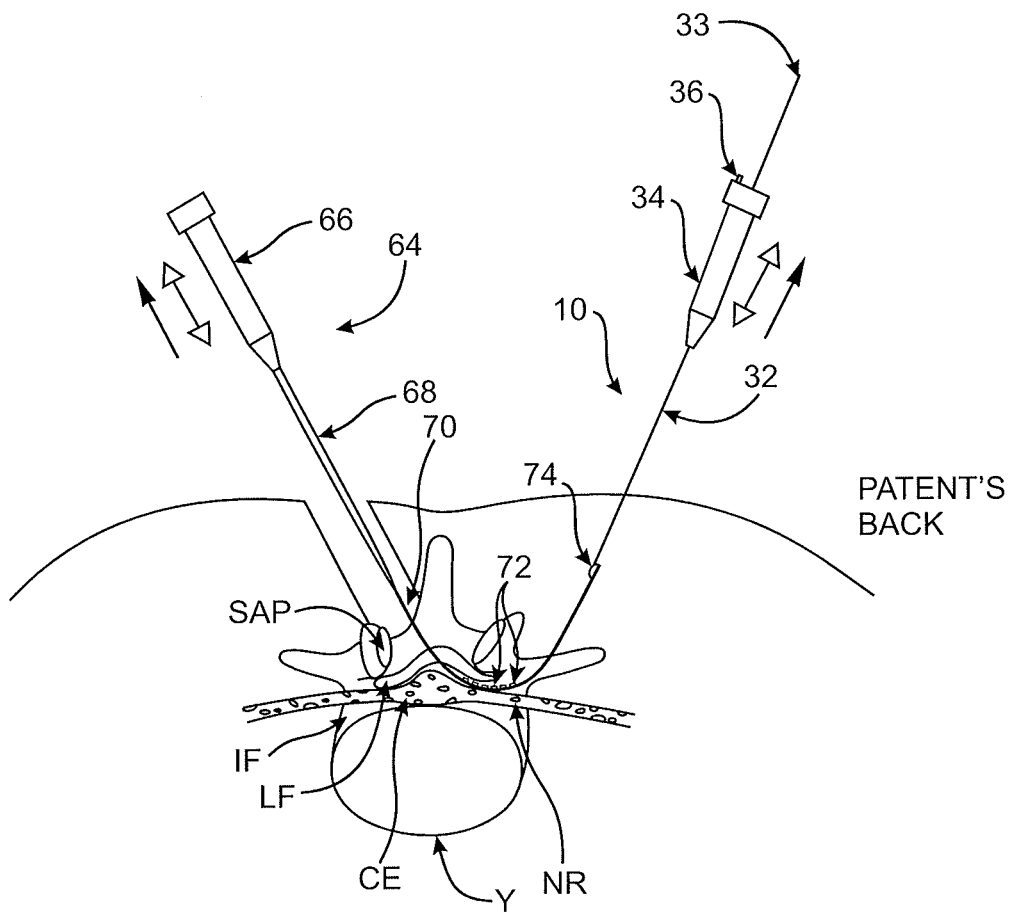
FIG. 6 is a cross-sectional view of a patient's back and spine and a side view of a rasp device and guidewire system, according to one embodiment of the present invention.

With reference now to FIG. 6, guidewire system 10 is shown with an alternative embodiment of a tissue modification device 64, which may include a proximal handle 66, a rigid proximal shaft portion 68, and a distal flexible shaft portion 70. Multiple abrasive members 72 and a guidewire coupling member 74 may be coupled with one side of flexible shaft portion 70. In this embodiment, guidewire 32 may be coupled with coupling member 74 and used to pull distal shaft portion 70 of modification device 64 into place between target and non-target tissues. Proximal handle 66 and distal handle 34 may then be pulled/tensioned (solid-tipped arrows) to urge abrasive members 72 against the target tissue, and handles 66, 34 may further be used to reciprocate device 64 and guidewire 32 back and forth (hollow/double-tipped arrows) to modify the target tissue. Reciprocation and tensioning may be continued until a desired amount of tissue is removed, at which point guidewire 32 may be released from distal handle 34, and device 64 and guidewire 32 may be removed from the patient's back. In various embodiments, tissue modification device 64 may include any of a number of abrasive members 72, abrasive materials, or the like, which may be arrayed along distal shaft portion 70 for any desired length and in any desired configuration. Further examples of abrasive members 70, materials, surfaces and the like are described in U.S. patent application Ser. No. 11/429,377 (now U.S. Pat. No. 8,048,080), which was previously incorporated by reference. In various alternative embodiments, shaft portions 68, 70 may both be rigid or may both be flexible and may have different cross-sectional shapes or the same shape.

Figure 7:
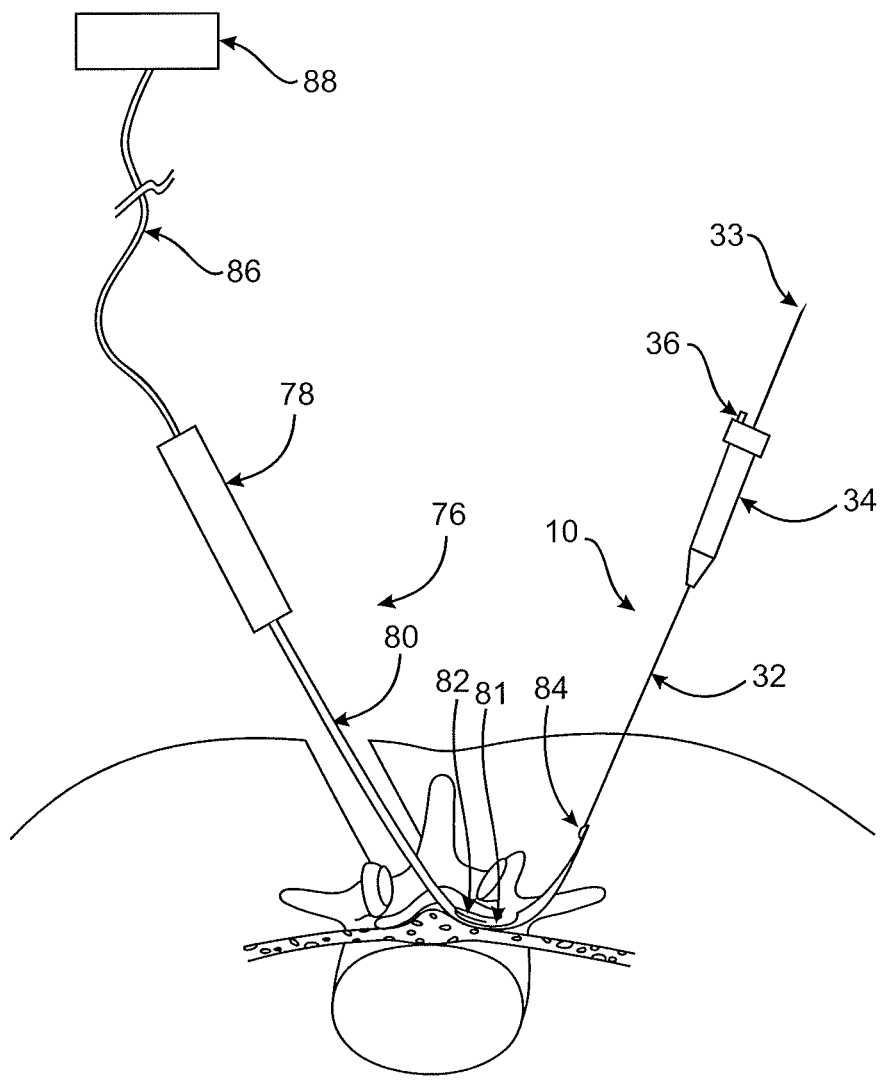
FIG. 7 is a cross-sectional view of a patient's back and spine and a side view of an ultrasound device and guidewire system, according to one embodiment of the present invention.

Referring to FIG. 7, in another alternative embodiment, an ultrasound tissue modification device 76 may be advanced into position in a patient's back using guidewire system 10. In one embodiment, for example, ultrasound device 76 may include a proximal handle 78, a hollow shaft 80 having a distal window 81, multiple ultrasound wires 82 extending through shaft 80 and into window 81, a guidewire connector 84 coupled with a tapered distal end of shaft 80, an ultrasound generator 88, and a wire 86 coupling handle 78 with generator 88. Handle 78 may include, for example, an ultrasound transducer, horn and/or other ultrasound transmission components. Shaft 80 may be completely rigid, completely flexible, or part rigid/part flexible, according to various embodiments. Ultrasound energy provided by generator 88 may be converted in handle 78 to reciprocating motion of wires 82, and reciprocating wires 82 may be used to cut, chisel or otherwise modify soft and/or hard tissues. Further description of such an embodiment is provided in U.S. patent application Ser. No. 11/461,740 (Publication No. US-2008-0051812-A1), which was previously incorporated by reference. Guidewire connector 84 may comprise one of a number of different connectors, various embodiments of which are described in further detail below.

Figure 8A:
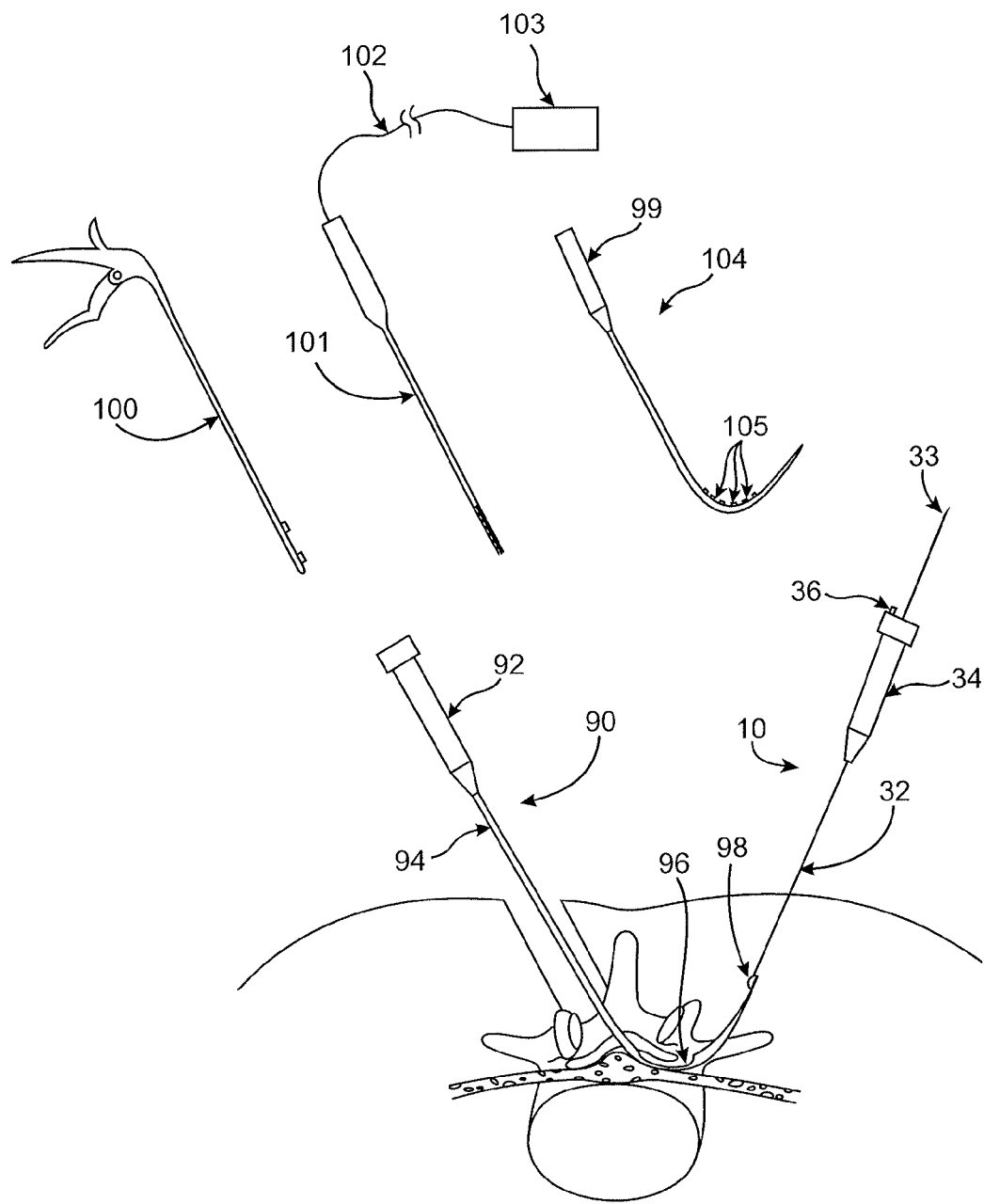
FIG. 8A is a cross-sectional view of a patient's back and spine and a side view of a tissue access device with swappable tissue modification devices and a guidewire system, according to one embodiment of the present invention.

In another embodiment, and with reference now to FIG. 8A, guidewire system 10 may be used to pull/advance a tissue access device 90 into place between target and non-target tissues. Tissue access device 90, for example, may include a proximal handle 92, a hollow shaft 94 having a distal curved portion with a distal window 96, and a guidewire connector 98 coupled with a tapered distal end of shaft 94. As with previously described embodiments, shaft 94 may be flexible along its entire length, rigid along its entire length, or rigid in part and flexible in part, and may be made of any suitable material or combination of materials. In some embodiments, shaft 94 may also be steerable, such as with one or more pull wires or other steering mechanisms, for example to steer or curve a distal portion of shaft 94.

Once access device 90 is in a desired position, with window 96 facing target tissue (such as ligamentum flavum and/or facet joint bone in the spine) and an atraumatic surface of shaft 94 facing non-target tissue, any of a number of compatible tissue modification devices 100, 101, 104 or other devices may be advanced through access device 90 to perform a tissue modification procedure or other functions. Such devices may swappable in and out of access device 90 and may be in the form of cartridges, so that various cartridges may be inserted and removed as desired, over the course of a procedure. Examples of several tissue modification devices are shown in FIG. 8A, including a rongeur device 100, an ultrasound device 101 (including wire 102 and ultrasound generator 103), and an abrasive, reciprocating device 104. Further examples of tissue modification and other devices are described below with reference to FIGS. 8B-8M.

In one embodiment, for example, at least a distal portion of each tissue modification device 100, 101, 104 may be flexible, and a proximal portion of each modification device 100, 101, 104 may have a locking feature for locking into proximal handle 92 of access device 90. Thus, a given modification device, such as abrasive device 104, may be advanced into handle 92 and shaft 94, so that abrasive members 105 of device 104 are exposed through window 96 and locking feature 99 of device couples and locks within handle 92. A user may then grasp handles 34 and 92, pull up to urge abrasive members 105 against target tissue, and reciprocate access device 90 and guidewire system 10 back and forth to remove target tissue. The user may then choose to remove abrasive device 104 and insert one of the other devices 100, 101 to further modify target tissues.

In various embodiments, any of a number of tissue modification devices and/or other devices may be provided (for example as cartridges) for used with access device 90. In some embodiments, one or more of such devices may be provided with access device 90 and guidewire device 10 as a system or kit. Any given tissue modification device may act on tissue in a number of different ways, such as by cutting, ablating, dissecting, repairing, reducing blood flow in, shrinking, shaving, burring, biting, remodeling, biopsying, debriding, lysing, debulking, sanding, filing, planing, heating, cooling, vaporizing, delivering a drug to, and/or retracting target tissue. Non-tissue-modifying devices or cartridges may additionally or alternatively be provided, such as but not limited to devices for: capturing, storing and/or removing tissue; delivering a material such as bone wax or a pharmacologic agent such as thrombin, NSAID, local anesthetic or opioid; delivering an implant; placing a rivet, staple or similar device for retracting tissue; delivering a tissue dressing; cooling or freezing tissue for analgesia or to change the tissue's modulus of elasticity to facilitate tissue modification; visualizing tissue; and/or diagnosing, such as by using ultrasound, MRI, reflectance spectroscopy or the like. In given method, system or kit, any combination of tissue modification and/or non-tissue-modifying devices may be used with access device 90.

Figure 8B:
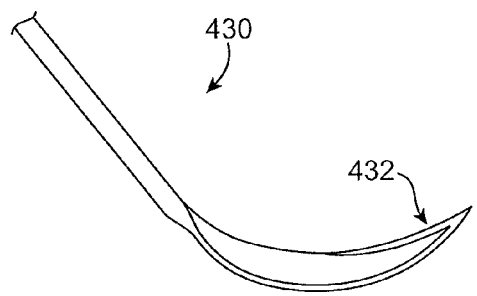
FIGS. 8B-8M are side/perspective views of distal portions of a number of different devices which may be placed through/used with a tissue access device such as that shown in FIG. 8A, according to various embodiments of the present invention.
Figure 8C:
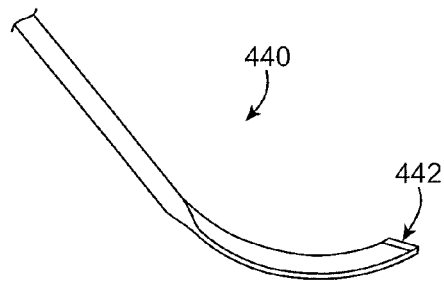
Figure 8D:
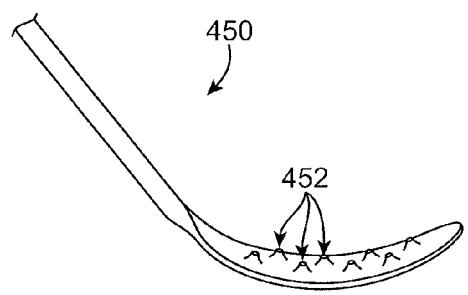
Figure 8E:
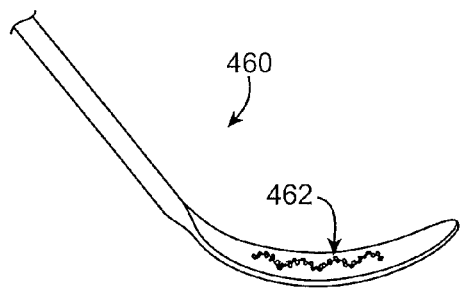
Figure 8F:
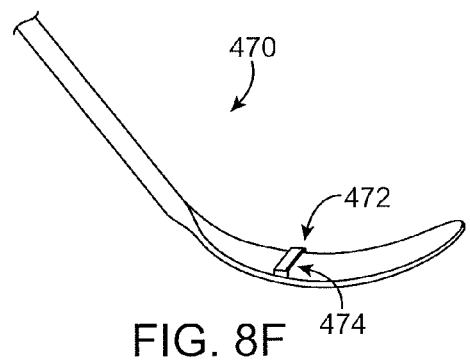
Figure 8G:
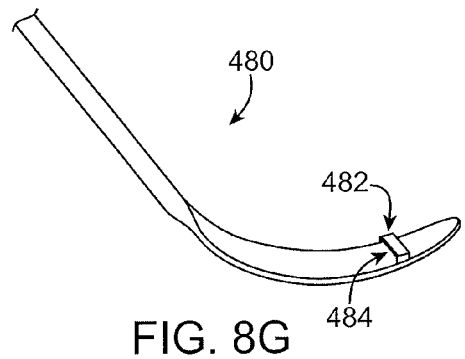
Figure 8H:
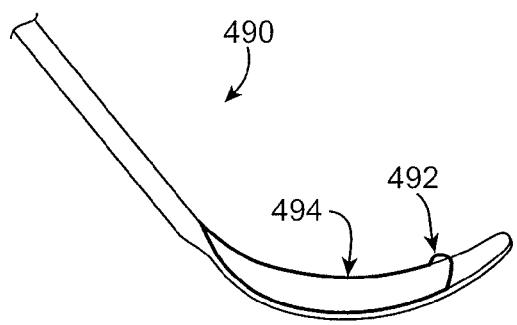

With reference now to FIGS. 8B-8M, distal portions of a number of exemplary embodiments of devices (which may be in cartridge form in some embodiments) for use with access device 90 are shown. FIG. 8B shows a device 430 including a sharpened, pointed, double-beveled distal tip 432. Tip 432 may be advanced across window 96 of access device 90 to cut tissue. FIG. 8C shows a device 440 including a diagonal-edge distal cutting tip 442, which may be used in a similar manner to cut tissue. FIG. 8D shows a device 450 including multiple volcano-shaped abrasive members 452. In alternative embodiments of abrasive devices, any suitable abrasive members or surfaces may be used. FIG. 8E, for example, shows a device 460 including a portion of a Gigli saw 462 attached to the device's upper surface, such as by welding. Any of a number of blades may alternatively be attached to a device, such as in the device 470 shown in FIG. 8F. Here, device 470 includes a proximally placed blade 472 having a cutting edge 474, which may be advanced across window 96 to cut tissue. FIG. 8G shows an alternative embodiment in which a device 480 includes a distally placed blade 482 with a cutting edge 484 that may be drawn back/retracted across window 96 to cut tissue. In another tissue-modifying embodiment, FIG. 8H shows a device 490 including a radiofrequency (RF) loop electrode 492 for cutting tissue and extending proximally via two insulated wires 494.

Figure 8I:
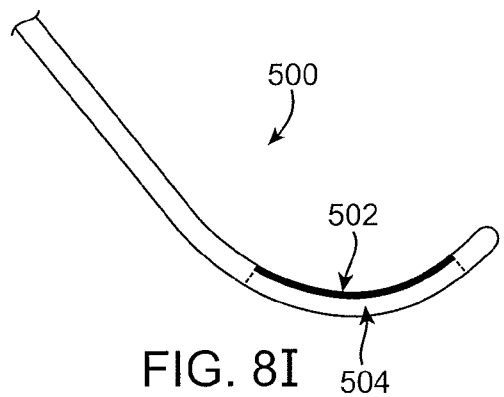
Figure 8J:
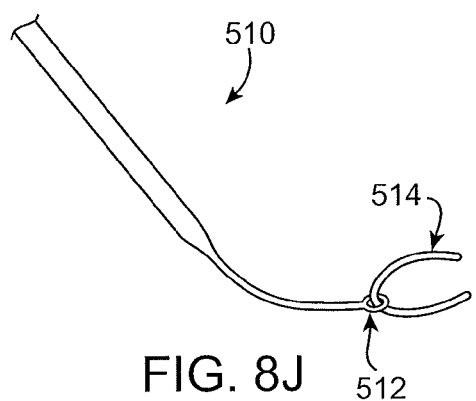
Figure 8K:
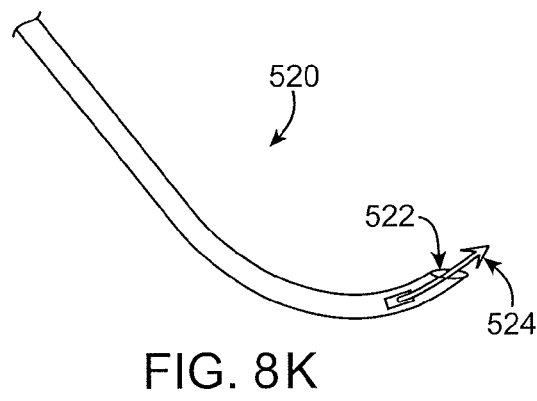

With reference to FIG. 8I, in an alternative embodiment, a device 500 may include a side-facing aperture 502 and a chamber 504. Device 500 may be advanced into access device 90 to align aperture 502 with window 96 and may then be used to collect tissue in chamber 504. Device 500 may then be removed through access device 90 to remove the tissue from the patient. This may be repeated as many times as desired, to remove cut tissue from the patient. FIG. 8J shows a device 510 having a clamp 512 for delivering an implant 514. Implant 514, for example, may be a posterior decompression implant such as the X STOP® Interspinous Process Decompression (IPD®), offered by St. Francis Medical Technologies, Inc.® (Alameda, Calif.), a foraminal implant such as that described in PCT Patent Application Pub. No. WO 2006/042206A2, or any other suitable implant for the spine or other area of the body. FIG. 8K shows an embodiment of a device 520 used for delivering a rivet (or "tissue anchor") 524 through a distal aperture 522. In one embodiment, for example, tissue anchor 524 may be anchored to bone and used to retract ligamentum flavum tissue to increase the area of a space in the spine. Such a device is described in more detail, for example in U.S. patent application Ser. No. 11/250,332, filed Oct. 15, 2004, entitled "DEVICES AND METHODS FOR SELECTIVE SURGICAL REMOVAL OF TISSUE," now U.S. Pat. No. 7,738,968, the full disclosure of which is hereby incorporated by reference.

Figure 8L:
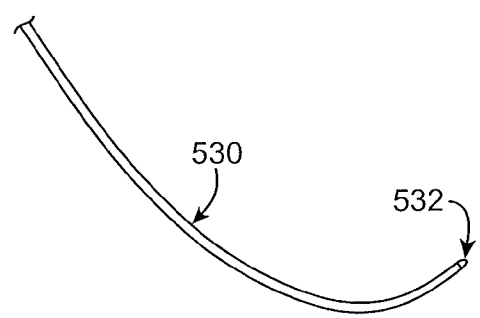
Figure 8M:
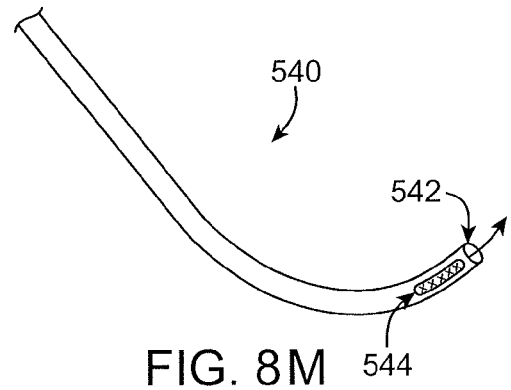

In another embodiment, and with reference to FIG. 8L, a visualization device 530 having a visualization element 532 may be used with access device 90. Such a device may include, for example, an endoscope, fiber optics, a camera coupled with a catheter or the like. In other embodiments, ultrasound, MRI, spectroscopy or other diagnostic or visualization devices may be used. FIG. 8M shows an alternative embodiment of a device 540, which includes a distal aperture 542 through which a tissue dressing 544 may be delivered. Tissue dressing 544, for example, may include one or more fabrics, gel foam or the like. In some embodiments, one or more pharmacologic agents may be delivered through device 540. Alternatively or additionally, irrigation and/or suction may be provided through device 540. As should be apparent from the foregoing description, any suitable device, cartridge or combination of devices/cartridges may be used with access device 90 in various embodiments.

Figure 9:
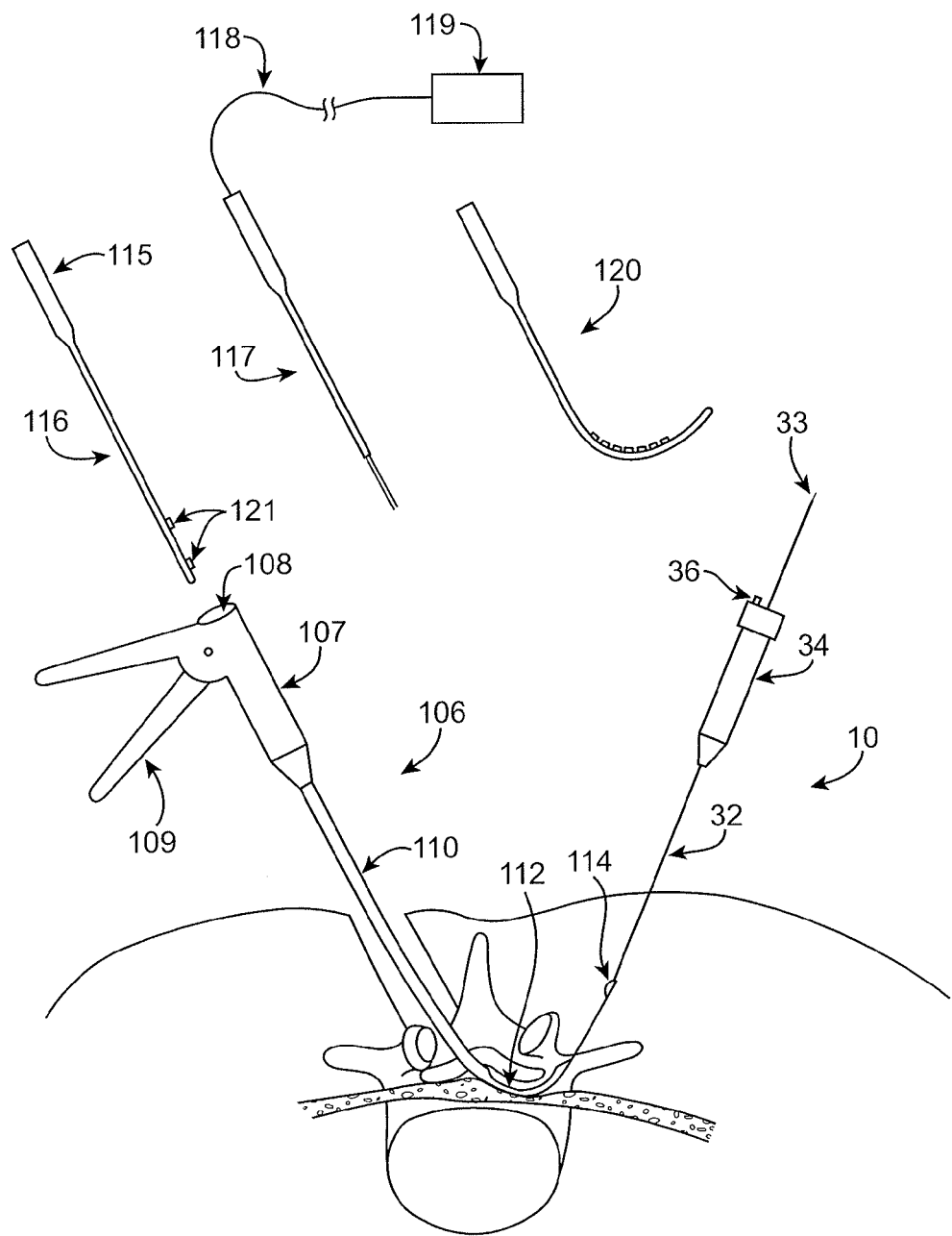
FIG. 9 is a cross-sectional view of a patient's back and spine and a side view of a tissue access device with swappable tissue modification devices and a guidewire system, according to an alternative embodiment of the present invention.

Referring now to FIG. 9, another embodiment of a tissue access device 106, which may be advanced to a position in a patient's back using guidewire system 10, is shown. Tissue access device 106 may include, for example, a proximal handle 107 having a hollow bore 108 and an actuator 109, a hollow shaft 110 extending from proximal handle 107 and having a distal curved portion and a distal window 112, and a guidewire coupling member 114 coupled with a tapered distal end of shaft 110. As with the previously described embodiment, a number of different tissue modification devices 116, 117, 120 may be inserted and removed from access device 106 to perform a tissue modification procedure, such as a rongeur 116, an ultrasound device 117 (including a wire 118 and generator 119), and an abrasive device 120. In the embodiment of FIG. 9, however, handle 107 includes the additional feature of actuator 109, which may be used to activate one or more tissue modifying members of various tissue modification devices. For example, rongeur 116 may be advanced into hollow bore 108 and shaft 110, to position blades 121 of rongeur 116 so as to be exposed through window 112, and to lock a locking member 115 of rongeur 116 within handle 107. Actuator 109 may then be moved back and forth (by squeezing and releasing, in the embodiment shown) to move one or both blades 121 back and forth to cut target tissue. Optionally, rongeur 116 may then be removed from access device 106 and a different modification device 117, 120 inserted to further modify target tissue. Actuator 109 may be used with some modification devices and not others. Again, in some embodiments, access device 106, guidewire system 10 and one or more modification devices 116, 117, 120 may be provided as a system or kit.

Figure 10:
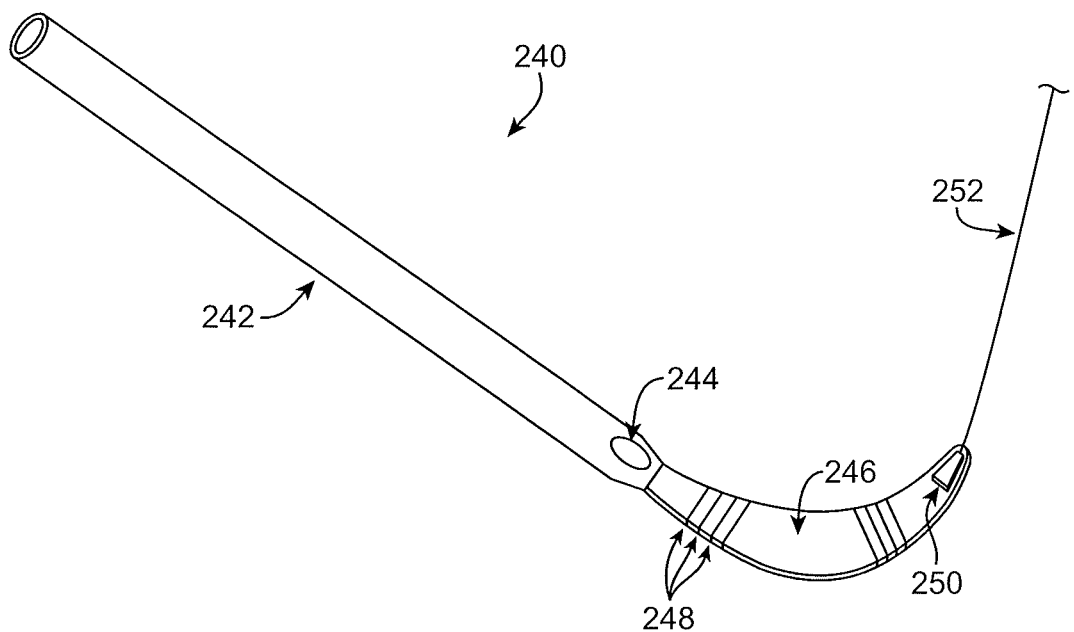
FIG. 10 is a perspective view of a tissue access device coupled with a guidewire, according to one embodiment of the present invention.

With reference now to FIG. 10, a perspective view of one embodiment of a tissue access device 240 is shown. Device 240 may include an elongate, hollow shaft 242 having a distal aperture 244, a distal extension 246 (or "platform" or "tissue shield") extending beyond shaft 242, and a guidewire coupling member 250 attached to distal extension 246 for coupling with a guidewire 252. Both shaft 242 and distal extension 246 may be either rigid or flexible, in various embodiments. In the embodiment shown, distal extension 246 includes multiple flexibility slits 248 to enhance flexibility of that portion of device 240. Shaft 242, distal extension 246 and guidewire coupling member 250 may be made of any suitable material (or materials), and may be made from one piece of material as a single extrusion or from separate pieces attached together, in alternative embodiments. Suitable materials include, for example, metals, polymers, ceramics, or composites thereof. Suitable metals may include, but are not limited to, stainless steel (303, 304, 316, 316L), nickel-titanium alloy, tungsten carbide alloy, or cobalt-chromium alloy, for example, Elgiloy® (Elgin Specialty Metals, Elgin, Ill., USA), Conichrome® (Carpenter Technology, Reading, Pa., USA), or Phynox® (Imphy SA, Paris, France). Suitable polymers include, but are not limited to, nylon, polyester, Dacron®, polyethylene, acetal, Delrin® (DuPont, Wilmington, Del.), polycarbonate, nylon, polyetheretherketone (PEEK), and polyetherketoneketone (PEKK). Ceramics may include, but are not limited to, aluminas, zirconias, and carbides.

In addition to various materials, tissue access device 240 may have any desired combination of dimensions and shapes. In some embodiments, for example, shaft 242 and distal extension 246 have different cross-sectional shapes, while in other embodiments, they may have the same cross-sectional shape. Some embodiments may include additional features, such as a mechanism for changing distal extension 246 from a straight configuration to a curved configuration (such as with one or more pull wires).

Any of a number of different surgical/tissue modification devices, such as but not limited to those described in reference to FIGS. 8 and 9, may be used in conjunction with tissue access device 240. Such a tissue modification device may be used, for example, by passing the device through shaft 242, such that a portion of the device extends out of aperture 244 to perform a procedure, while distal extension 246 protects non-target tissue from harm. In various embodiments, multiple surgical devices may be passed through and used with tissue access device 240, either serially or simultaneously, depending on the configuration of access device 240 and the constraints of the operating field and anatomy.

Figure 11:
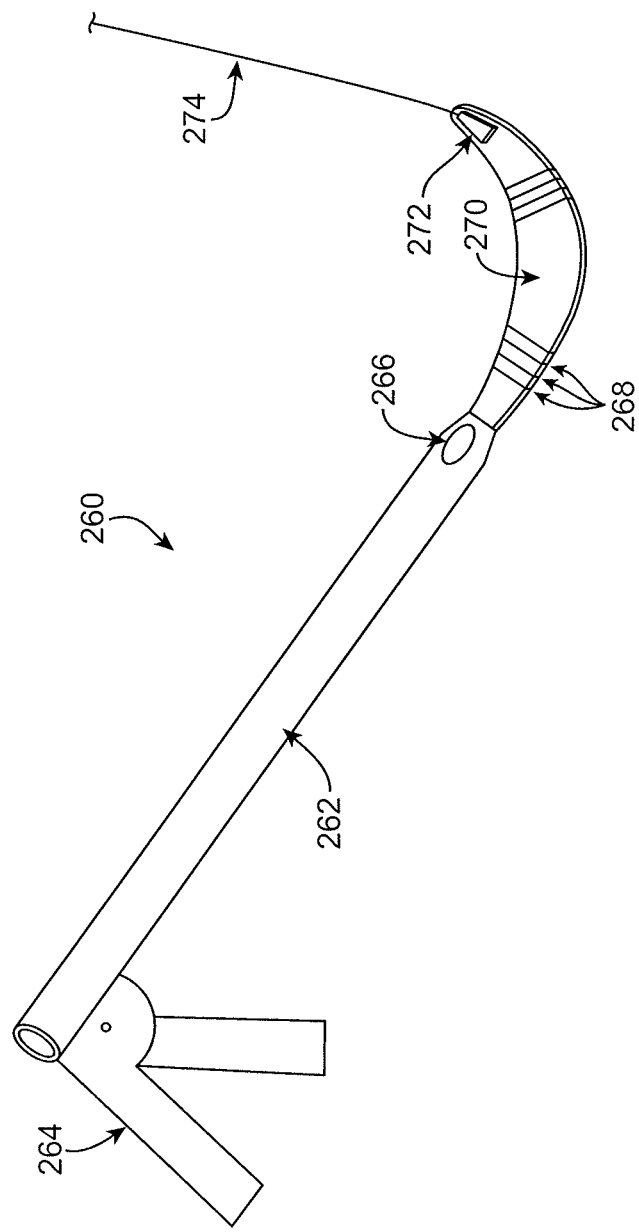
FIG. 11 is a perspective view of a tissue access device coupled with a guidewire, according to an alternative embodiment of the present invention.

Referring to FIG. 11, in another embodiment, a tissue access device 260 includes an elongate, hollow shaft 262, a handle 264, a distal aperture 266, and a distal extension 270 having flexibility slits 268 and coupled with a guidewire coupling member 272, which may be coupled with a guidewire 274. This embodiment of tissue access device 260 is similar to the one described immediately above but includes the additional feature of handle 264, which in some embodiments may be used to actuate one or more surgical/tissue modification devices passed through access device 260.

Figure 12:
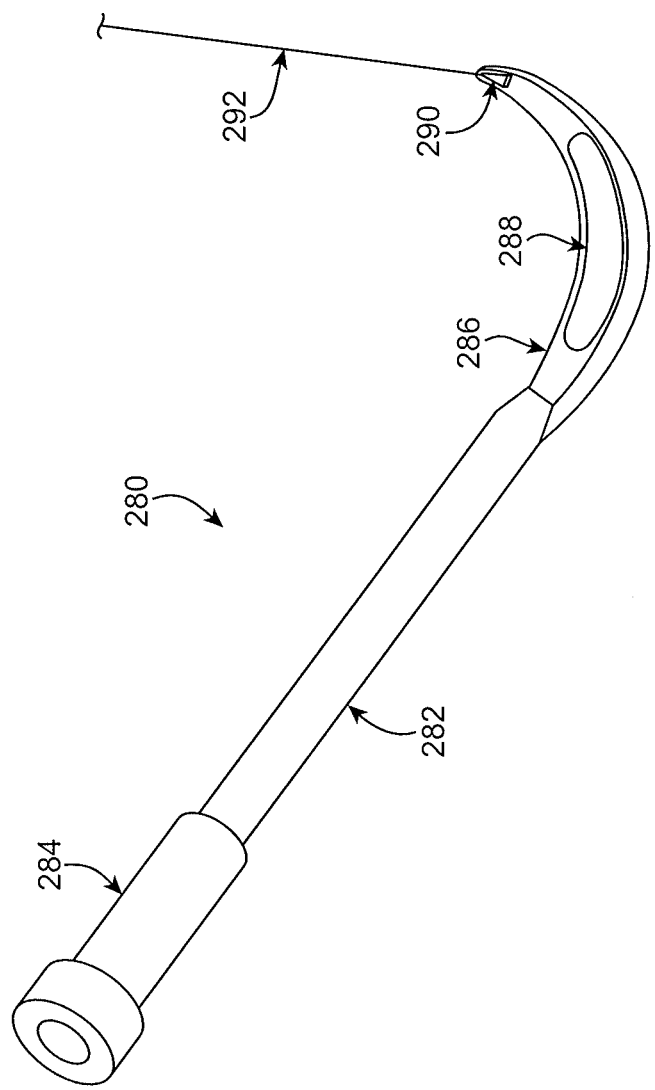
FIG. 12 is a perspective view of a tissue access device coupled with a guidewire, according to an alternative embodiment of the present invention.

FIG. 12 depicts another alternative embodiment of a tissue access device 280, including a proximal shaft portion 282, a distal shaft portion 286, and a handle 284. Distal shaft portion 286 includes a window 288, through which a portion of a surgical/tissue modification device may be exposed to perform a procedure, and a guidewire coupling member 290, which may be coupled with a guidewire 292. As with the previously described embodiments, any of a number of surgical devices may be passed through and used with tissue access device 280, according to various embodiments. Tissue modifying portions of such devices may be exposed through or may even extend out of window 288 to perform any of a number of procedures, while distal shaft portion 286 otherwise protects non-target tissue from damage. In various embodiments, shaft portions 282, 286 may both be flexible, both be rigid, or one may be flexible and the other rigid. In one embodiment, for example, shaft 282, 286 may comprise a flexible catheter, while in an alternative embodiment, shaft 282, 286 may comprise a rigid, probe-like structure.

Any of the embodiments described in FIGS. 10-12 may further optionally include one or more external support devices, which removably attach to shaft 242, 262, 282 and one or more stabilizing structures outside the patient, such as a retractor, bed rail, or the like. Such support devices, such as detachable support arms, may be provided with a tissue access device 240, 260, 280 as part of a system or kit and may be used to help support/stabilize the access device during use.

With reference now to FIGS. 13A-13D, one embodiment of a surgical device distal portion 138 with a guidewire coupling member 130 is shown in conjunction with a shaped guidewire 134. Guidewire coupling member 130 may generally include a slit 131 and a bore 132. Guidewire 134 may include a shaped member 136 at one end, which is shown as a ball-shaped member 136 but may have any of a number of suitable shapes in alternative embodiments. Generally, guidewire 134 and shaped member 136 may be made of any suitable material, such as but not limited to any of a number of metals, polymers, ceramics, or composites thereof. Suitable metals, for example, may include but are not limited to stainless steel (303, 304, 316, 316L), nickel-titanium alloy, tungsten carbide alloy, or cobalt-chromium alloy, for example, Elgiloy® (Elgin Specialty Metals, Elgin, Ill., USA), Conichrome® (Carpenter Technology, Reading, Pa., USA), or Phynox® (Imphy SA, Paris, France). Suitable polymers include but are not limited to nylon, polyester, Dacron®, polyethylene, acetal, Delrin® (DuPont, Wilmington, Del.), polycarbonate, nylon, polyetheretherketone (PEEK), and polyetherketoneketone (PEKK). Ceramics may include but are not limited to aluminas, zirconias, and carbides. Shaped member 136 may be formed by attaching a separate member to one end of guidewire 134, such as by welding, or may be formed out of the guidewire material itself.

Figure 13A:
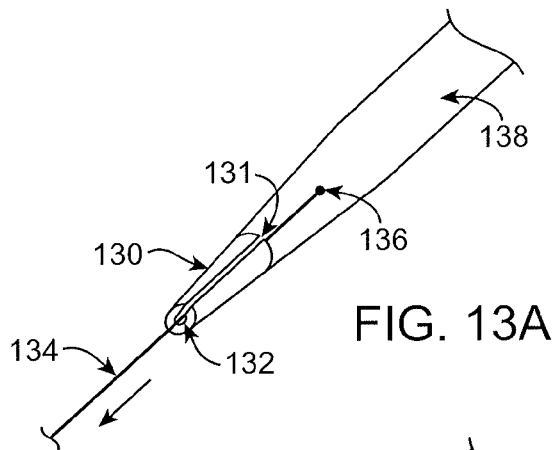
FIGS. 13A and 13C are perspective views.
Figure 13C:
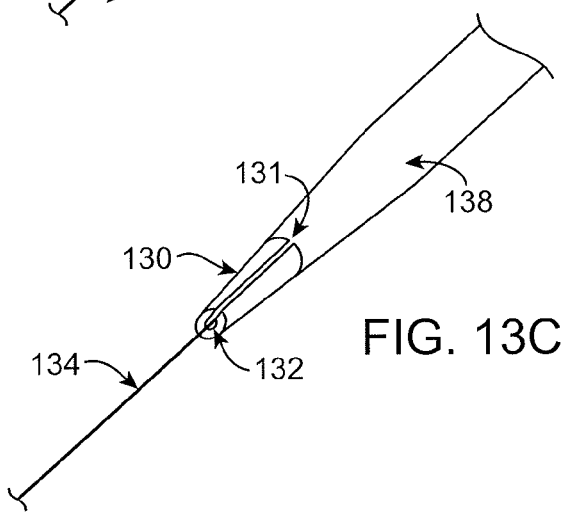
Figure 13B:
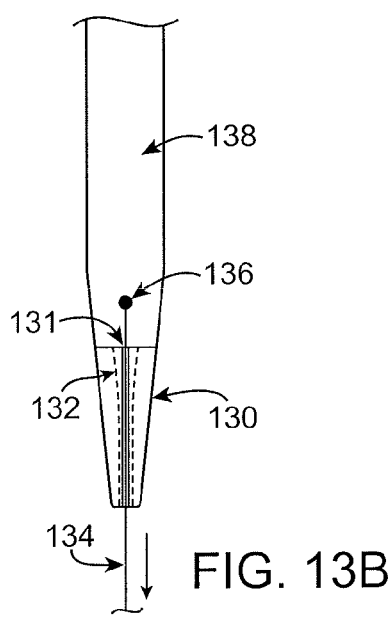
FIGS. 13B and 13D are top views, of a distal end of a tissue modification device with guidewire coupling member and a shaped guidewire, according to one embodiment of the invention.
Figure 13D:
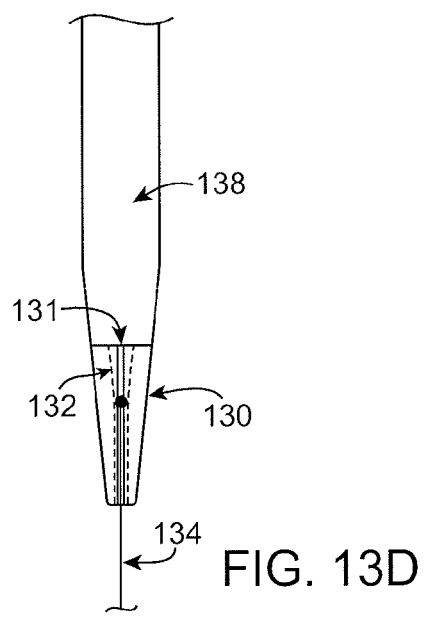

In the embodiment shown, guidewire 134 may be coupled with coupling member 130 by first placing guidewire 134 through slit 131 into bore 132, as shown in perspective view FIG. 13A and top view FIG. 13C. Guidewire 134 may then be pulled through bore 132 (solid-tipped arrows in FIGS. 13A and 13C), to pull shaped member 136 into bore 132, as shown in perspective view FIG. 13B and top view FIG. 13D. As visible in FIGS. 13B and 13D, bore 132 may be tapered, so that shaped member 136 may enter bore 132 but may only travel partway through before reaching a diameter of bore 132 through which it cannot pass. In an alternative embodiment, bore 132 may include a hard stop rather than a taper. In any case, shaped member 136 may be pulled into bore 132 to cause it to lodge there, and additional pulling or tensioning force may be applied to guidewire 134 without risk of pulling shaped member 136 farther through bore 132. Guidewire 134 may thus be used to pull surgical device 138 through tissue and into a desired position for performing a procedure, and may further be used to apply tensioning/pulling force to surgical device 138 to help urge a tissue modifying portion of device 138 against target tissues.

As with many of the embodiments described previously and hereafter, guidewire coupling member 130 may be either attached to or formed as an integral part of surgical device distal portion 138, according to various embodiments. Coupling member 130 may be made of any suitable material, as has been mentioned previously, and may have any desired dimensions and any of a number of different configurations, some of which are described in further detail below. In various embodiments, coupling member 130 may be attached to an extreme distal end of surgical device 138 or may be positioned at or near the extreme distal end. Although coupling member 130 is typically attached to or extending from a top or upper surface of surgical device 138, in some embodiments it may alternatively be positioned on a bottom/lower surface or other surface.

Figure 14A:
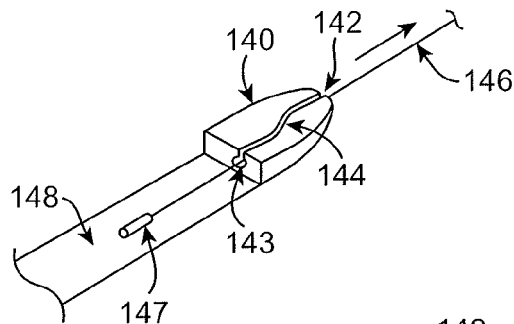
FIGS. 14A and 14B are perspective views of a distal end of a tissue modification device with guidewire coupling member and a shaped guidewire, according to an alternative embodiment of the invention.
Figure 14B:
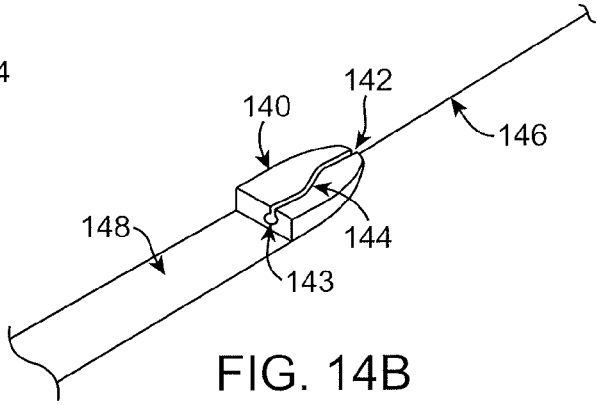

In another embodiment, and with reference now to FIGS. 14A and 14B, a guidewire coupling member 140 including a slit 142 with one or more curves 144 and a bore 143 may be attached to a surgical device distal portion 148. A guidewire 146 having a cylindrical shaped member 147 at one end may be placed through slit 142 into bore 143 and pulled distally (solid-tipped arrow), as shown in FIG. 14A. When shaped member 147 is pulled into bore 143, it is stopped by, and cannot pass through, curves 144, thus allowing guidewire 146 to be used to pull device 148 into place between target and non-target tissues and apply tensioning force.

Figure 15A:
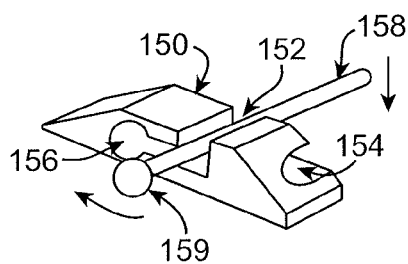
FIGS. 15A and 15C are perspective views of a guidewire coupling member and a shaped guidewire, demonstrating a method for coupling the two, according to one embodiment of the present invention.
Figure 15C:
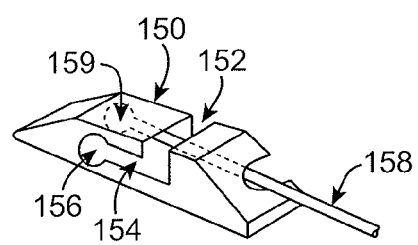
Figure 15E:
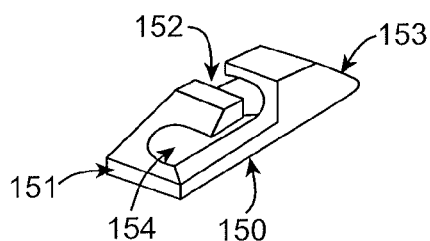
FIGS. 15E and 15F are different perspective views of the guidewire coupling member of FIGS. 15A and 15C, without the shaped guidewire.
Figure 15F:
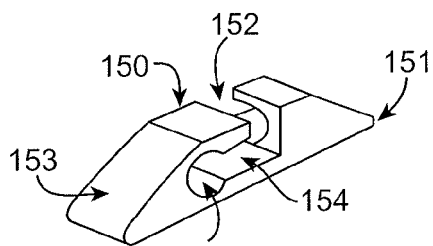

Referring to FIGS. 15A-15F, an alternative embodiment of a guidewire coupling member 150 is shown with a shaped guidewire 158. Guidewire coupling member 150 may include a transverse slit 152, an axial channel 154 and a transverse bore 156. FIG. 15E shows a front perspective view of coupling member 150, where member 150 would be mounted on a surgical device such that a front side 151 would face distally and a back side 153 would face proximally. FIG. 15F shows a rear perspective view of coupling member 150 with back side 153 and front side 151.

Figure 15B:
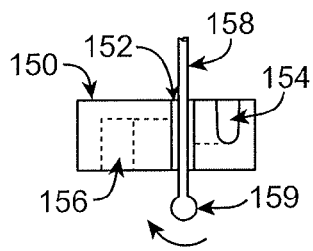
FIGS. 15B and 15D are top views of the guidewire coupling member and shaped guidewire of FIGS. 15A and 15C.
Figure 15D:
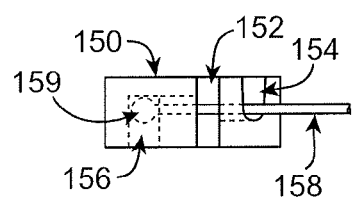

FIG. 15A is a rear/left perspective view, and FIG. 15B is a top view, both showing guidewire 158 with a ball-shaped member 159 being placed through transverse slit 152 into channel 154. Channel 154 is generally an open portion within coupling member 150, having a diameter similar to or the same as that of slit 152, to allow guidewire 158 to be rotated through coupling member 150, as depicted by the solid-tipped, curved arrow in FIGS. 15A and 15B. Bore 159 is sized to allow ball-shaped member 159 to travel into it to rest within coupling member 150, as shown in FIGS. 15C and 15D. Ball-shaped member 159 is sized such that, when shaped guidewire 158 is rotated into position within coupling member 150, it cannot travel through channel 154, and is thus trapped within bore 156. Guidewire 158 may thus be pulled, to pull a device into position and/or to apply tension to the device, without guidewire 158 pulling out of coupling member 150. Guidewire 158 may be disengaged from coupling member 150 by rotating guidewire 158, coupling member 150 or both, to release shaped member 159 from bore 156. In one embodiment, coupling member 150 may be attached to a top surface of a distal portion of a surgical device, such as by welding, adhesive or other attachment means.

An alternative embodiment of a guidewire coupling member 160 is depicted in FIGS. 16A-16E. In this embodiment, guidewire coupling member 160 includes a channel 162, a central bore 164 and a side channel, as shown in perspective view FIG. 16A, top view FIG. 16B and side view FIG. 16C. Channel 162 is generally shaped and sized to allow a shaped member 169 of a guidewire 168 to pass longitudinally therethrough. Central bore 164 is shaped and sized to allow shaped member 169 to rotate within bore 164. Side channel 166 is shaped and sized to allow guidewire 168 to pass therethrough when guidewire 168 is rotated about an axis through shaped member 169. An angle 165 formed by channel 162 and an opposite end of side channel 166 may be any desired angle, in various embodiments. For example, the angle in the embodiment shown (best seen in FIGS. 16B, 16D and 16E) is approximately 90 degrees. In alternative embodiments, the angle could instead be less than 90 degrees or greater than 90 degrees. In one embodiment, for example, an angle of about 135 degrees may be used, while in another embodiment, an angle of about 180 degrees may be used.

Figure 16B:
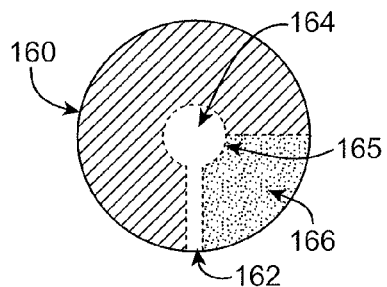
FIGS. 16A-16C are perspective, top and side views, respectively, of a guidewire coupling member, according to an alternative embodiment of the present invention.
Figure 16C:
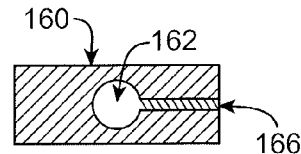
Figure 16D:
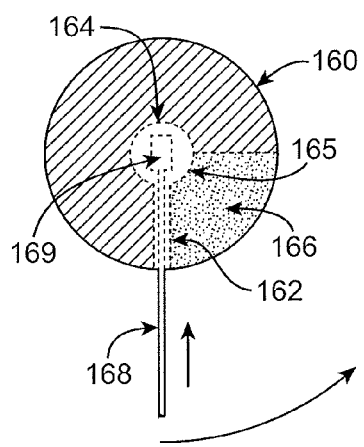
FIGS. 16D and 16E are top views of the guidewire coupling member of FIGS. 16A-16C and a shaped guidewire, demonstrating a method for coupling the coupling member with a shaped guidewire, according to one embodiment of the present invention.
Figure 16E:
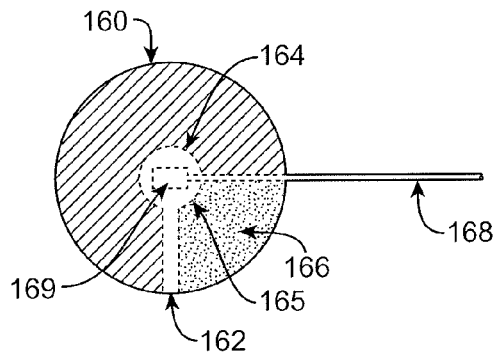
Figure 16A:
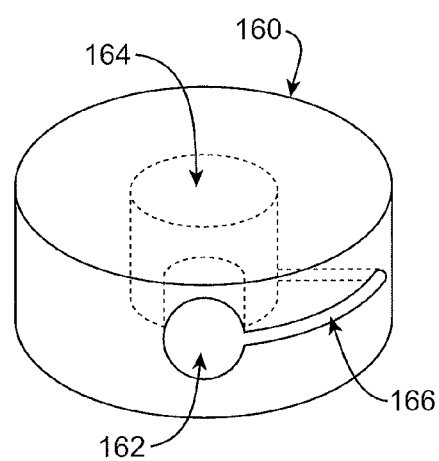

As depicted in FIG. 16D, shaped member 169 of guidewire 168 may be passed through channel 162 and into central bore 164 (hollow-tipped arrow). Guidewire 168 may then be rotated about an axis approximately through shaped member 169 (solid-tipped, curved arrow). When rotated, guidewire 168 passes through side channel 166 to its end, as shown in FIG. 16E. Guidewire 168 may then be pulled, to pull a device attached to coupling member 160 to a desired position in a patient's body, such as between target and non-target tissues. Rotated shaped member 169 is trapped within central bore 164, due to its shape and size, and cannot pass into either side channel 166 or channel 162. To remove guidewire 168 from coupling member 160, guidewire 168 may be rotated back to the position shown in FIG. 16D and withdrawn from coupling member 160 through channel 162.

Figure 17A:
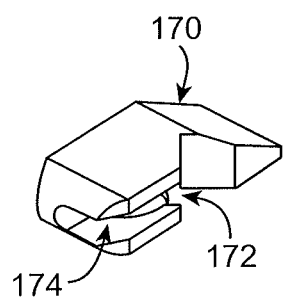
FIGS. 17A and 17B are perspective views of a guidewire coupling member, according to an alternative embodiment of the present invention.
Figure 17B:
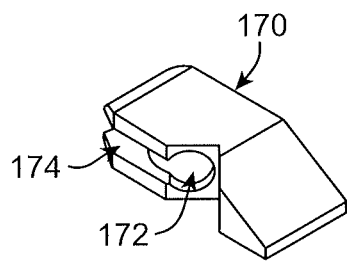
Figure 17C:
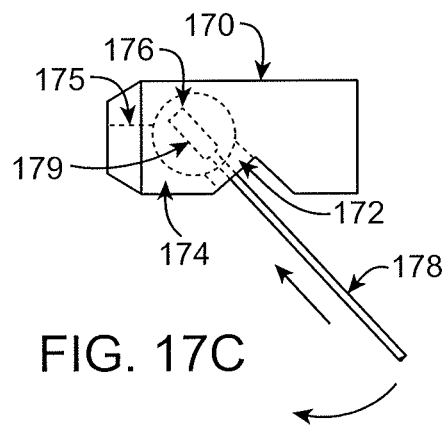
FIGS. 17C and 17D are top views of the guidewire coupling member of FIGS. 17A and 17B and a shaped guidewire, demonstrating a method for coupling the coupling member with the guidewire, according to one embodiment of the present invention.
Figure 17D:
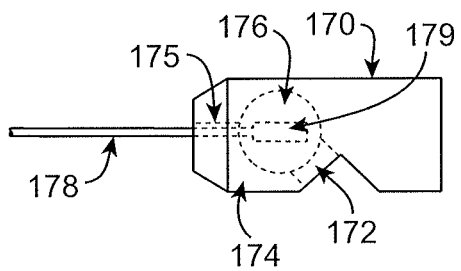

Referring now to FIGS. 17A-17D, another alternative embodiment of a guidewire coupling member 170 is shown. FIGS. 17A and 17B are front perspective and rear perspective views, respectively, in which a channel 172 and a side channel 174 of coupling member 170 may be seen. FIGS. 17C and 17D are top views, showing coupling member 170 with an inserted guidewire 178. As seen in FIG. 17C, guidewire 178 with a shaped distal member 179 may be advanced through channel 172 (hollow-tipped arrow), to position shaped member 179 in a central bore 176 of coupling member 170. Guidewire 178 may then be rotated through side channel 174 about an axis approximately about shaped member 179 (solid-tipped, curved arrow). As shown in FIG. 17D, guidewire 178 may be rotated until it hits an end 175 of side channel 174. Guidewire 178 may then be pulled to pull a device attached to coupling member 170, as shaped member 179 will be trapped within central bore 176, due to it shape and size. When desired, guidewire 178 may be removed from coupling member 170 by rotating guidewire 178 back to the position shown in FIG. 17C and withdrawing it through channel 172. Channel 172 may be located at any desired angle, relative to end 175 of side channel 174. In the embodiment shown, for example, the angle is approximately 135 degrees. As in the embodiment described immediately above, channel 172 is generally shaped and sized to allow shaped member 179 to pass longitudinally therethrough, central bore 176 is shaped and sized to allow shaped member 179 to rotate within bore 176, and side channel 174 is shaped and sized to allow guidewire 178 to pass therethrough when guidewire 178 is rotated.

Turning to FIGS. 18A and 18B, in another alternative embodiment, a guidewire coupling member may include a cam 300 and a stationary portion 306 (only a part of which is shown). Cam may 300 rotate about an axis 302 from an open position (FIG. 18A), which allows a guidewire 304 to pass through, to a closed position (FIG. 18B), which traps guidewire 304 against stationary portion 306. In one embodiment, cam 300 may automatically move from open to closed positions as guidewire 304 is advanced (hollow-tipped arrow in FIG. 18A) and may move from closed to open positions as guidewire 304 is retracted. Some embodiments of a coupling member, such as that shown in FIGS. 18A and 18B, may be used with a guidewire 304 that does not have a shaped member on its proximal end. Alternatively, such a coupling member may also be used with a shaped guidewire.

FIG. 19 shows an alternative embodiment of a guidewire coupling member, which includes two opposing cams 310 that rotate toward one another (curved arrows) to grip and hold a guidewire 312. As with the previous embodiment, this coupling member may be used, in various embodiments, either with a guidewire having a shaped proximal end or an unshaped guidewire 312.

Referring now to FIGS. 20A-20C, in another embodiment, a guidewire coupling member 320 (shown in top view) may include three movable rollers 322. In an open position, as in FIG. 20A, rollers 322 may be arrayed to allow a guidewire 324 to pass through them. Rollers 322 may be moved, relative to one another (solid-tipped arrows), to partially constrain guidewire 324 (FIG. 20B) or to completely constrain guidewire 324 (FIG. 20C). Rollers 322 may be moved back to the open position (FIG. 20A) to release guidewire 324.

Figure 21C:
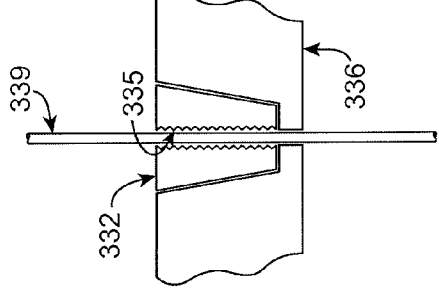
FIGS. 21B and 21C are side cross-sectional views, of a split-cone guidewire coupling member, according to an alternative embodiment of the present invention.
Figure 21B:
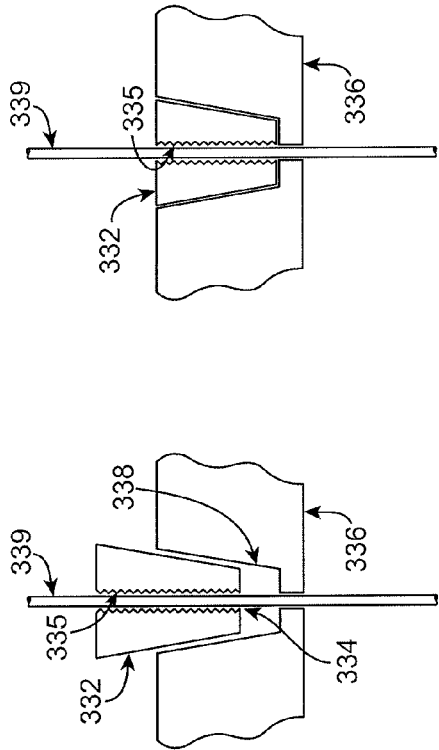
Figure 21A:
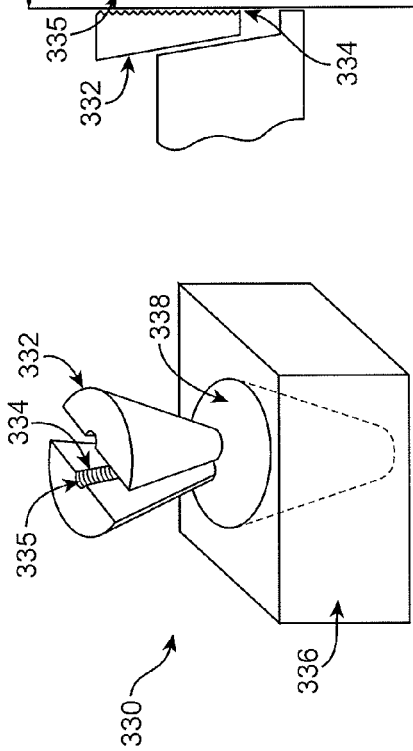
FIG. 21A is a perspective view.

In an alternative embodiment, and referring now to FIGS. 21A-21C, a guidewire coupling member 330 may include a multi-piece cone 332 having a core 334 with a textured inner surface 335, and a stationary portion 336 having a receptacle 338 for receiving cone 332. In an open position, as in FIG. 21B, the two halves of cone 332 are separated and not wedged into receptacle 338, so that a guidewire 339 may be passed through core 334. Cone 332 may be moved to a closed position, as in FIG. 21C, to grip guidewire 339 with textured surface 335 and prevent guidewire 339 from moving further through core 334. In one embodiment, for example, as guidewire 339 moves through core 334, it may generate friction with textured surface 335 and thus pull cone 332 into receptacle. As with several previous embodiments, guidewire 339 may either include a proximal shaped member or may not include such a member, in various embodiments.

Figure 22:
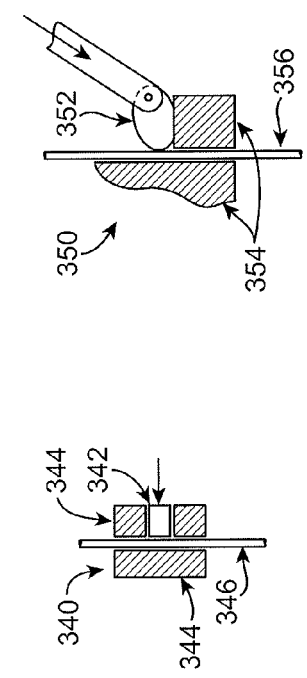
FIG. 22 is a top view of a flat anvil guidewire coupling member, according to an alternative embodiment of the present invention.
Figures 25A, 25B:
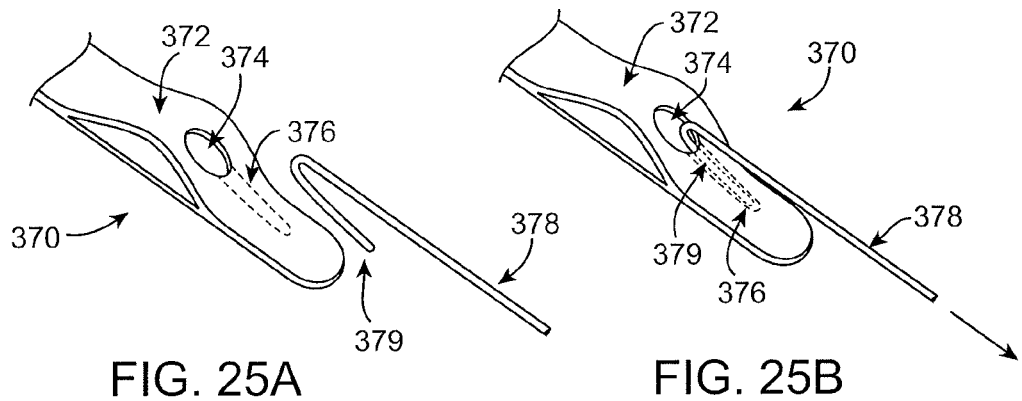
FIGS. 25A and 25B are perspective views of a hooked guidewire and receiving guidewire coupling member, according to an alternative embodiment of the present invention.
Figures 26A, 26B:
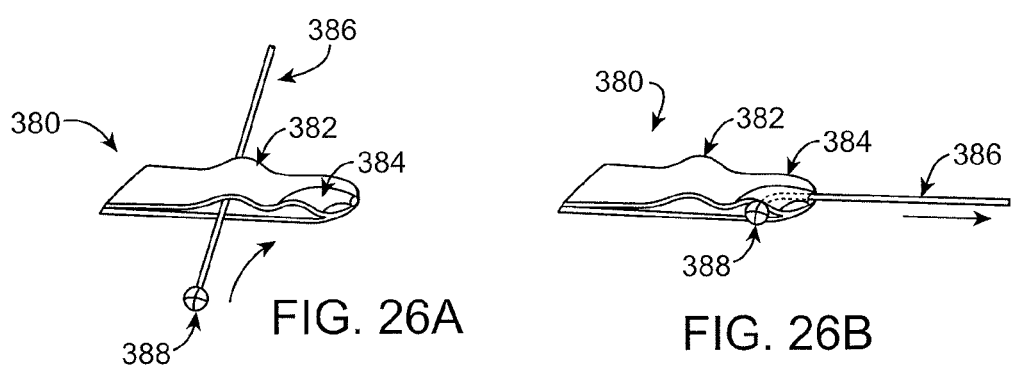
FIGS. 26A and 26B are perspective views of a ball-and-socket guidewire and guidewire coupling member, according to an alternative embodiment of the present invention.

With reference now to FIG. 22, in another embodiment, a guidewire coupling member 340 may include a flat anvil 342 and one or more stationary portions 344. Anvil may be moved (hollow-tipped arrow) to pinch a guidewire 344 between itself and stationary portion 344.

Figure 23:
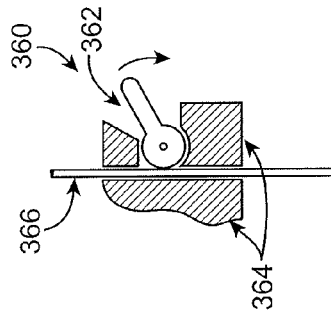
FIG. 23 is a top view of a corner pinch guidewire coupling member, according to an alternative embodiment of the present invention.

In an alternative embodiment, shown in FIG. 23, a guidewire coupling member 350 may include a corner-pinch mechanism 352 and one or more stationary portions 354. Mechanism 352 may be advanced (hollow-tipped arrow) to pinch guidewire 356 against stationary member 354 and thus prevent it from moving further through coupling device 350.

Figure 24:
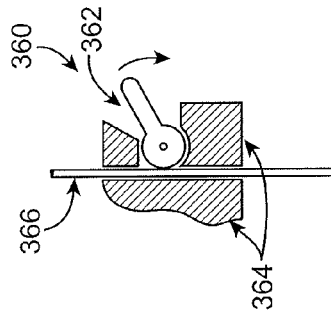
FIG. 24 is a top view of an eccentric cam guidewire coupling member, according to an alternative embodiment of the present invention.

Referring to FIG. 24, another embodiment of a guidewire coupling member 360 is shown, which includes an eccentric cam 362 that rotates (hollow-tipped arrow) to pinch a guidewire 366 between itself and a stationary portion 364.

Figures 27A, 27B:
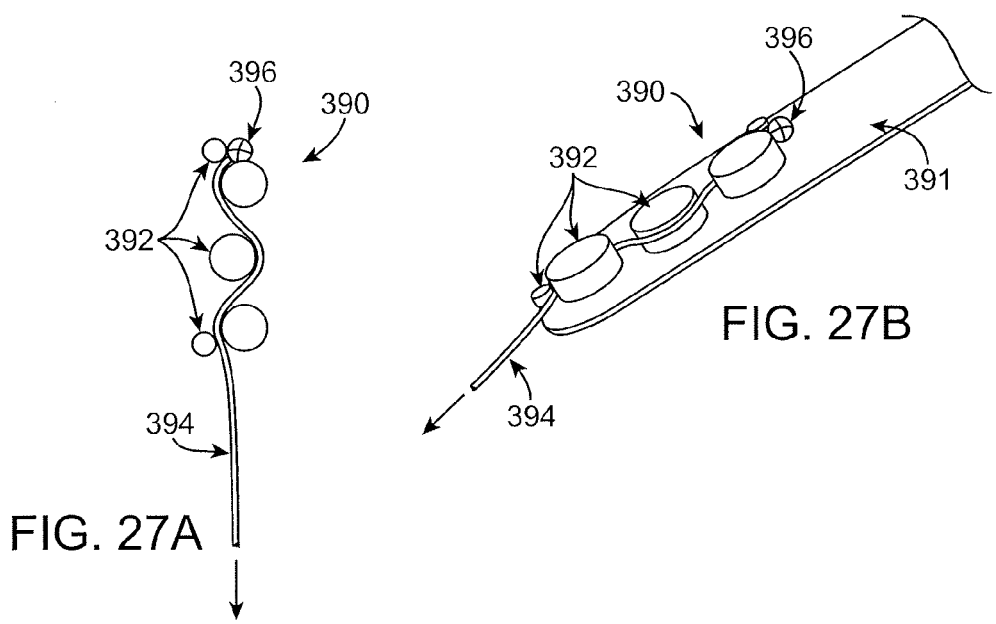
FIGS. 27A and 27B are top and perspective views, respectively, of a spool trap guidewire coupling member, according to an alternative embodiment of the present invention.

In another embodiment, with reference to FIGS. 27A and 27B, a guidewire coupling member 390 may include multiple spools 392, through which a guidewire 394 may pass, until a shaped member 396 on one end of guidewire 394 gets caught. FIG. 27B shows coupling member 390 attached with an upper surface of a surgical device distal end 391.

Figure 28A:
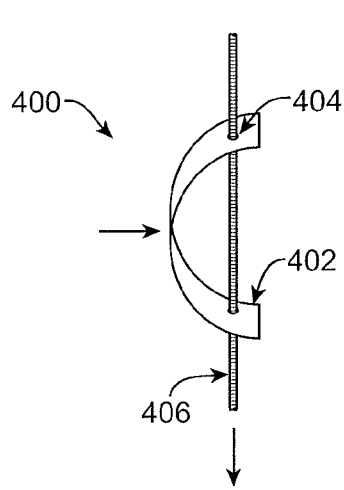
FIGS. 28A and 28B are side views of a semicircular ribbon guidewire coupling member with textured guidewire, according to an alternative embodiment of the present invention.
Figure 28B:
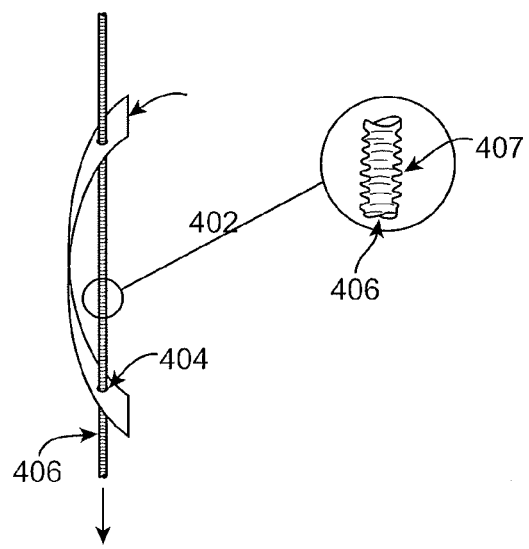

In yet another embodiment, and with reference now to FIGS. 28A and 28B, a guidewire coupling member 400 may include a semi-circular ribbon 402 having two apertures 404. With this embodiment of coupling member 400 (as well as other embodiment described herein), a textured guidewire 406 may be used. As textured guidewire 406 passes through apertures 404, friction caused by the textured surface 407 causes ribbon 402 to flatten (FIG. 28B), thus trapping guidewire 406 in apertures 404. Ribbon 402 may be made of metal or any other suitable material, examples of which have been listed previously.

Figure 29:
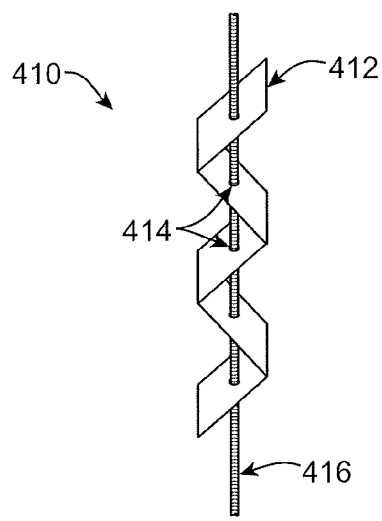
FIG. 29 is a side view of a folded ribbon guidewire coupling member with textured guidewire, according to an alternative embodiment of the present invention.

Referring to FIG. 29, another alternative embodiment is shown, in which a guidewire coupling member 410 includes a folded ribbon 412 having multiple apertures 414. Ribbon 412 may flatten as a textured guidewire 416 passes through it, thus causing apertures to trap guidewire 416.

Figure 30:
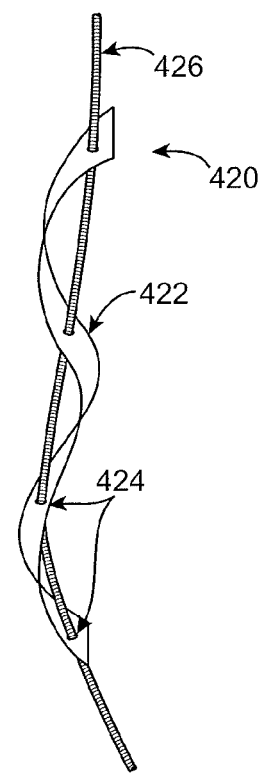
FIG. 30 is a side view of a ribbon guidewire coupling member, according to an alternative embodiment of the present invention.

Another embodiment of a guidewire coupling member 420 is shown in FIG. 30. In this embodiment, coupling member 420 includes a curved ribbon 422 with multiple apertures 424. Ribbon 422 may flatten to constrain a guidewire 426 in apertures 424, as with the previously described embodiments. Some embodiments of such ribbon-shaped coupling members 400, 410, 420 may function with a non-textured guidewire as well as, or in place of, a textured guidewire.

Figure 31:
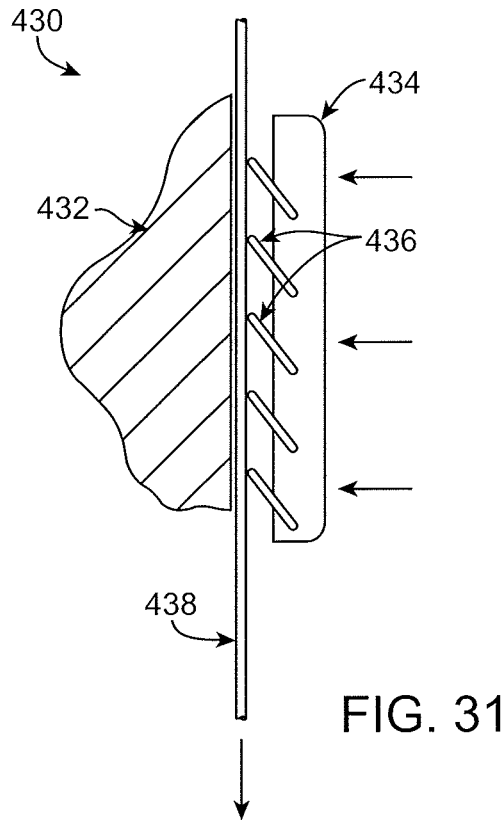
FIG. 31 is a side view of a multi-point guidewire coupling member, according to one embodiment of the present invention.

Referring to FIG. 31, in another embodiment, a guidewire coupling member 430 for removably coupling with a guidewire 438 may include a stationary portion 432 and a movable portion 434. Movable portion 434 may include multiple contact members 436 or locking edges, configured to hold guidewire 438 when movable portion 434 is pushed against it (hollow-tipped arrows). Movable portion 434 may be moved using any suitable technique or means in various embodiments. Contact members 436 generally press guidewire 438 against stationary portion 432 such that it will not move through coupling member 430 when pulled (solid-tipped arrow), thus allowing a device coupled with coupling member 430 to be pulled using guidewire 438.

Figure 32:
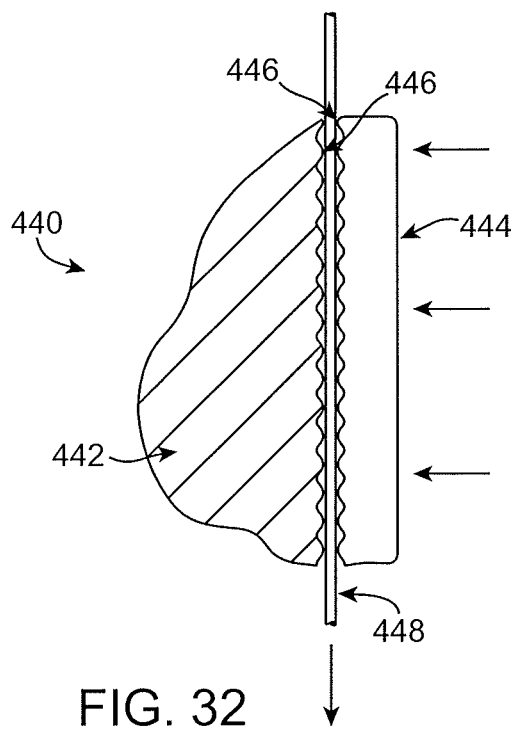
FIG. 32 is a side view of a rough-surface guidewire coupling member, according to one embodiment of the present invention.

In another embodiment, and with reference now to FIG. 32, a guidewire coupling member 440 may include a stationary portion 442 and a movable portion 444, each of which has a roughened surface 446 facing one another. Movable portion 444 may be moved toward stationary portion 442 (hollow-tipped arrows) to trap guidewire 446 in between, thus preventing guidewire 446 from moving through coupling member 440 and thus allowing a device coupled with coupling member 440 to be pulled via guidewire 448.

Turning to FIGS. 33A-33D, several alternative embodiments of a guidewire for use with various embodiments of a guidewire coupling member and guidewire system are shown. In some embodiments of a guidewire system, any of a number of currently available guidewires may be used. In other embodiments, a textured guidewire without a shaped member on either end may be used. Each of the embodiments shown in FIGS. 33A-33D, by contrast, has some kind of shaped member on a proximal end of the guidewire for coupling with a guidewire coupling member and some kind of sharpened or otherwise shaped distal tip for facilitating passage of the guidewire through tissue.

In various embodiments, guidewires may comprise a solid wire, a braided wire, a core with an outer covering or the like, and may be made of any suitable material. For example, in one embodiment, a guidewire may be made of Nitinol. In various alternative embodiments, guidewires may be made from any of a number of metals, polymers, ceramics, or composites thereof. Suitable metals, for example, may include but are not limited to stainless steel (303, 304, 316, 316L), nickel-titanium alloy, tungsten carbide alloy, or cobalt-chromium alloy, for example, Elgiloy® (Elgin Specialty Metals, Elgin, Ill., USA), Conichrome® (Carpenter Technology, Reading, Pa., USA), or Phynox® (Imphy SA, Paris, France). In some embodiments, materials for guidewires or for portions or coatings of guidewires may be chosen for their electrically conductive or thermally resistive properties. Suitable polymers include but are not limited to nylon, polyester, Dacron®, polyethylene, acetal, Delrin® (DuPont, Wilmington, Del.), polycarbonate, nylon, polyetheretherketone (PEEK), and polyetherketoneketone (PEKK). In some embodiments, polymers may be glass-filled to add strength and stiffness. Ceramics may include but are not limited to aluminas, zirconias, and carbides.

Figure 33A:
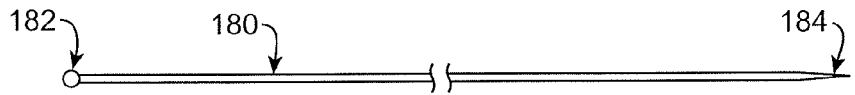
FIGS. 33A-33D are side views of proximal and distal ends of various guidewires, according to various embodiments of the present invention.
Figure 33B:
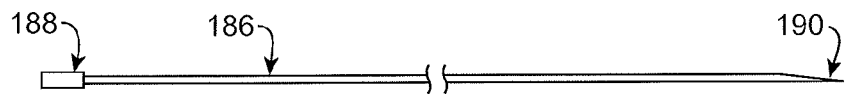
Figure 33C:
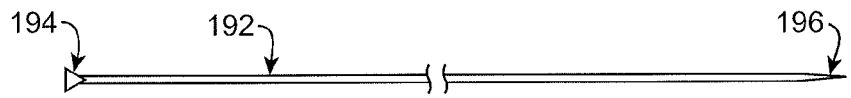
Figure 33D:
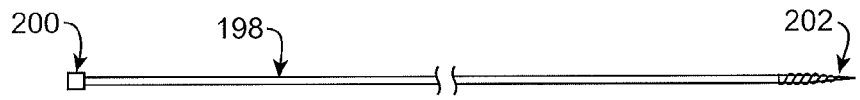

In the embodiment shown in FIG. 33A, a guidewire 180 includes a ball-like shaped member 182 attached to its proximal end and a pointed distal tip 184. As with all the following exemplary embodiments, shaped member 182 may be either a separate piece attached to guidewire 180 by welding or other means or may be a proximal end of guidewire 180, formed into shaped member 182. FIG. 33B shows a guidewire 186 with a cylindrical shaped member 188 and a beveled distal tip 190. FIG. 33C shows a guidewire 192 with a pyramidal shaped member 194 and a double-beveled distal tip 196. FIG. 33D shows a guidewire 198 with a cubic shaped member 200 and a threaded distal tip 202. In alternative embodiments, any of the shaped members 182, 188, 194, 200 may be combined with any of the distal tips 184, 190, 196, 202. In yet other alternative embodiments, the shaped members and/or distal tips may have other shapes and/or sizes. Thus, the embodiments shown in FIGS. 33A-33D are provided primarily for exemplary purposes and should not be interpreted to limit the scope of the invention as it is described by the claims.

Figure 34A:
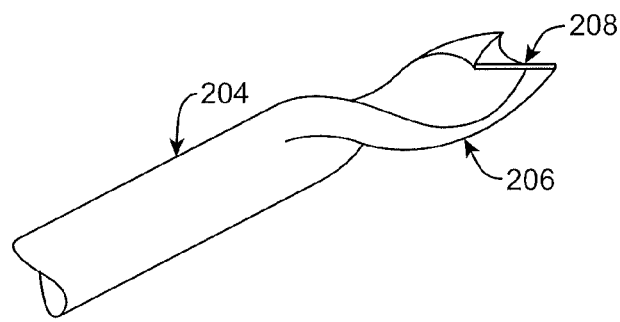
FIG. 34A is a perspective view of a drill-shaped distal end of a guidewire, according to one embodiment of the present invention.
Figure 34B:
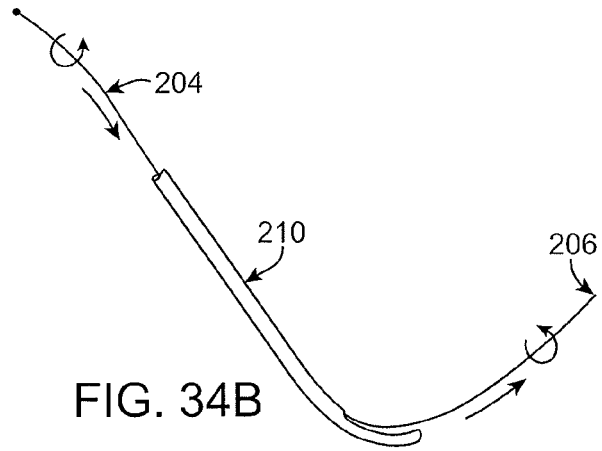
FIG. 34B is a side view of a guidewire as in FIG. 34A, being passed through a probe device.

Referring now to FIGS. 34A and 34B, another embodiment of a guidewire 204 may include a drill-shaped distal tip 206 with a cutting edge 208. Such a drill-shaped tip 206 may facilitate passage of guidewire 204 through tissue, as shown in FIG. 34B. Guidewire 204 may be advanced through a probe 210 and through tissue (not shown) by simultaneously pushing (solid-tipped, straight arrows) and twisting (hollow-tipped, curved arrows) guidewire 204 from its proximal end. Drill-shaped tip 206 may facilitate passage of guidewire 204 through tissue by acting as a drill.

Figure 35A:
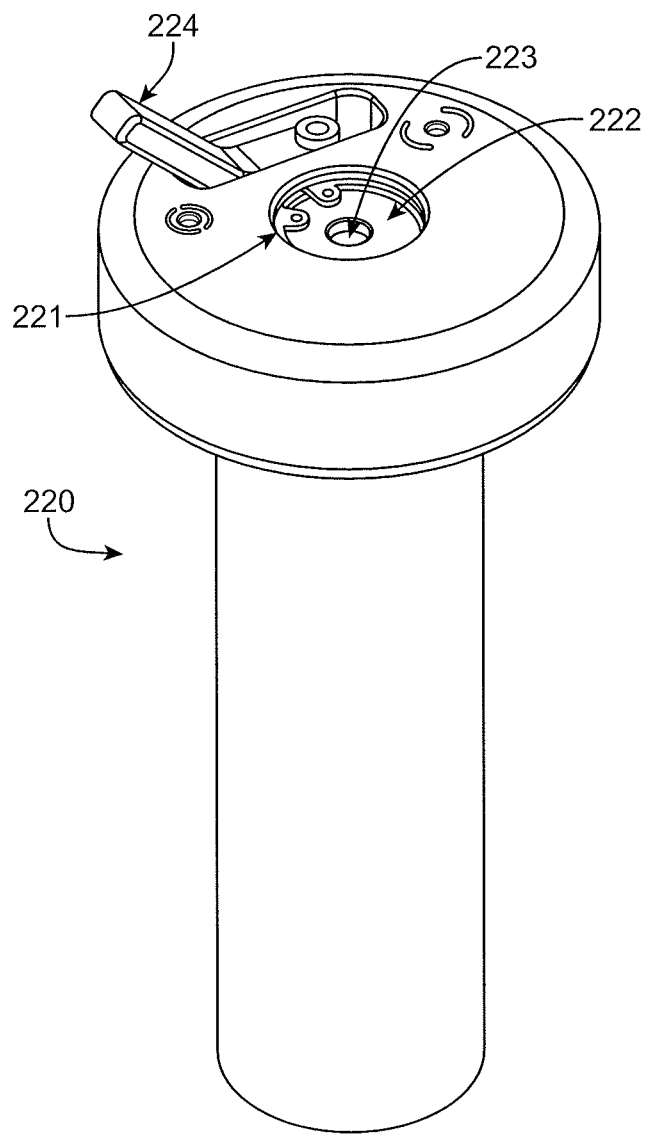
FIGS. 35A and 35B are perspective and exploded views of a handle for grasping a guidewire, according to one embodiment of the present invention.

With reference to FIG. 35A, in some embodiments, a guidewire system may include a guidewire handle 220 for grasping a guidewire outside the patient. Such a guidewire handle 220 may include, for example, a guidewire clamping mechanism 222 housed in a central, longitudinal bore 221 of handle 220 and including a central guidewire aperture 223. Handle 220 may also include a lock lever 224 for tightening clamping mechanism 222 around a guidewire. At some points in the present application, handles similar to handle 220 are referred to as "distal handles," and handles coupled with various tissue modification devices are referred to as "proximal handles." These terms, "distal" and "proximal," are generally used to distinguish the two types of handles and to denote that one is more proximal than the other, during use, to a first incision or entry point into a patient, through which a guidewire system is placed and then used to pull a tissue modification device into position in the patient. "Distal" and "proximal," however, are used merely for clarification and do not refer to the relation of any device to specific anatomical structures, the position of a physician/user of the described devices/systems, or the like. Thus, in various embodiments, either type of handle may be "distal" or "proximal" relative to various structures, users or the like. For the purposes of FIGS. 35A and 35B, the embodiment is described as guidewire handle 220, denoting its function of holding a guidewire.

Figure 35B:
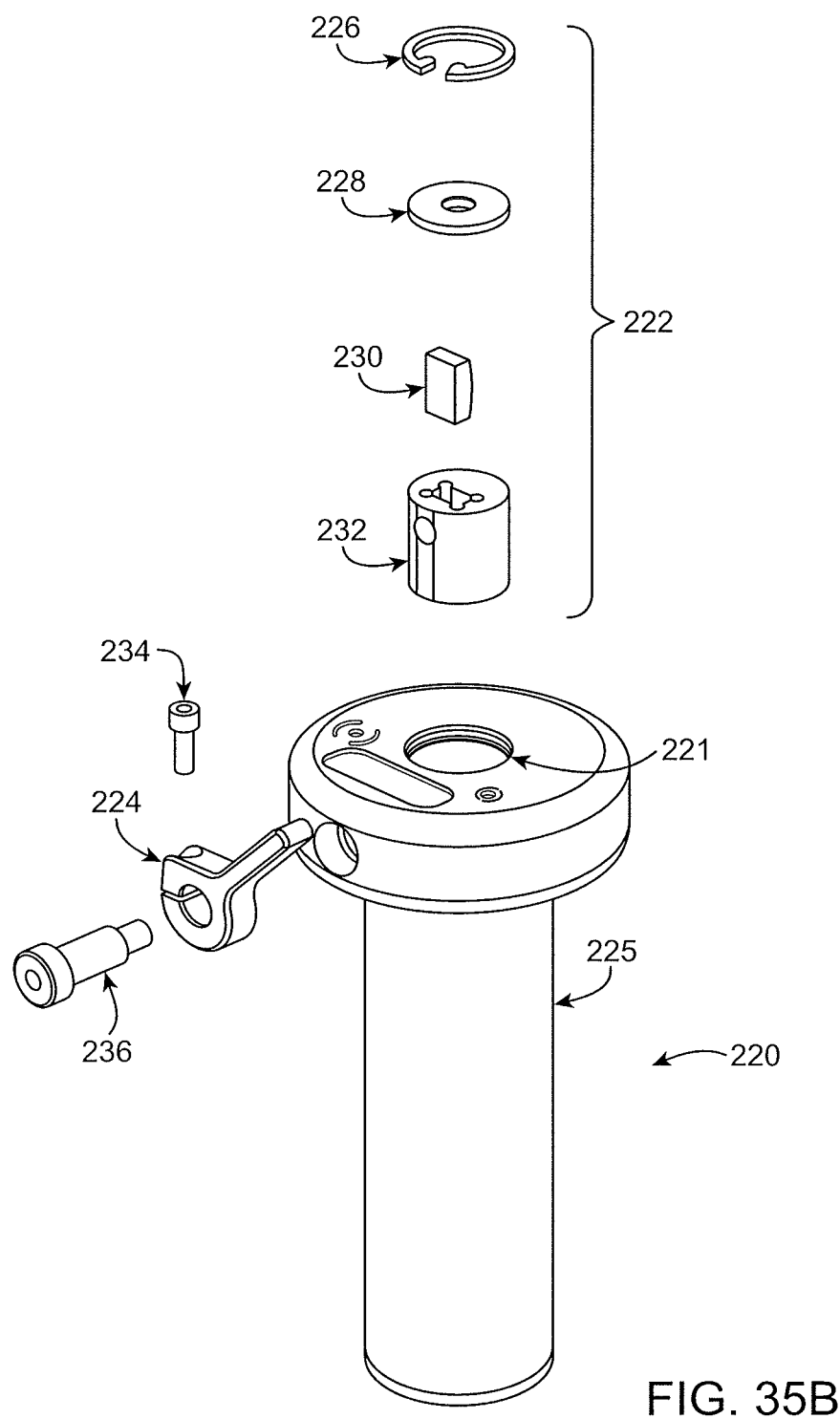

FIG. 35B provides an exploded view guidewire handle 220. A handle body 225 may be made of any suitable material and have any desired shape and size. In various alternative embodiments, for example, handle body 220 may be made from any of a number of metals, polymers, ceramics, or composites thereof. Suitable metals, for example, may include but are not limited to stainless steel (303, 304, 316, 316L), nickel-titanium alloy, tungsten carbide alloy, or cobalt-chromium alloy, for example, Elgiloy® (Elgin Specialty Metals, Elgin, Ill., USA), Conichrome® (Carpenter Technology, Reading, Pa., USA), or Phynox® (Imphy SA, Paris, France). Suitable polymers include but are not limited to nylon, polyester, Dacron®, polyethylene, acetal, Delrin® (DuPont, Wilmington, Del.), polycarbonate, nylon, polyetheretherketone (PEEK), and polyetherketoneketone (PEKK). Ceramics may include but are not limited to aluminas, zirconias, and carbides.

Clamping mechanism 222 may include, for example, a snap ring 226, a keeper washer 228, a flat anvil 230, and a cage barrel 232, all of which fit within central bore 221 of handle body 225. Lock lever 224 may be coupled with a pinch screw 234 and a shoulder screw 236. When lock lever 224 is turned in one direction, it pushes shoulder screw 236 against clamping mechanism 222 to cause mechanism 222 to clamp down on a guidewire. Lock lever 224 may be turned in an opposite direction to loosen clamping mechanism 222, thus allowing a guidewire to be introduced into or release from central guidewire aperture 223.

Although various illustrative embodiments are described above, any of a number of changes may be made to various embodiments without departing from the scope of the invention as described by the claims. For example, the order in which various described method steps are performed may often be changed in alternative embodiments, and in other alternative embodiments one or more method steps may be skipped altogether. Optional features of various device and system embodiments may be included in some embodiments and not in others. Therefore, the foregoing description is provided primarily for exemplary purposes and should not be interpreted to limit the scope of the invention as it is set forth in the claims.

What we claim is:

1. A device for guiding a surgical device to a desired position in a human body, the device comprising:
    an elongate body having a proximal end and a flat, thin and flexible distal end region, wherein the distal end region comprises an abrasive member on one side; and
    a coupling member disposed at or near the distal end, wherein the coupling member is configured to receive a guidewire to secure the guidewire and the elongate body together in an end-to-end configuration to allow the distal end of the elongate body to be pulled distally by axial tension of the guidewire,
    wherein the coupling member applies an increasing securing force to the guidewire as the guidewire moves distally through the coupling member.

2. The device of claim 1, wherein the distal end of the elongate body is tapered.

3. The device of claim 1, wherein the proximal end of the elongate body is rigid.

4. The device of claim 1, wherein a bore region within the coupling member is tapered.

5. The device of claim 1, wherein the coupling member comprises a longitudinal slit extending distally to proximally.

6. The device of claim 1, further comprising a guidewire having a proximal end and a sharp and tissue penetrating distal end and a shaped element at the proximal end, wherein the shaped element comprises a profile that is larger than a region of the guidewire located distal to the shaped element.

7. The device of claim 6, wherein the shaped element has a shape selected from the group consisting of a ball, a cylinder, a teardrop, a cube, a pyramid, a diamond and a hook.

8. The device of claim 6, wherein the sharpened distal tip has a shape selected from the group consisting of pointed, beveled, double-beveled, drill-tip shaped, and corkscrew.

9. A device for guiding a surgical device to a desired position in a human body, the device comprising:
    an elongate body having a proximal end and a thin and flexible distal end region, wherein the distal end region comprises an abrasive or cutting member; and
    a coupling member disposed at or near the distal end, wherein the coupling member is configured to receive a guidewire and to secure the guidewire and the elongate body together in an end-to-end configuration to allow the distal end of the elongate body to be pulled distally by pulling the guidewire distally to axially tension the guidewire,
    wherein the coupling member applies an increasing securing force to the guidewire as the guidewire moves distally through the coupling member.

10. The device of claim 9, wherein the distal end of the elongate body is tapered.

11. The device of claim 9, wherein the proximal end of the elongate body is rigid.

12. The device of claim 9, wherein a bore region within the coupling member is tapered.

13. The device of claim 9, wherein the coupling member comprises a longitudinal slit extending distally to proximally.

14. The device of claim 9, further comprising a guidewire having a proximal end and a sharp and tissue penetrating distal end and a shaped element at the proximal end, wherein the shaped element comprises a profile that is larger than a region of the guidewire located distal to the shaped element.

15. The device of claim 14, wherein the shaped element has a shape selected from the group consisting of a ball, a cylinder, a teardrop, a cube, a pyramid, a diamond and a hook.

16. The device of claim 14, wherein the sharpened distal tip has a shape selected from the group consisting of pointed, beveled, double-beveled, drill-tip shaped, and corkscrew.

* * * * *